(12) United States Patent
Lee et al.

(10) Patent No.: US 12,714,307 B2
(45) Date of Patent: Aug. 25, 2026

(54) METHODS AND SYSTEMS FOR DYNAMICALLY ADJUSTING EYE TEST SEQUENCES IN VIRTUAL EYE TESTS

(71) Applicant: Zenni Optical, Inc., Novato, CA (US)

(72) Inventors: Steven Lee, Barrington, IL (US); Julia Zhen, Novato, CA (US); ChyrSong Ting, Novato, CA (US); Sophia Moh, Daly City, CA (US); Matthew James Golino, Brookhaven, GA (US); Justin Paul Dempsey, Ottawa (CA); Jeffrey Joseph Fillingham, Dartmouth (CA)

(73) Assignee: Zenni Optical, Inc., Novato, CA (US)

( * ) Notice: Subject to any disclaimer, the term of this patent is extended or adjusted under 35 U.S.C. 154(b) by 147 days.

(21) Appl. No.: 18/759,678

(22) Filed: Jun. 28, 2024

(65) Prior Publication Data

US 2026/0000295 A1 Jan. 1, 2026

(51) Int. Cl.

| | |
|---|---|
| ***A61B 3/14*** | (2006.01) |
| ***A61B 3/113*** | (2006.01) |
| ***G02B 27/01*** | (2006.01) |
| ***G16H 10/60*** | (2018.01) |

(52) U.S. Cl.

CPC ................ *A61B 3/14* (2013.01); *A61B 3/113* (2013.01); *G02B 27/017* (2013.01); *G16H 10/60* (2018.01)

(58) Field of Classification Search

CPC .......... A61B 3/14; A61B 3/113; G16H 10/60; G02B 27/017

USPC .......................................................... 351/205

See application file for complete search history.

(56) References Cited

U.S. PATENT DOCUMENTS

| | | |
|---|---|---|
| 2,352,500 A | 6/1944 | Shepard |
| 4,861,156 A | 8/1989 | Terry |
| 5,737,060 A | 4/1998 | Kasha, Jr. |
| 5,767,940 A | 6/1998 | Hayashi et al. |
| 5,880,814 A | 3/1999 | McKnight et al. |
| 6,592,222 B2 | 7/2003 | Massengill et al. |
| 7,784,948 B2 | 8/2010 | Nozawa et al. |
| 10,238,280 B2 | 3/2019 | Maeda et al. |

(Continued)

FOREIGN PATENT DOCUMENTS

| | | |
|---|---|---|
| CN | 2904944 Y | 5/2007 |
| CN | 109431445 A | 3/2019 |

(Continued)

*Primary Examiner* — Wyatt A Stoffa
*Assistant Examiner* — Mitchell T Oestreich
(74) *Attorney, Agent, or Firm* — Morgan, Lewis & Bockius LLP

(57) ABSTRACT

A vision test can be implemented in a virtual reality (VR) environment using a computer device that includes a head-mounted display (HMD). The computer device can obtain historical vision data of a patient user. Based on the historical vision data, the computer device determines an ordered sequence of vision tests including a first vision test for the patient user. The first vision test is followed by a set of one or more subsequent vision tests of the ordered sequence of vision tests. The computer device executes a user application configured to enable the ordered sequence of vision tests by rendering a user interface on the display. A first visual stimulus of the first vision test is displayed on the user interface. The computer device obtains a user response to the first visual stimulus, and dynamically adjusts one or more subsequent visual stimuli based on the user response.

20 Claims, 29 Drawing Sheets

(56) References Cited

U.S. PATENT DOCUMENTS

| | | | | |
|---|---|---|---|---|
| 11,178,389 | B2 | 11/2021 | Sinha et al. | |
| 11,432,718 | B2 | 9/2022 | Xu et al. | |
| 11,768,594 | B2 | 9/2023 | Cameron | |
| 11,793,403 | B2 | 10/2023 | Tran et al. | |
| 12,011,224 | B2 | 6/2024 | Goyal et al. | |
| 12,210,149 | B2 | 1/2025 | Jin et al. | |
| 2012/0147163 | A1 | 6/2012 | Kaminsky | |
| 2016/0202757 | A1 | 7/2016 | Miao et al. | |
| 2016/0246943 | A1* | 8/2016 | Lake | G16H 15/00 |
| 2016/0324416 | A1 | 11/2016 | Fateh | |
| 2017/0293356 | A1 | 10/2017 | Khaderi et al. | |
| 2018/0008141 | A1 | 1/2018 | Krueger | |
| 2018/0095539 | A1 | 4/2018 | Zhang et al. | |
| 2019/0008441 | A1 | 1/2019 | Guzik | |
| 2019/0156100 | A1 | 5/2019 | Rougeaux et al. | |
| 2019/0246890 | A1 | 8/2019 | Kerasidis et al. | |
| 2019/0298166 | A1 | 10/2019 | Smith et al. | |
| 2019/0328305 | A1 | 10/2019 | Wood et al. | |
| 2019/0350452 | A1 | 11/2019 | Lewis | |
| 2020/0073476 | A1 | 3/2020 | Tiwari et al. | |
| 2020/0305707 | A1 | 10/2020 | Fink et al. | |
| 2020/0312269 | A1 | 10/2020 | Nasti et al. | |
| 2021/0330185 | A1 | 10/2021 | Krukowski et al. | |
| 2022/0125299 | A1 | 4/2022 | Abou Shousha | |
| 2023/0293004 | A1 | 9/2023 | Tavakkoli | |
| 2024/0315548 | A1 | 9/2024 | Brugger et al. | |

FOREIGN PATENT DOCUMENTS

| | | | |
|---|---|---|---|
| GR | 1005651 | B | 9/2007 |
| HU | 185600 | B | 2/1985 |
| JP | 2000079095 | A | 3/2000 |
| JP | 2001275968 | A | 10/2001 |
| JP | 2001286442 | A | 10/2001 |
| JP | 3259920 | B2 | 2/2002 |
| JP | 2002051981 | A | 2/2002 |
| JP | 2003038440 | A | 2/2003 |
| JP | 2003079574 | A | 3/2003 |
| JP | 3655129 | B2 | 6/2005 |
| JP | 2012100758 | A | 5/2012 |
| JP | 5007435 | B2 | 8/2012 |
| WO | 1994013192 | A1 | 6/1994 |
| WO | 2011022428 | A2 | 2/2011 |
| WO | 2016165272 | A1 | 10/2016 |
| WO | 2017070704 | A2 | 4/2017 |
| WO | 2021018224 | A1 | 2/2021 |
| WO | 2022111663 | A1 | 6/2022 |

* cited by examiner

METHODS AND SYSTEMS FOR DYNAMICALLY ADJUSTING EYE TEST SEQUENCES IN VIRTUAL EYE TESTS

TECHNICAL FIELD

The present inventions relate to vision test technology, and more specifically, to methods, systems, devices, and non-statutory computer-readable storage media that can be applied to implementing vision tests in an extended reality environment.

BACKGROUND

Traditional methods for visual acuity assessment do not allow for dynamic adjustment of test parameters, leading to less accurate assessments, nor can they be implemented to test eyes and vision at home using household devices in a very environment locked manner.

SUMMARY

The present disclosure relates to innovative methods and systems that can revolutionize vision care, making vision testing and other exams more accessible and affordable for patients. Additionally, it is contemplated that the principles and features of the present disclosure can be implemented in numerous other applications of display technology, including headsets, heads-up displays, and other microdisplays (e.g., microLED and microOLED) to address challenges and limitations inherent in such products and their uses.

Some implementations of the present disclosure are directed to a method of implementing a virtual vision test at an electronic device that includes a head-mounted display (HMD) and a camera. The method can comprise executing a user application configured to enable the virtual vision test; generating a virtual reality (VR) user interface corresponding to a three-dimensional (3D) virtual environment; focusing the camera on an eye area of a user wearing the electronic device; displaying, on the user interface, a visual stimulus corresponding to the virtual vision test; while displaying the visual stimulus, in real time, capturing a sequence of eye images using the camera of the electronic device; determining eye movement information including a temporal sequence of eyeball positions based on the sequence of eye images; and comparing the visual stimulus and the eye movement information to determine an eye health condition.

Some implementations of the present disclosure are directed to a method of implementing a virtual vision test at an electronic device including a head-mounted display (HMD), one or more head straps, and a plurality of electrodes integrated in the one or more head straps. The method can comprise executing a user application configured to enable the virtual vision test; generating a virtual reality (VR) user interface corresponding to a three-dimensional (3D) virtual environment; rendering, on the HMD, a user interface including a first visual stimulus corresponding to the virtual vision test; while displaying the visual stimulus, in real time: collecting a plurality of electrical signals by a plurality of electrodes that contact a head of a user; and determining information of at least one of a second visual stimulus following the first visual stimulus and a user response to the first visual stimulus based on the plurality of electrical signals.

Some implementations of the present disclosure are directed to a method of implementing a virtual vision test at an electronic device including a head-mounted display (HMD). The method can comprise establishing a wireless communication link with a wearable device associated with a user of the electronic device; rendering, on the HMD, a user interface including a first visual stimulus corresponding to the virtual vision test; and while displaying the visual stimulus, in real time: collecting a stream of biometric data from the wireless communication link via the wireless communication link; and determining information of at least one of a second visual stimulus following the first visual stimulus and a user response to the first visual stimulus based on the stream of biometric data.

Some implementations of the present disclosure are directed to a method of implementing a virtual vision test at an electronic device including a head-mounted display (HMD) and a camera. The method can comprise directing the camera to an eye area of a user wearing the electronic device; displaying, on the HMD, a visual stimulus; while displaying the visual stimulus, in real time, capturing a sequence of eye images using the camera of the electronic device, each eye image including a respective region of interest (ROI) corresponding to a subset of the eye area of the user; extracting biomedical data from the sequence of eye images; obtaining a user response to the visual stimulus; and generating an output based on the user response and the biomedical data, the output indicating at least whether the user response satisfies a criterion.

Some implementations of the present disclosure are directed to a method for testing vision at a computer device including a display, one or more processors, and memory. The method can comprise obtaining historical vision data of a patient user associated with the computer device; based on the historical vision data, determining an ordered sequence of vision tests including a first vision test for the patient user, wherein the first vision test is followed by a set of one or more subsequent vision tests of the ordered sequence of vision tests; executing a user application configured to enable the ordered sequence of vision tests, including rendering a user interface on the display; displaying, on the user interface, a first visual stimulus corresponding to the first vision test; obtaining a user response to the first visual stimulus; and dynamically adjusting a set of one or more subsequent visual stimuli based on the user response to the first vision test.

Some implementations of the present disclosure are directed to a method for displaying media content at an electronic device including a display, one or more processors, and memory. The method can comprise obtaining the media content to be rendered on the display; obtaining information of a visual deficiency of a user associated with the display; based on the information of the visual deficiency of the user, compensating the media content to generate compensated media content; and rendering the compensated media content on the display for the user.

In some embodiments, a user application can be implemented by a head-mounted display device (HDD) configured to create a customized extended reality (XR) environment for a user engaged on an XR information platform. Products may be rendered for the user in a three-dimension format in the XR environment, thereby facilitating eyewear selection and fitting. The XR can be an umbrella term encapsulating Augmented Reality (AR), Virtual Reality (VR), Mixed Reality (MR), and everything in between. In this application, any embodiments that apply a VR system can be implemented using an AR or MR system as well.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE FIGURES

Various features of illustrative embodiments of the inventions are described below with reference to the drawings. The illustrated embodiments are intended to illustrate, but not to limit, the inventions.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Moreover, various aspects of the present disclosure can be implemented in combination with aspects of other virtual-reality technology developed by the present applicant, for example, in copending U.S. Patent App. Nos.: 63/560,623 filed on Mar. 1, 2024, 63/569,095 filed on Mar. 23, 2024, 63/642,571 filed on May 3, 2024, 63/642,583 filed on May 3, 2024, 63/642,593 filed on May 3, 2024, 63/642,604 filed on May 3, 2024, and 63/644,457 filed on May 8, 2024, the entireties of each of which is incorporated herein by reference. Aspects of these copending cases can be implemented in combination with some embodiments disclosed herein, whether in addition to features thereof or as an alternative to a particular feature of an embodiment disclosed herein.

Figure 1:
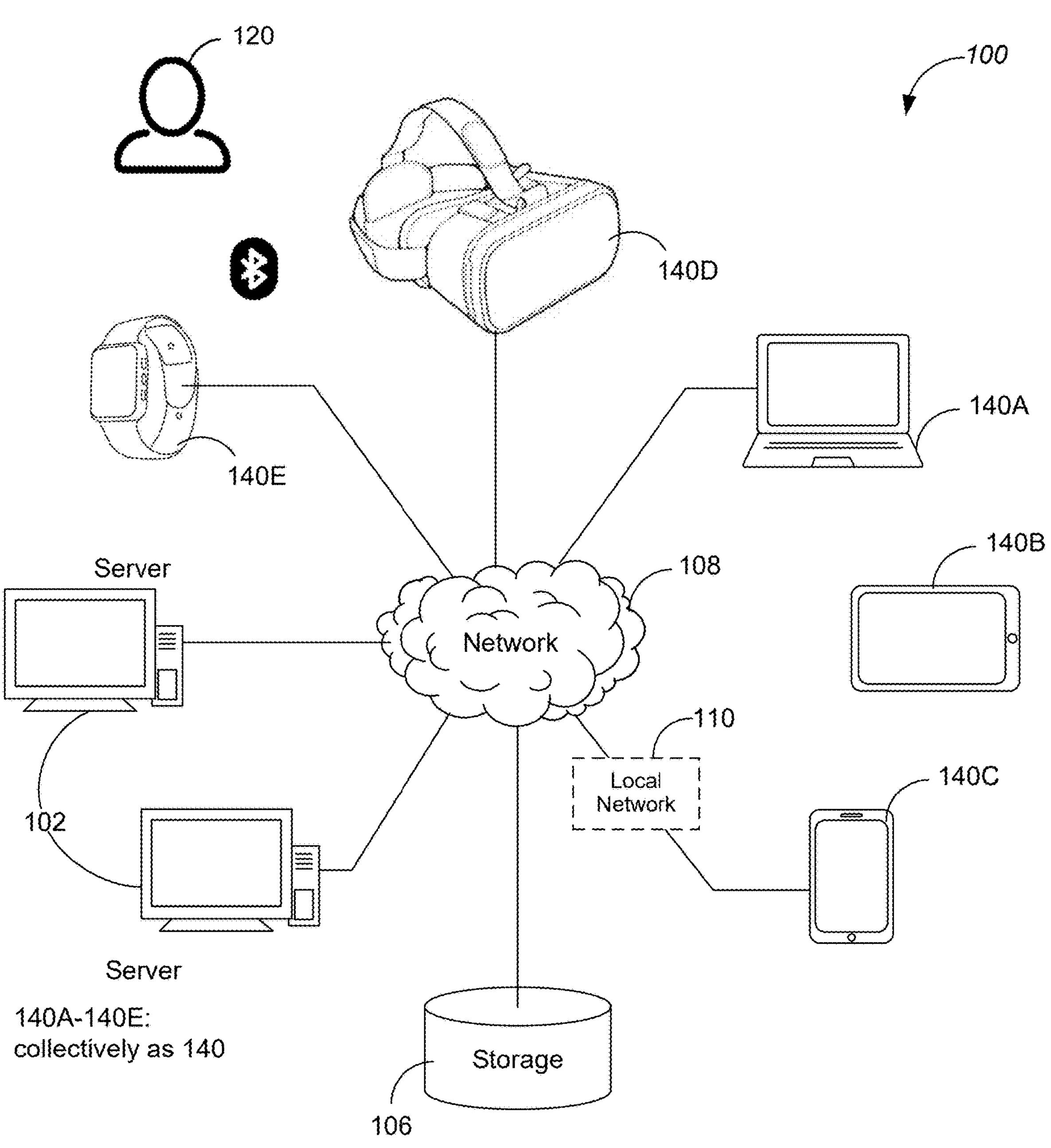
FIG. 1 is an example data processing environment having one or more servers communicatively coupled to one or more computer devices (e.g., a headset device), in accordance with some embodiments.

Referring now to the figures, FIG. 1 is an example data processing environment 100 having one or more servers 102 communicatively coupled to one or more computer devices 140 (e.g., a headset device 140D), in accordance with some embodiments. The one or more computer devices 140 are electronic devices having computational capabilities, and may be, for example, desktop computers 140A, tablet computers 140B, mobile phones 140C, or intelligent, multi-sensing, network-connected home devices (e.g., a depth camera, a visible light camera).

In some implementations, the one or more computer devices 140 can include a headset device 140D (also called a head-mounted display (HMD) device 140D) configured to render extended reality content. In some implementations, the one or more computer devices 140 can include a wireless wearable device 140E (e.g., a smart watch, a fitness band) configured to track health data (e.g., heart rate, quality of sleep) and activity data (e.g., steps walked, stairs climbed) of a user wearing the device 140E. Each computer device 140 can collect data or user inputs, executes user applications, and present outputs on its user interface. The collected data or user inputs can be processed locally at the computer device 140 and/or remotely by the server(s) 102. The one or more servers 102 can provide system data (e.g., boot files, operating system images, and user applications) to the computer devices 140, and in some embodiments, processes the data and user inputs received from the computer device(s) 140 when the user applications are executed on the computer devices 140. In some embodiments, the data processing environment 100 can further include a storage 106 for storing data related to the servers 102, computer devices 140, and applications executed on the computer devices 140. For example, storage 106 may store video content, static visual content, and/or audio data.

The one or more servers 102 can enable real-time data communication with the computer devices 140 that can be remote from each other or from the one or more servers 102. Further, in some embodiments, the one or more servers 102 can implement data processing tasks that are not completed locally by the computer devices 140. For example, the computer devices 140 can include a game console (e.g., the headset device 140D) that executes an interactive online gaming application (e.g., for visual assessment or eyewear fitting). The game console receives a user instruction and sends it to a server 102 with user data. The server 102 generates a stream of video data based on the user instruction and user data, and provides the stream of video data for display on the game console and other computer devices that can be engaged in the same session with the game console.

The one or more servers 102, one or more computer devices 140, and storage 106 can be communicatively coupled to each other via one or more communication networks 108, which are the medium used to provide communications links between these devices and computers connected together within the data processing environment 100. The one or more communication networks 108 may include connections, such as wire, wireless communication links, or fiber optic cables. Examples of the one or more communication networks 108 include local area networks (LAN), wide area networks (WAN) such as the Internet, or a combination thereof. The one or more communication networks 108 are, optionally, implemented using any known network protocol includes various wired or wireless protocols, such as Ethernet, Universal Serial Bus (USB), FIREWIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VOIP), Wi-MAX, or any other suitable communication protocol. A connection to the one or more communication networks 108 may be established either directly (e.g., using 1G/4G connectivity to a wireless carrier), or through a network interface 110 (e.g., using a router, switch, gateway, hub, or an intelligent, dedicated whole-home control node), or through any combination thereof. As such, the one or more communication networks 108 can represent the Internet of a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other electronic systems that route data and messages.

In some embodiments, the headset device 140D can be communicatively coupled to a data processing environment 100. The headset device 140D includes one or more cameras (e.g., a visible light camera, a depth camera), a microphone, a speaker, one or more inertial sensors (e.g., gyroscope, accelerometer), and a display. In some embodiments, the camera may capture hand gestures of a user wearing the headset device 140D. In some embodiments, the microphone records ambient sound includes user's voice commands.

In some embodiments, the headset device 140D may be communicatively coupled to one or more servers 102 and enables a centralized vision test management platform with the one or more servers 102. This vision test management platform may aggregate data (e.g., visual stimuli 338, sensor data 342, vision test results 344) from a plurality of user accounts associated with a plurality of users, analyze the aggregated data, and track vision health trends for individual users or user groups. In some embodiments, data may be communicated between a headset device 140D and a server 102 in an encrypted format. In some embodiments, the vision test management platform is coupled to a global health database storing epidemiological data. The vision test management platform can be configured to cross-reference the data collected from its user accounts with the epidemiological data to identify an emerging pattern and a public health concern. For example, a teenager's vision data may be collected and analyzed during an extended duration of time (e.g., 10 years) to identify an individual vision development trend and was cross-referenced with an average vision development trend extracted from the global health database. A doctor can rely on a cross-referencing result to determine whether the individual vision development trend is normal or whether the teenager's eyesight drops faster than average teenagers. As such, various embodiments of the vision test management platform may integrate biometric data and global health analytics and provides a secure, personalized, and interactive environment for vision testing, which can improve precision and user experience of vision assessments and contributes to broader public health monitoring and research initiatives.

Figure 2:
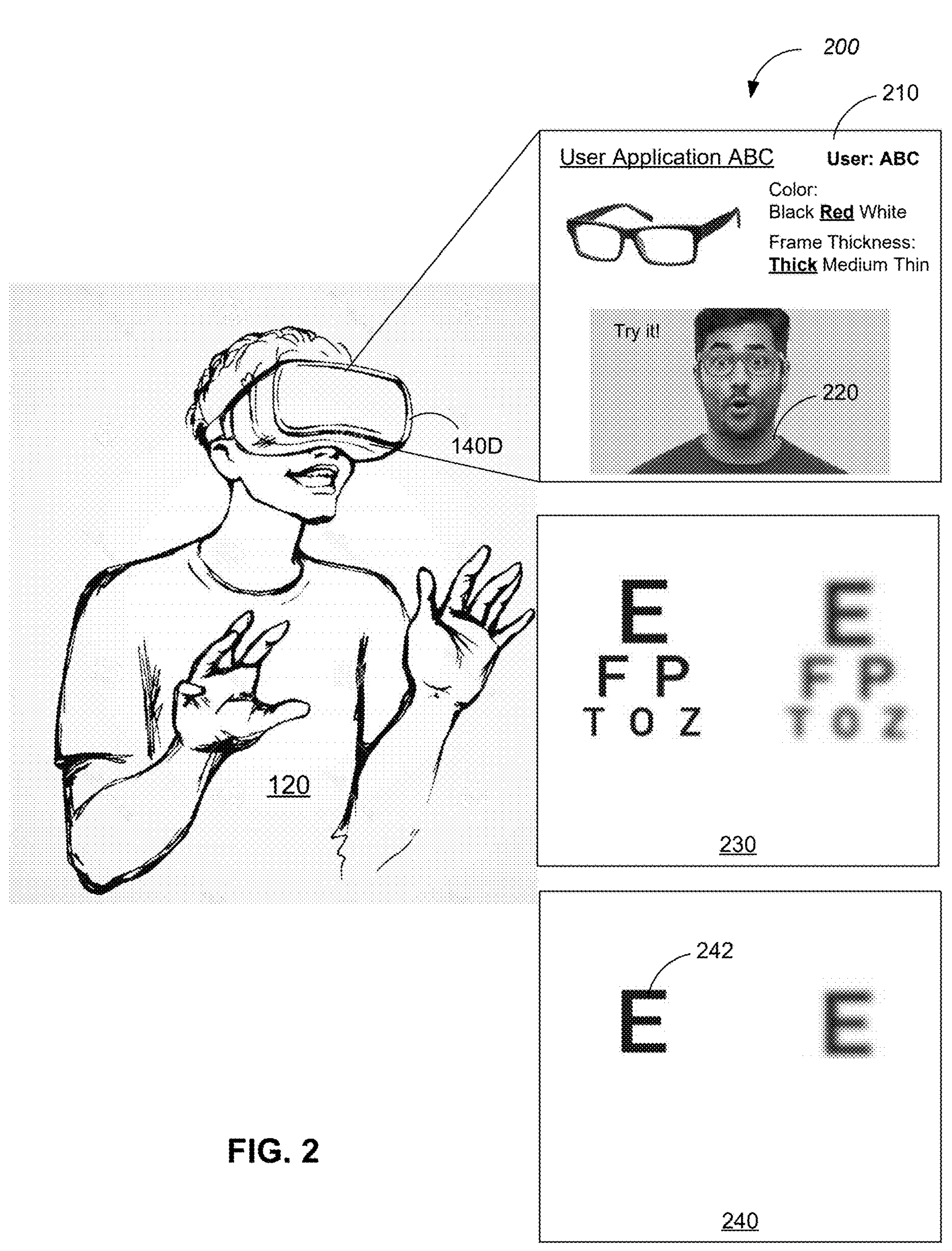
FIG. 2 is an environment in which a computer device (e.g., a headset device) is applied to facilitate visual assessment or eyewear fitting, in accordance with some embodiments.

FIG. 2 is an environment 200 in which a computer device 140 (e.g., a headset device 140D) is applied to facilitate visual assessment or eyewear fitting, in accordance with some embodiments. The XR headset device 140D may be communicatively coupled within the data processing environment 100. The XR headset device 140D may include one or more cameras (e.g., a visible light camera, a depth camera), a microphone, a speaker, one or more inertial sensors (e.g., gyroscope, accelerometer), and a display. In some embodiments, the camera may capture hand gestures of a user wearing the XR headset device 140D. In some embodiments, the microphone may record ambient sound includes user's voice commands. The XR headset device 140D may execute a client-side eyewear fitting application 326 or a client-side visual assessment application 328 (FIG. 3) via a user account associated with a user 120 (e.g., an optometrist user, an optician user, a patient user). In some implementations, a computer device 140 (e.g., a mobile phone 140C) distinct from the XR headset device 140D can be used to implement the client-side eyewear fitting application 326 or visual assessment application 328 (FIG. 3).

In some embodiments, a first user interface 210 can be displayed on a computer device 140 (e.g., the headset device 140D) associated with the user 120. In some embodiments, an eyewear can be tried on or displayed as being worn by a 2D or 3D image 220 of the user 120. The server 102 or computer device 140 may receive, from the first user interface 210, a user feedback message indicating an issue, requesting further improvement, or confirming a fit. In some embodiments, a second user interface 230 can be displayed on a computer device 140 associated with the user 120. The second user interface 230 may include a plurality of optotypes (e.g., six optotypes E, F, P, T, O, and Z) having different sizes. In some embodiments, a third user interface 240 can be displayed on a computer device 140 associated with the user 120. The second user interface 230 can display a temporal sequence of optotypes having respective sizes. Each optotype of a corresponding size can be displayed at one time.

Figure 3:
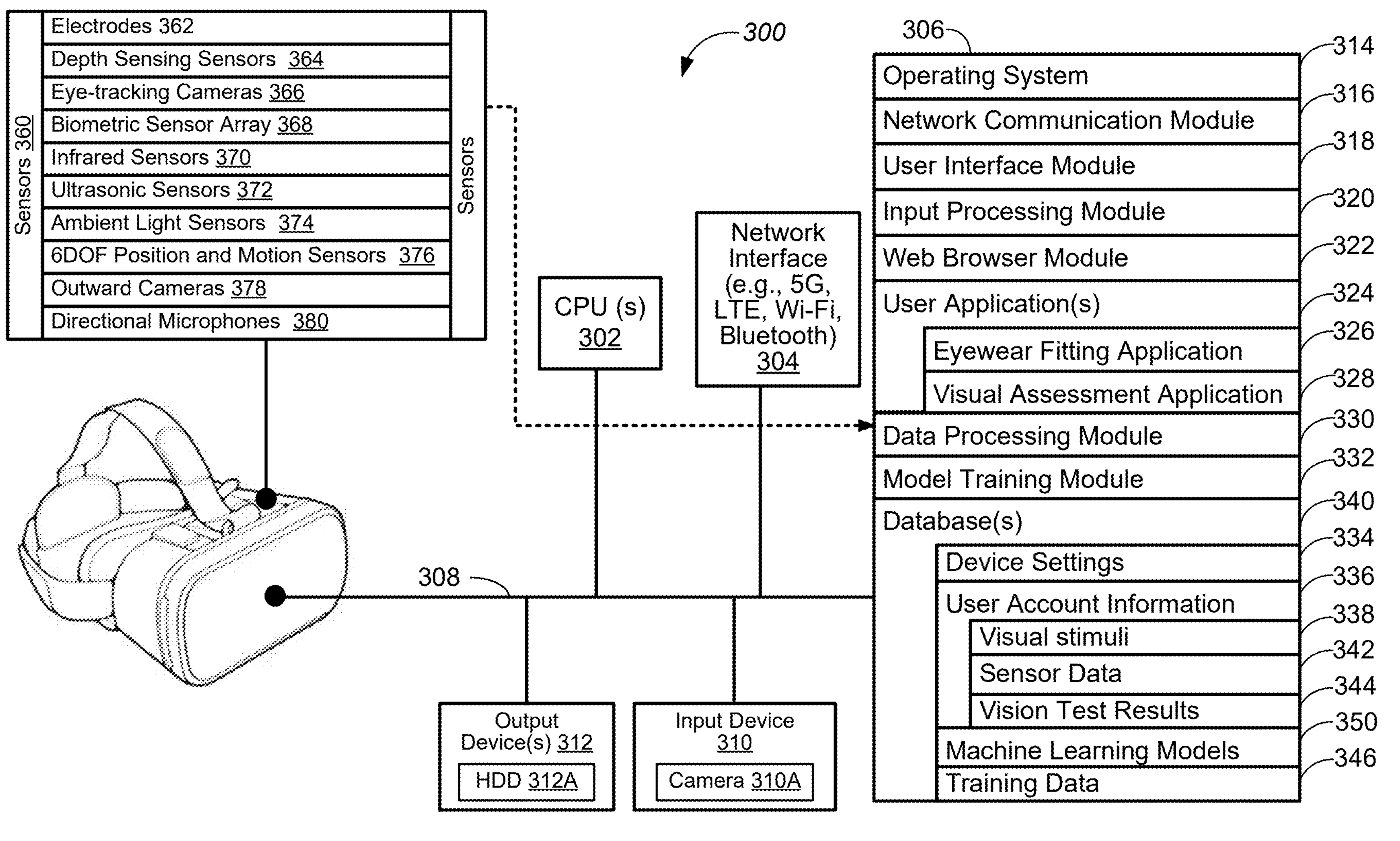
FIG. 3 is a block diagram of a computer system (e.g., including a headset device) configured to implement vision assessment or eyewear fitting, in accordance with some embodiments.

FIG. 3 is a block diagram of a computer system 300 (e.g., including a headset device 140D, a server, or a combination thereof) configured to implement vision assessment or eyewear fitting, in accordance with some embodiments. The computer system 300 can include one or more processing units (CPUs) 302, one or more network interfaces 304, memory 306, and one or more communication buses 308 for interconnecting these components (sometimes called a chipset). The computer system 300 may include one or more input devices 310 that facilitate user input, such as a keyboard, a mouse, a voice-command input unit or microphone, a touch screen display, a touch-sensitive input pad, a gesture capturing camera, or other input buttons or controls. Furthermore, in some embodiments, the computer device 140 of the computer system 300 may use a microphone for voice recognition or an eye tracking camera 366 for tracking eyeball movement. In some implementations, the computer device 140 may include one or more optical cameras (e.g., an RGB camera), scanners, or photo sensor units for capturing images. The computer system 300 may also include one or more output devices 312 that enable presentation of user interfaces 210 and media content. The one or more output devices 312 may include one or more speakers and/or one or more visual displays.

The computer system 300 may include one or more sensors 360, which further may include one or more of: a plurality of electrodes 362, one or more depth sensing sensors 364, one or more eye tracking cameras 366, a biometric sensor array 368, one or more infrared sensors 370, one or more ultrasonic sensors 372, one or more ambient sensors 374, one or more motion sensors (e.g., six degree of freedom (6DOF) position and motion sensors 376), one or more outward camera 378, and one or more directional microphones 380. It is noted that the one or more sensors 360 can also be included in the input device 310 and used to collect data to the computer system 300.

Memory 306 may include high-speed random-access memory, such as DRAM, SRAM, DDR RAM, or other random-access solid state memory devices; and, optionally, may include non-volatile memory, such as one or more magnetic disk storage devices, one or more optical disk storage devices, one or more flash memory devices, or one or more other non-volatile solid state storage devices. Memory 306, optionally, may include one or more storage devices remotely located from one or more processing units 302. Memory 306, or alternatively the non-volatile memory within memory 306, may include a non-transitory computer readable storage medium. In some implementations, memory 306, or the non-transitory computer readable storage medium of memory 306, may store the following programs, modules, and data structures, or a subset or superset thereof:

- Operating system 314 including procedures for handling various basic system services and for performing hardware dependent tasks;
- Network communication module 316 for connecting each server 102 or computer device 140 to other devices (e.g., server 102, computer device 140, or storage 106) via one or more network interfaces 304 (wired or wireless) and one or more communication networks 108, such as the Internet, other wide area networks, local area networks, metropolitan area networks, and so on;
- User interface module 318 for enabling presentation of information (e.g., a graphical user interface for application(s) 324, widgets, websites and web pages thereof, and/or games, audio and/or video content, text, etc.) at each computer device 140 via one or more output devices 312 (e.g., displays, speakers, etc.);
- Input processing module 320 for detecting one or more user inputs or interactions from one of the one or more input devices 310 and interpreting the detected input or interaction;
- Web browser module 322 for navigating, requesting (e.g., via HTTP), and displaying websites and web pages thereof may include a web interface for logging into a user account associated with a computer device 140 or another electronic device, controlling the computer device if associated with the user account, and editing and reviewing settings and data that are associated with the user account;
- One or more user applications 324 for execution by the computer system 300 (e.g., games, social network applications, smart home applications, extended reality application, and/or other web or non-web-based applications for controlling another electronic device and reviewing data captured by such devices), where in some embodiments, an eyewear fitting application 326 can be executed to implement eyewear fitting, and has a plurality of user accounts associated with a plurality of users 120 (e.g., technician users and eyewear users), and in some embodiments, a visual assessment application 328 can be executed to evaluate eyesight of a patient user, and has a plurality of user accounts associated with a plurality of users 120 (e.g., an optometrist user, a patient user);

Data processing module 330 for processing data associated with the user applications 324, e.g., using machine learning models 350;

Model training Module 332 for obtaining training data 346 and training machine learning models 350; and One or more databases 340 for storing at least data including one or more of:

Device settings 334 including common device settings (e.g., service tier, device model, storage capacity, processing capabilities, communication capabilities, etc.) of the computer system 300;

User account information 336 for the one or more user applications 324, e.g., user names, security questions, account history data, user preferences, and predefined account settings, where in some embodiments, the user account information 336 may include facial measurements and one or more virtual fitting parameters associated with associated with a user account of an eye fitting application 326, and in some embodiments, the user account information 336 may include visual stimuli 338, sensor data 342, and vision test results 344 associated with a user account of a visual assessment application 328; and Machine learning models 350 including parameters (e.g., weights, biases) used to implement vision test or select eyewear for eyewear users.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise rearranged in some embodiments. In some embodiments, memory 306, optionally, stores a subset of the modules and data structures identified above. Furthermore, memory 306, optionally, stores additional modules and data structures not described above.

Figure 4:
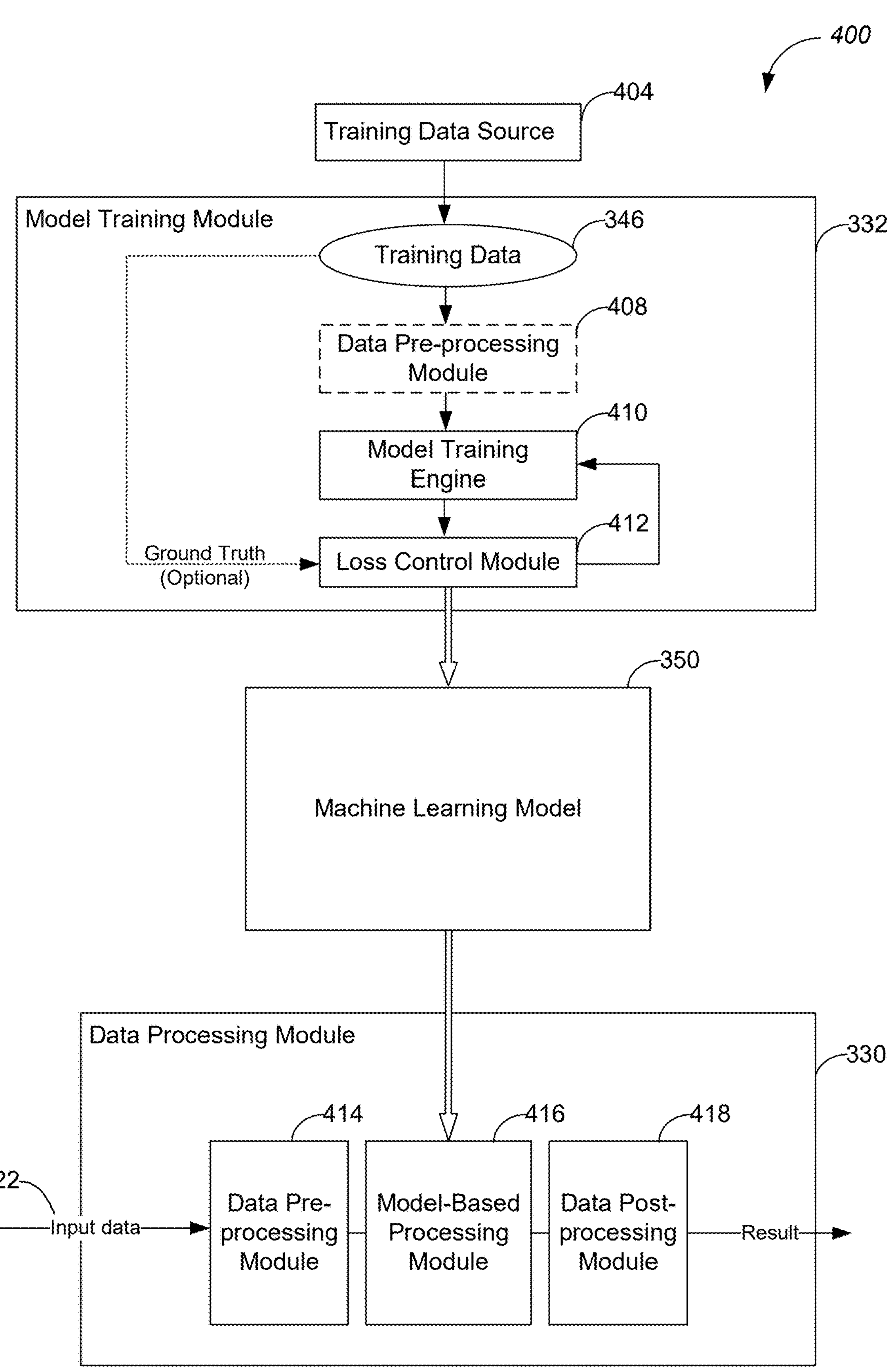
FIG. 4 is a block diagram of a machine learning system for training and applying machine learning models (e.g., for glass making), in accordance with some embodiments.

FIG. 4 is a block diagram of a machine learning system 400 for training and applying machine learning models 350 (e.g., for glass making), in accordance with some embodiments. The machine learning system 400 may include a model training module 332 establishing one or more machine learning models 350 and a data processing module 330 for processing input data 422 using the machine learning model 350. In some embodiments, both the model training module 332 and the data processing module 330 may be located within a computer device 140 (e.g., a VR headset), while a training data source 404 provides training data 346 to the computer device 140. In some embodiments, the training data source 404 may include the data obtained from the computer device 140 itself, from a server 102, from storage 106, or from another electronic device or computer device 140. Alternatively, in some embodiments, the model training module 332 may be located at a server 102, and the data processing module 330 may be located in a computer device 140. The server 102 can train the machine learning model 350 and provide the trained models 350 to the computer device 140 to process real-time input data 422 detected by the computer device 140. In some embodiments, the training data 346 provided by the training data source 404 may include a standard dataset widely used to train machine learning models 350. The input data 422 further may include sensor data. Further, in some embodiments, a subset of the training data 346 may be modified to augment the training data 346. The subset of modified training data may be used in place of or jointly with the subset of training data 346 to train the machine learning models 350.

In some embodiments, the model training module 332 may include a model training engine 410, and a loss control module 412. Each machine learning model 350 may be trained by the model training engine 410 to process corresponding input data 422 and implement a respective task. Specifically, the model training engine 410 may receive the training data 346 corresponding to a machine learning model 350 to be trained and process the training data to build the machine learning model 350. In some embodiments, during this process, the loss control module 412 can monitor a loss function comparing the output associated with the respective training data item to a ground truth of the respective training data item. In these embodiments, the model training engine 410 may modify the machine learning models 350 to reduce the loss, until the loss function satisfies a loss criteria (e.g., a comparison result of the loss function is minimized or reduced below a loss threshold). The machine learning models 350 may thereby be trained and provided to the data processing module 330 of a computer device 140 to process real-time input data 422 from the computer device 140.

In some embodiments, the model training module 402 may further include a data pre-processing module 408 configured to pre-process the training data 346 before the training data 346 is used by the model training engine 410 to train a machine learning model 350. For example, an image pre-processing module 408 is configured to format patients' eye images in the training data 346 into a predefined image format. For example, the preprocessing module 408 may normalize the images to a fixed size, resolution, or contrast level. In another example, an image pre-processing module 408 extracts a region of interest (ROI) corresponding to an eye area.

In some embodiments, the model training module 332 can use supervised learning in which the training data 346 may be labelled and include a desired output for each training data item (also called the ground truth, in some embodiments). In some embodiments, the desirable output may be labelled manually by people or automatically by the model training model 332 before training. In some embodiments, the model training module 332 may use unsupervised learning in which the training data 346 is not labelled. The model training module 332 is configured to identify previously undetected patterns in the training data 346 without preexisting labels and with little or no human supervision. Additionally, in some embodiments, the model training module 332 may use partially supervised learning in which the training data is partially labelled.

In some embodiments, the data processing module 330 may include a data pre-processing module 414, a model-based processing module 416, and a data post-processing module 418. The data pre-processing modules 414 may pre-process input data 422 based on the type of the input data 422. In some embodiments, functions of the data pre-processing modules 414 are consistent with those of the pre-processing module 408. The data pre-processing modules 414 can convert the input data 422 into a predefined data format that is suitable for the inputs of the model-based processing module 416. The model-based processing module 416 may apply the trained machine learning model 350 provided by the model training module 332 to process the pre-processed input data 422. In some embodiments, the model-based processing module 416 can also monitor an error indicator to determine whether the input data 422 has been properly processed in the machine learning model 350. In some embodiments, the processed input data may be further processed by the data post-processing module 418 to create a preferred format or to provide additional information that can be derived from the processed input data. The data processing module 330 may use the processed input data to make eyewear glasses for a patient user.

Figure 22:
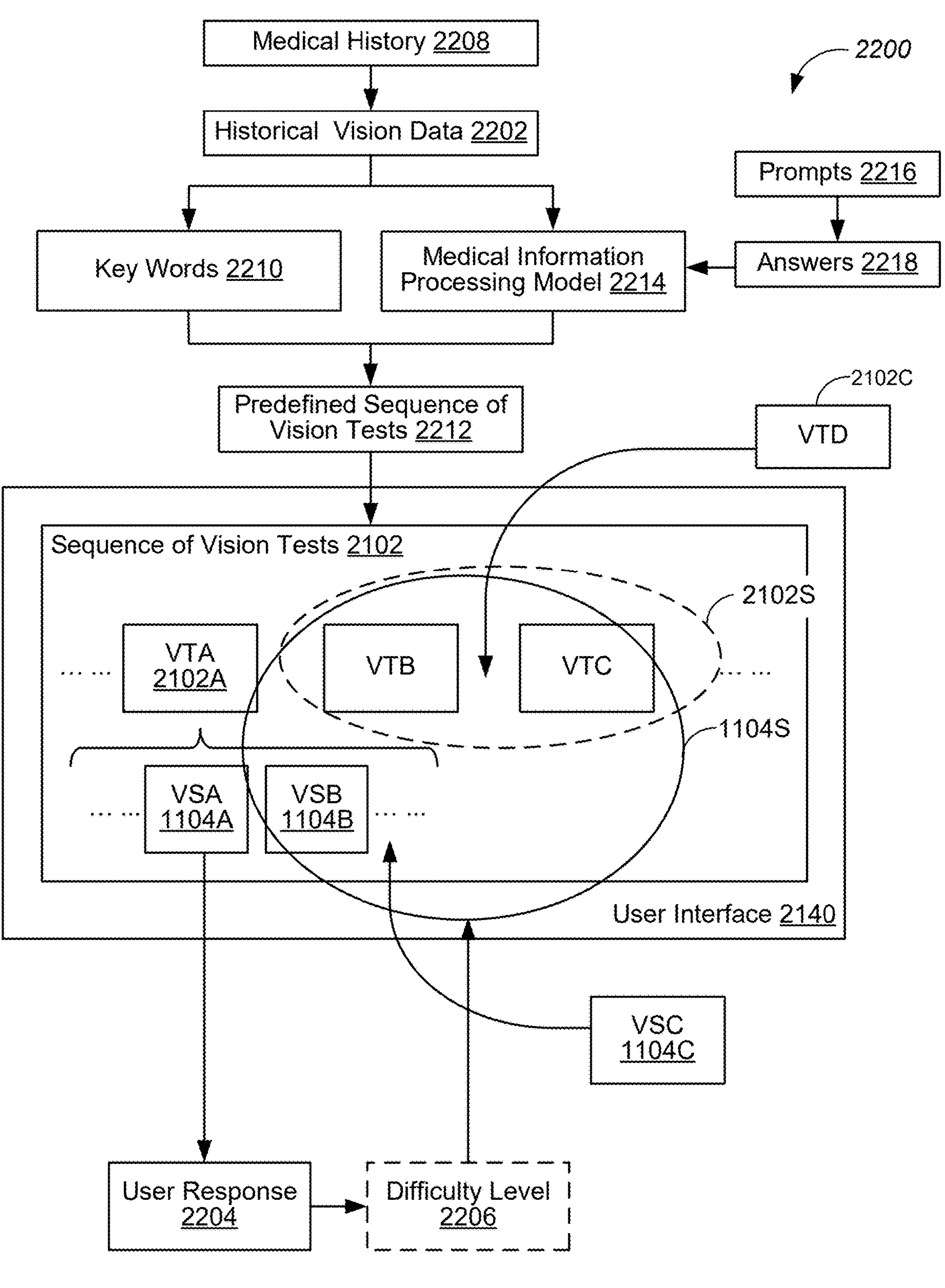
FIG. 22 is a flow diagram of an example method of dynamically adjusting vision tests, in accordance with some embodiments.
Figure 23:
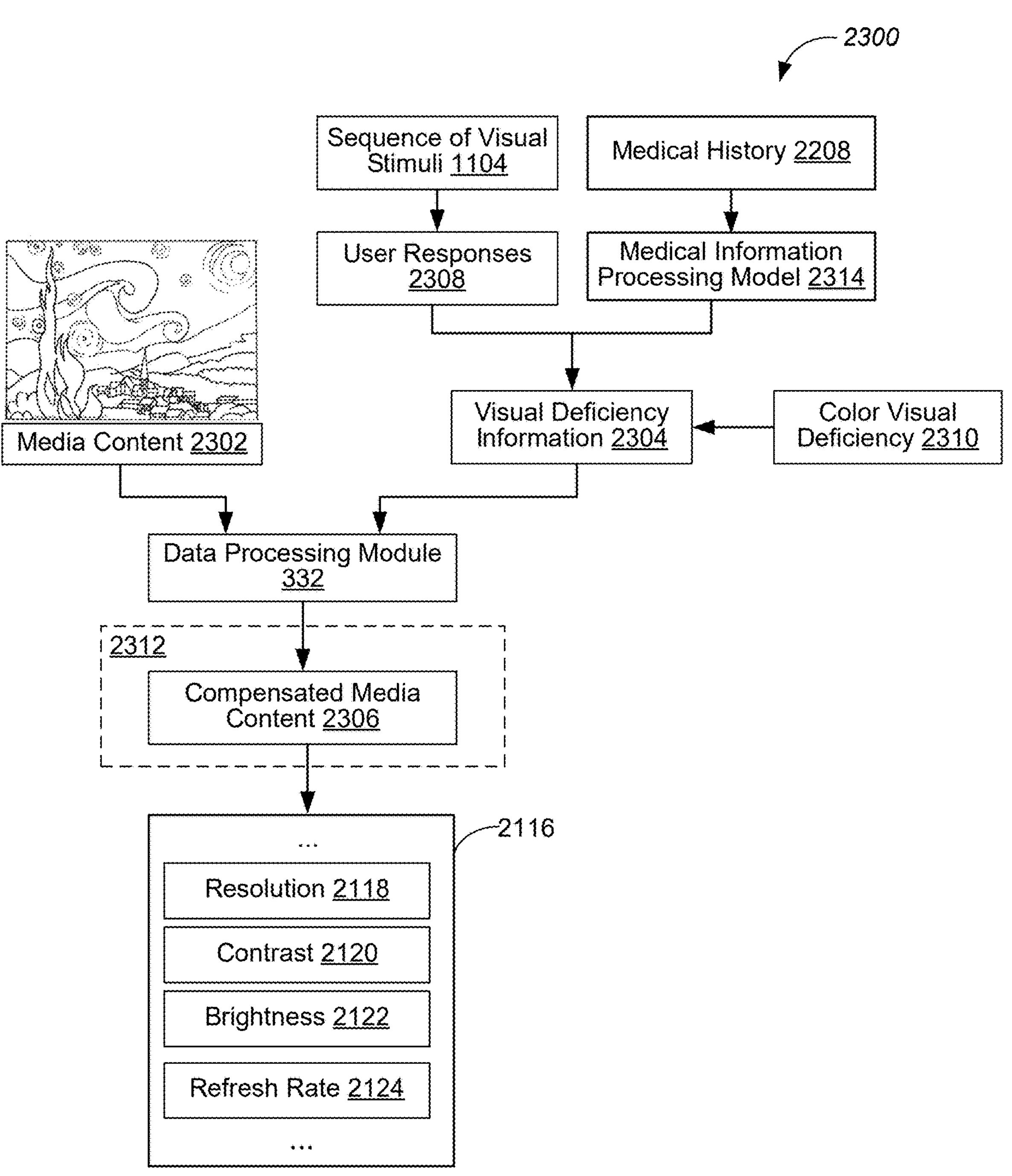
FIG. 23 is a diagram illustrating an example process of dynamically adjusting display of media content based on a visual deficiency of a user, in accordance with some embodiments.

Examples of the machine learning model 350 include, but are not limited to, an eye trajectory model 1202 (FIG. 12), an eye position model 1208 (FIG. 12), an ocular microtremor model 1406 (FIG. 14), a response analysis model 1626 (FIG. 16), a response analysis model 1816 (FIG. 18), a biomedical data model 2004 (FIG. 20), and medical information models 2214 (FIG. 22) and 2312 (FIG. 23).

Figures 5A, 5B:
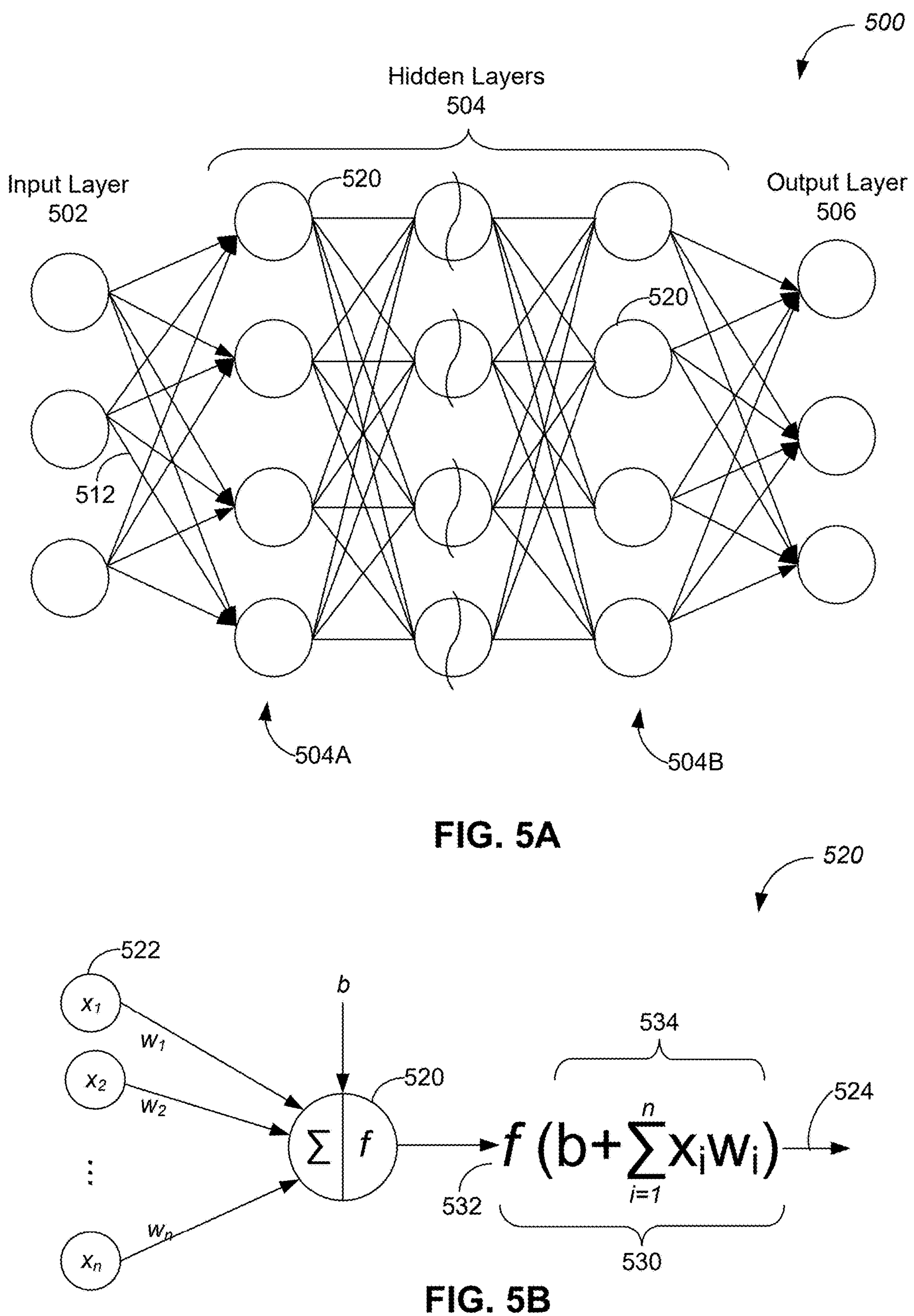
FIG. 5A is a structural diagram of an example neural network applied to process input data in a machine learning model.
FIG. 5B is an example node in the neural network, in accordance with some embodiments.

FIG. 5A is a structural diagram of an example neural network 500 applied to process input data in a machine learning model 350, in accordance with some embodiments. Further, FIG. 5B is an example node 520 in the neural network 500, in accordance with some embodiments. It should be noted that this description is used as an example only, and other types or configurations may be used to implement the embodiments described herein. The machine learning model 350 may be established based on the neural network 500. A corresponding model-based processing module 416 may apply the machine learning model 350 including the neural network 500 to process input data 422 that has been converted to a predefined data format. The neural network 500 may include a collection of nodes 520 that may be connected by links 512. Each node 520 may receive one or more node inputs 522 and applies a propagation function 530 to generate a node output 524 from the one or more node inputs. As the node output 524 is provided via one or more links 512 to one or more other nodes 520, a weight w associated with each link 512 may be applied to the node output 524. Likewise, the one or more node inputs 522 may be combined based on corresponding weights $w_1$, $w_2$, $w_3$, and $w_4$ according to the propagation function 530. In an example, the propagation function 530 is computed by applying a non-linear activation function 532 to a linear weighted combination 534 of the one or more node inputs 522.

The collection of nodes 520 may be organized into layers in the neural network 500. In general, the layers may include an input layer 502 for receiving inputs, an output layer 506 for providing outputs, and one or more hidden layers 504 (e.g., layers 504A and 504B) between the input layer 502 and the output layer 506. A deep neural network has more than one hidden layer 504 between the input layer 502 and the output layer 506. In the neural network 500, each layer may only be connected with its immediately preceding and/or immediately following layer. In some embodiments, a layer may be a "fully connected" layer because each node in the layer is connected to every node in its immediately following layer. In some embodiments, a hidden layer 504 may include two or more nodes that may be connected to the same node in its immediately following layer for down sampling or pooling the two or more nodes. In particular, max pooling may use a maximum value of the two or more nodes in the layer for generating the node of the immediately following layer.

In some embodiments, a convolutional neural network (CNN) may be applied in a machine learning model 350 to process input data. The CNN employs convolution operations and belongs to a class of deep neural networks. The hidden layers 504 of the CNN include convolutional layers. Each node in a convolutional layer may receive inputs from a receptive area associated with a previous layer (e.g., nine nodes). Each convolution layer may use a kernel to combine pixels in a respective area to generate outputs. For example, the kernel may be to a 3×3 matrix including weights applied to combine the pixels in the respective area surrounding each pixel. Video or image data can be pre-processed to a predefined video/image format corresponding to the inputs of the CNN. In some embodiments, the pre-processed video or image data may abstracted by the CNN layers to form a respective feature map. In this way, video and image data can be processed by the CNN for video and image recognition or object detection.

In some embodiments, a recurrent neural network (RNN) is applied in the machine learning model 350 to process input data 422. Nodes in successive layers of the RNN follow a temporal sequence, such that the RNN exhibits a temporal dynamic behavior. In an example, each node 520 of the RNN has a time-varying real-valued activation. It is noted that in some embodiments, two or more types of input data may be processed by the data processing module 330, and two or more types of neural networks (e.g., both a CNN and an RNN) may be applied in the same machine learning model 350 to process the input data jointly.

The training process is a process for calibrating all of the weights $w_i$ for each layer of the neural network 500 using training data 346 that is provided in the input layer 502. The training process typically may include two steps, forward propagation and backward propagation, which may be repeated multiple times until a predefined convergence condition is satisfied. In the forward propagation, the set of weights for different layers may be applied to the input data and intermediate results from the previous layers. In the backward propagation, a margin of error of the output (e.g., a loss function) is measured (e.g., by a loss control module 412), and the weights may be adjusted accordingly to decrease the error. The activation function 532 can be linear, rectified linear, sigmoidal, hyperbolic tangent, or other types. In some embodiments, a network bias term b may be added to the sum of the weighted outputs 534 from the previous layer before the activation function 532 is applied. The network bias b may provide a perturbation that helps the neural network 500 avoid over fitting the training data. In some embodiments, the result of the training may include a network bias parameter b for each layer.

Figure 6A:
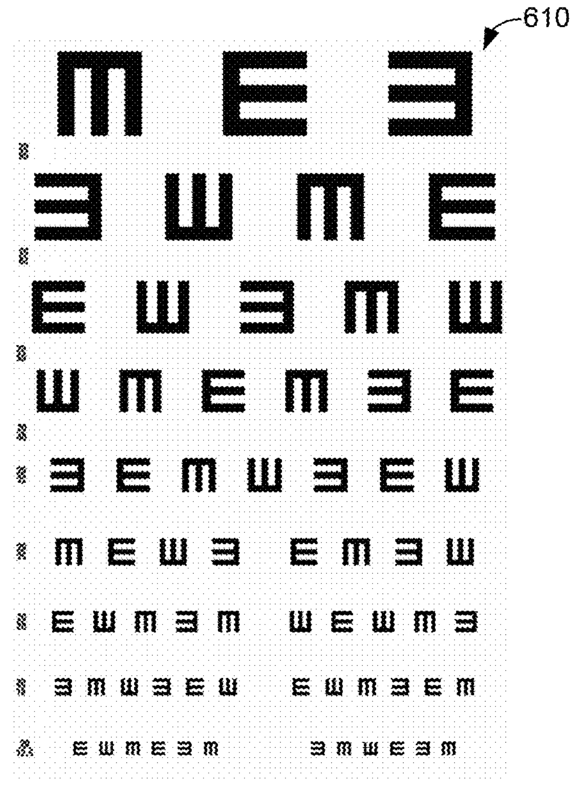
FIG. 6A is an example "tumbling E" chart applied in a visual acuity test.
Figure 6B:
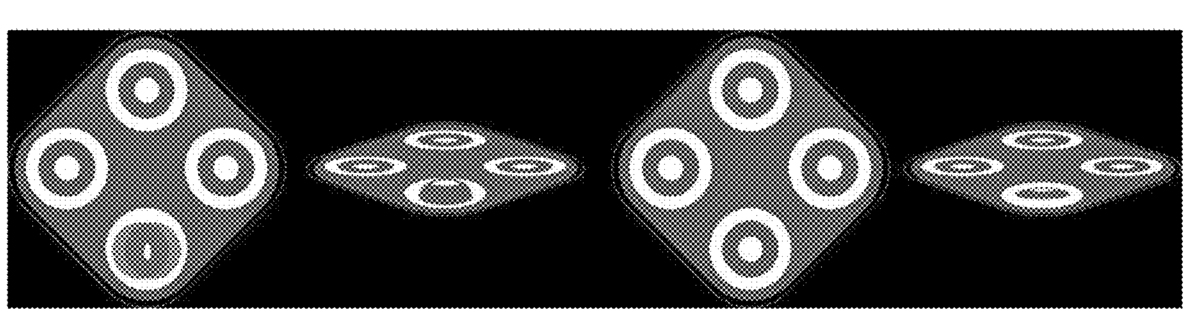
FIGS. 6B-6E are example patterns applied in an astigmatism test, a stereopsis test, a visual field test, and a color blindness test, in accordance with some embodiments.
Figure 6C:
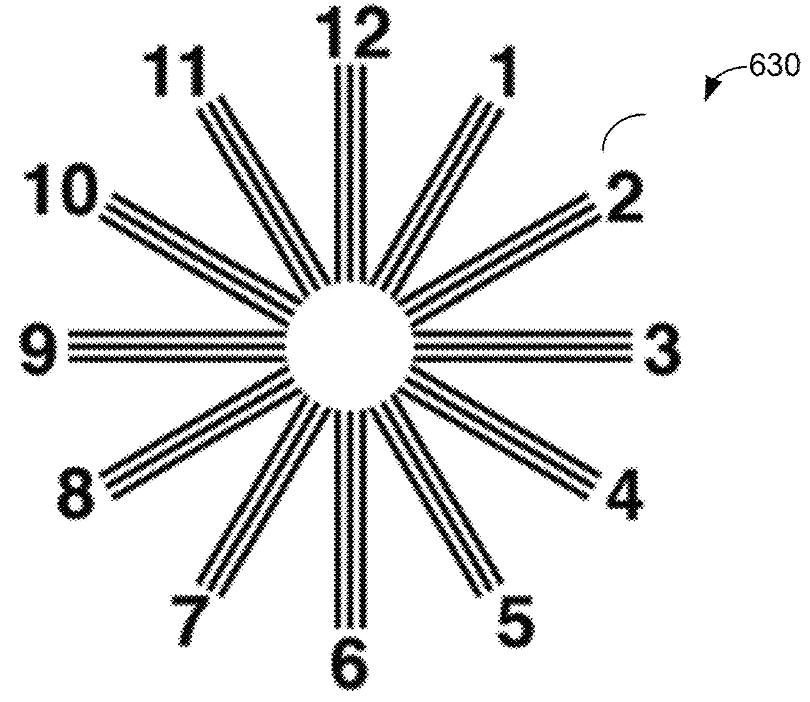
Figure 6D:
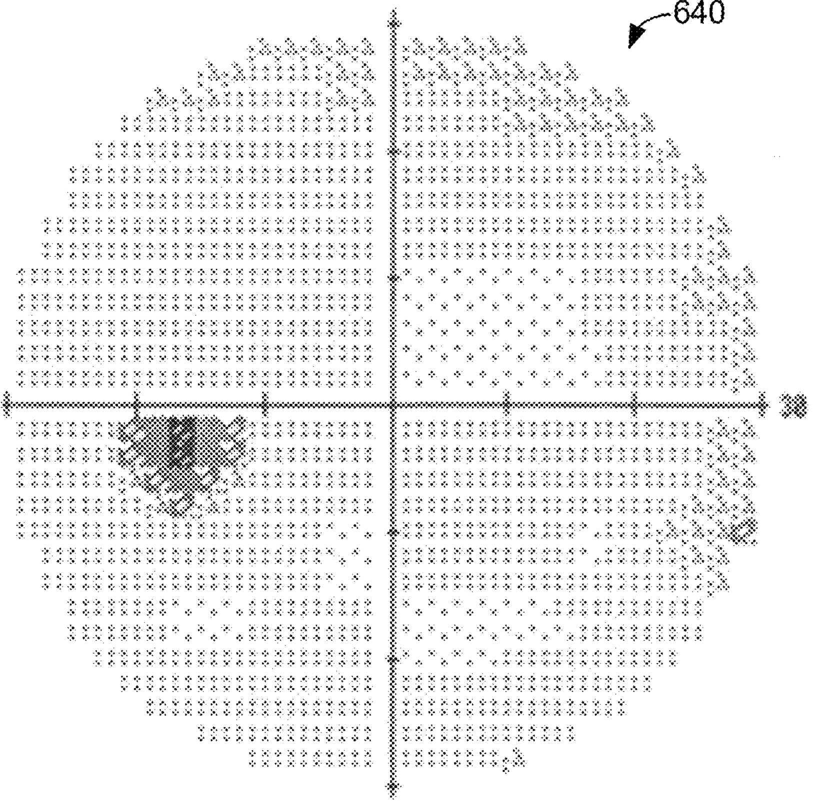
Figure 6E:
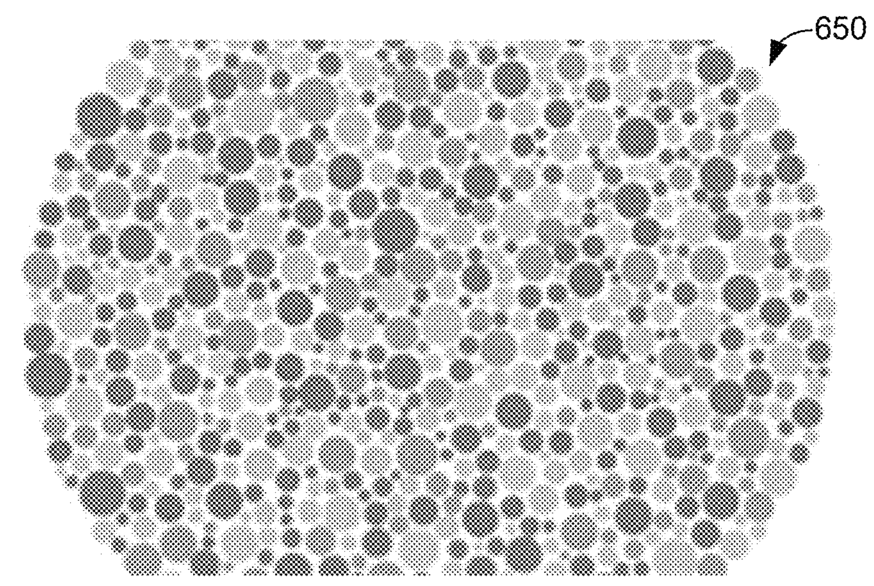

In some embodiments of the present disclosure, a vision test is implemented in a headset device 140D configured to display a user interface creating a three-dimensional (3D) virtual environment. Examples of a vision test implemented in the 3D virtual environment include, but are not limited to a visual acuity test, a visual field test, a visual depth test, a color blindness test, a retinoscopy, a test for stereopsis, a refraction test, an astigmatism test, and a contact lens exam. FIG. 6A is an example "tumbling E" chart 610 applied in a visual acuity test, in accordance with some embodiments. FIGS. 6B, 6C, 6D, and 6E are example patterns 620, 630, 640, and 650 applied in an astigmatism test, a stereopsis test, a visual field test, and a color blindness test, in accordance with some embodiments.

Figure 7:
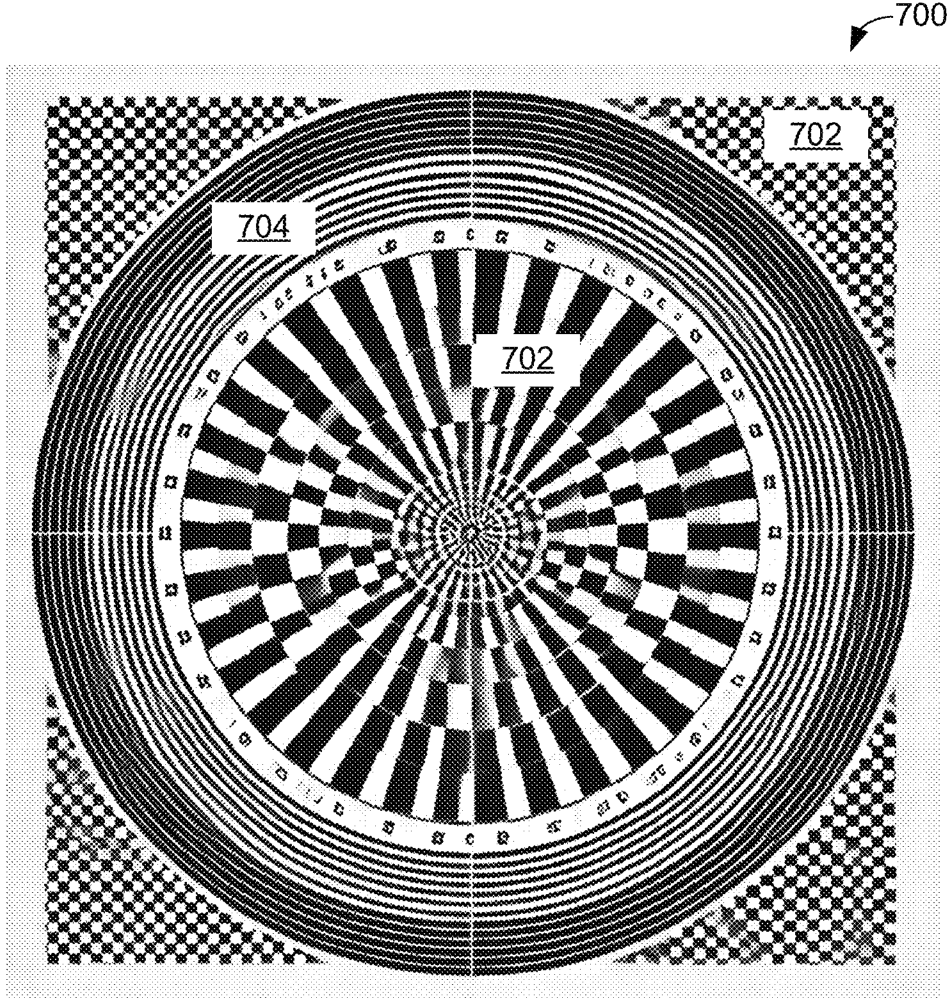
FIG. 7 is another example visual pattern applied to test visual acuity and astigmatism, in accordance with some embodiments.
Figure 8A:
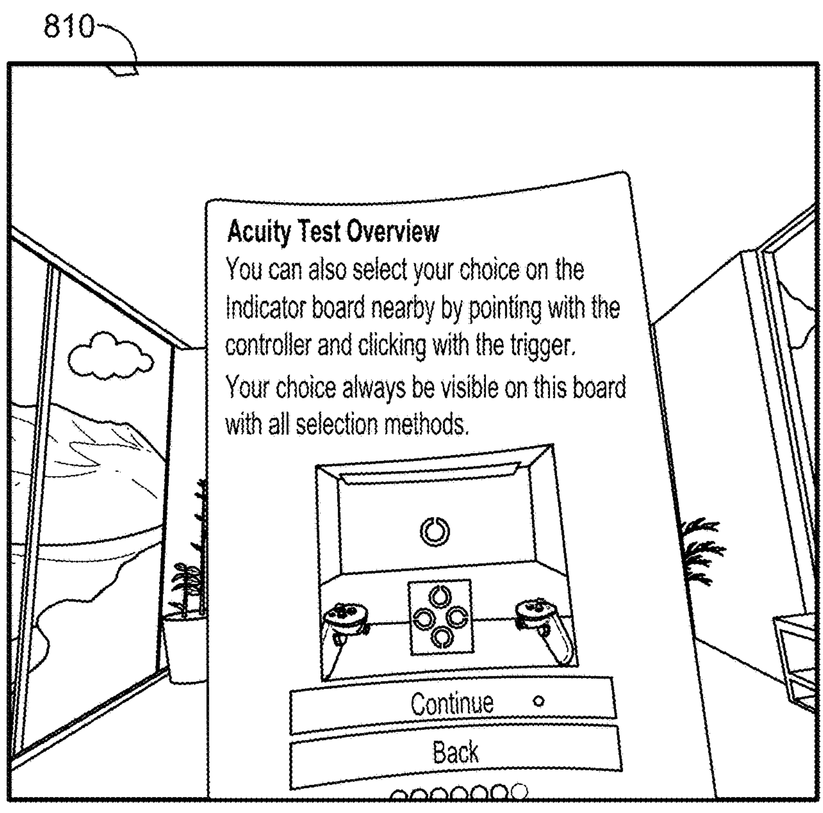
FIGS. 8A-8D include four diagrams of example graphical user interfaces rendered to determine a visual acuity score in a virtual environment created by a headset device, in accordance with some embodiments.
Figure 8B:
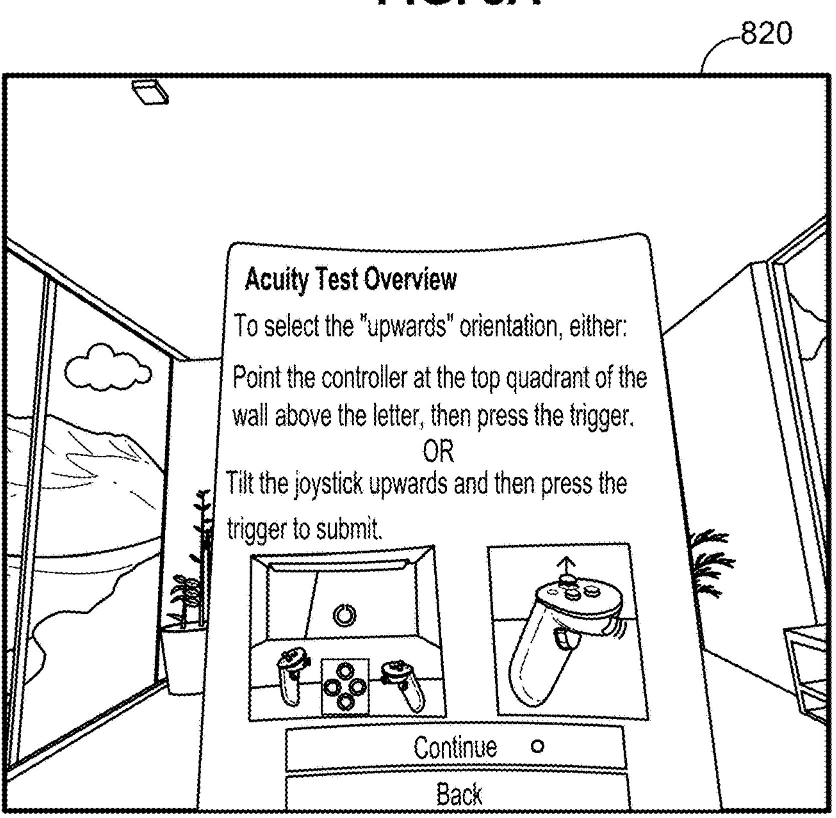
Figure 8C:
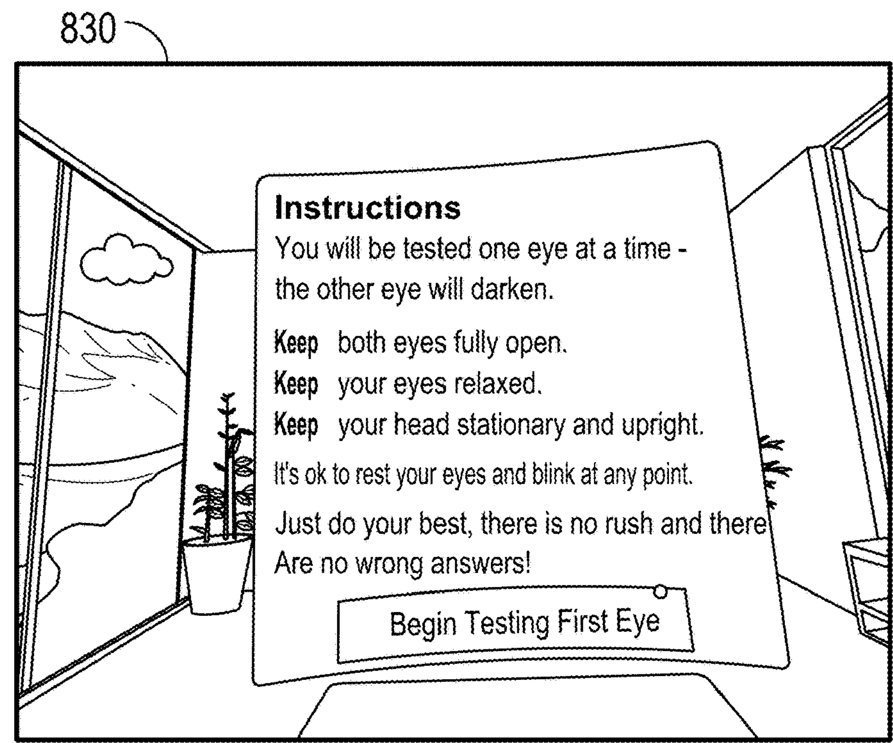
Figure 8D:
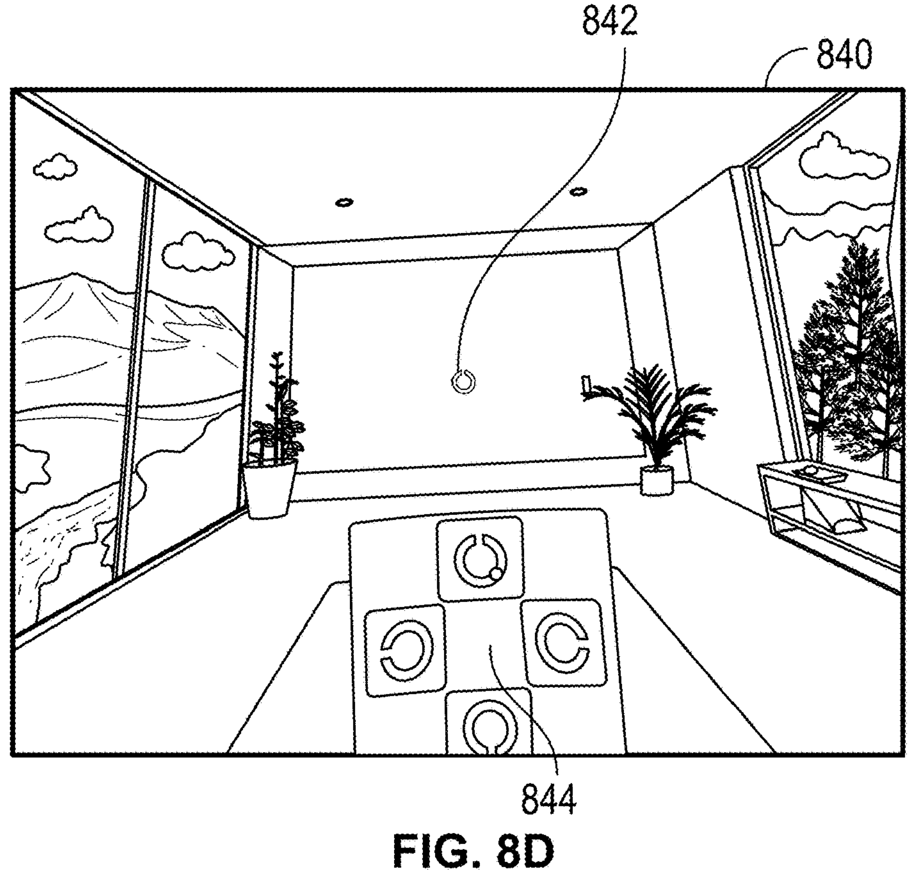

FIG. 7 is another example visual pattern 700 applied to test visual acuity and astigmatism, in accordance with some embodiments. The visual pattern 700 integrates a grid pattern 702 and concentric rings 704. The grid pattern 702 may include evenly spaced horizontal and vertical lines, creating a checkerboard pattern. The grid pattern 702 may be configured to identify distortions in straight lines, which can indicate issues with visual acuity and astigmatism. The concentric rings 704 may expand outward from a center of the visual pattern 700 and can assist in detecting radial distortions, which are common indicators of astigmatism. The visual pattern 700 may be depicted in high-contrast black and white, which ensures maximum clarity and reduces the potential for color-related distortions, making it easier to detect any visual impairment or defect.

FIGS. 8A-8D include four diagrams of example graphical user interfaces 810, 820, 830, and 840 rendered to determine a visual acuity score in a virtual environment created by a headset device 140D, in accordance with some embodiments. The user interface 810 may display an information page including instructions on controlling a headset device 140D to select one of a plurality of optotype candidates to match a target optotype displayed in the virtual environment. The user interface 820 may display an information page including two optional ways of using the controller to select the one of the plurality of optotype candidates. The user interface 830 may display an information page including general guidelines on a visual acuity assessment process. The user interface 840 may display an optotype 842 that is projected on a screen that has a first distance L1 from a user's position in the virtual environment. In a second distance L2 near the user, a selection panel 844 including a plurality of optotype candidates may be displayed, prompting the user to select one of the optotype candidates that matches the optotype 842. In some embodiments, in response to a user selection of the one of the optotype candidates, the optotype 842 displayed in the first distance L1 may be updated with a new optotype 842. Further, in some embodiments, the new optotype 842 may spin at a fast rate for a shortened duration of time (e.g., 2 seconds), before it settles in place of the original optotype 842. In an example, the optotype 842 may spin and gradually shrink in size during the shortened duration of time.

Figure 9A:
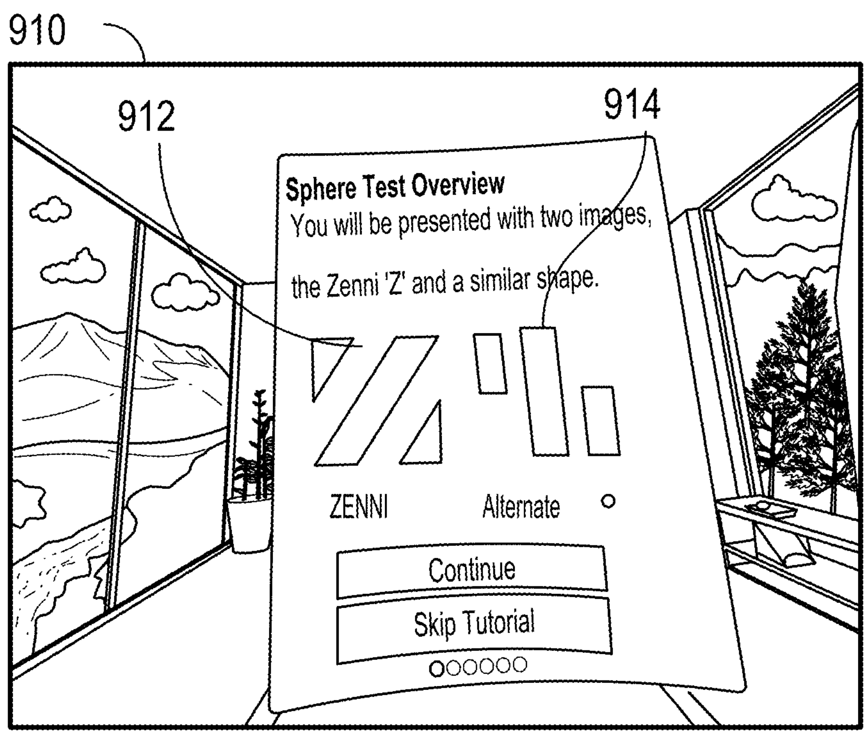
FIGS. 9A-9C include three diagrams of example graphical user interfaces rendered to determine a nearsighted or farsighted power in a virtual environment created by a headset device, in accordance with some embodiments.
Figure 9B:
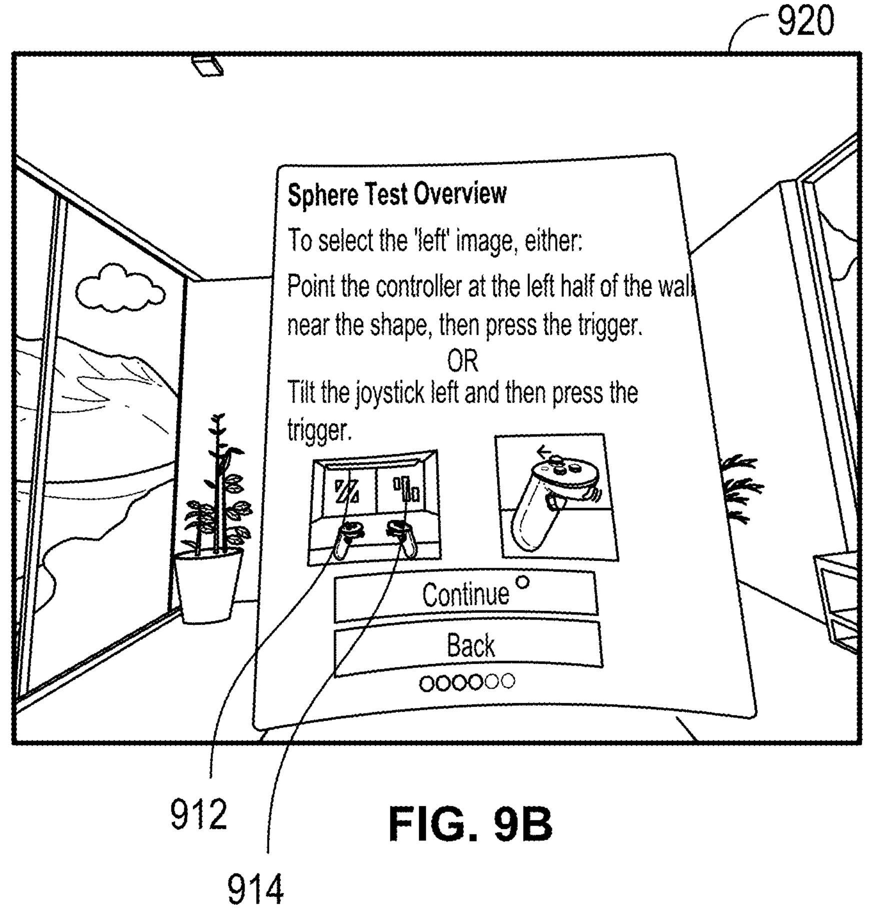
Figure 9C:
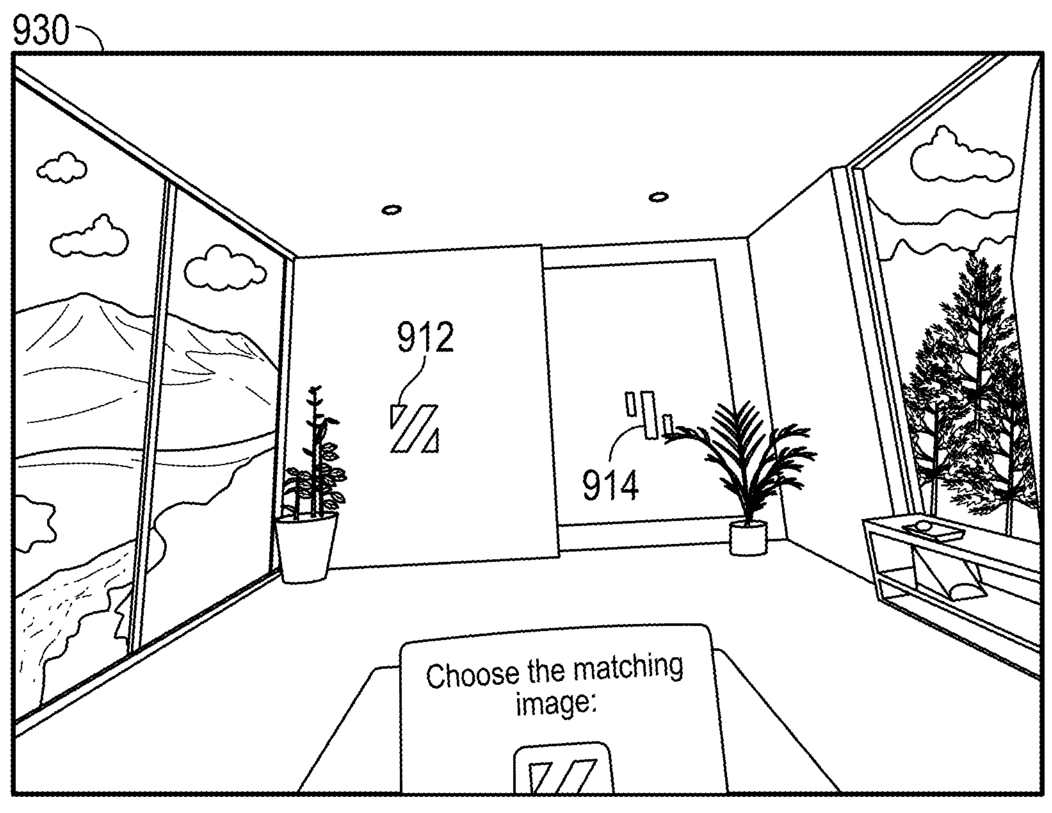

FIGS. 9A-9C include three diagrams of example graphical user interfaces 910, 920, and 930 rendered to determine a nearsighted or farsighted power in a virtual environment created by a headset device 140D, in accordance with some embodiments. The user interface 910 may display an information page explaining that two target optotypes 912 and 914 may be displayed in the virtual environment. The user interface 920 may display an information page including two optional ways of using the controller to select one of the two target optotypes 912 and 914. The user interface 930 may display two target optotypes 912 and 914 that may be projected on a screen that has a first distance L1 from a user's position in the virtual environment. In this example, the target optotype 912 located on the left is highlighted (e.g., by being displayed in a colored background). In a second distance L2 near the user, a confirmation panel 932 may be displayed, prompting the user to select one of the two target optotypes 912 and 914. In some embodiments, in response to a user selection of the one of the two target optotypes 912 and 914, the two target optotypes 912 and 914 displayed in the first distance L1 may be updated with a new pair of two target optotypes 912 and 914. Further, in some embodiments, each optotype 912 or 914 may spin at a fast rate for a shortened duration of time (e.g., 2 seconds), before it settles in place of the original optotype 912 or 914. In an example, the optotype 912 or 914 may spin and gradually shrink in size during the shortened duration of time.

FIGS. 10A-10F include six diagrams of example graphical user interfaces 1010, 1020, 1030, 1040, 1050, and 1060 rendered to determine eye stigmatism in a virtual environment created by a headset device 140D, in accordance with some embodiments. The user interface 1010 may display an information page explaining that a clock diagram of converging numbered lines 1012 (which is a type of optotype) is displayed in the virtual environment. For example, the user interface 1010 may include an message, e.g., "You will be presented with a clock diagram of converging numbered lines." The user interface 1020 may display an information page explaining what is selected on the clock diagram of converging numbered lines 1012 displayed in the virtual environment. For example, the user interface 1010 may include an message, e.g., "Your task is to identify if any of these sets of lines appear clearer, crisper, or darker than other." The user interface 1030 may display an information page including two optional ways of using the controller to select lines on the clock diagram of converging numbered lines 1012. For example, the user interface 1010 may include an message, e.g., "Make a selection by either pointing the controller at the lines on the clock, then pressing the trigger" and "Rotating the joystick to move the indicator arrows around the clock." The user interface 1040 may display an information page illustrating an embodiment having equally clear lines on the clock diagram of converging numbered lines 1012. For example, the user interface 1010 may include an message, e.g., "If two sets of neighboring lines seem to both stand out as equally clear, you can move the indicator arrows to a halfway point between those lines."

Figure 10A:
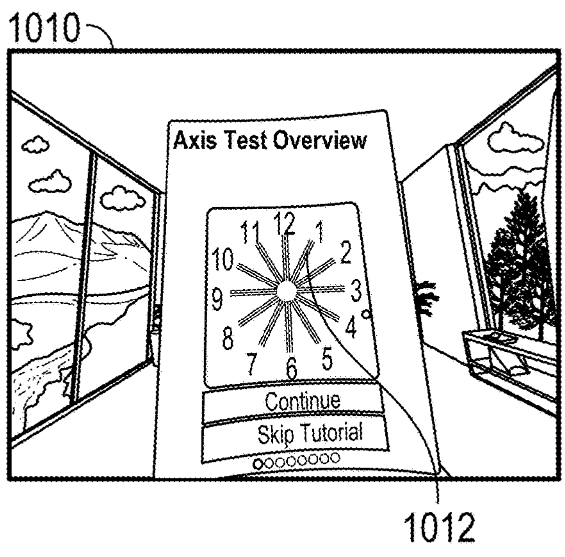
FIGS. 10A-10F include six diagrams of example graphical user interfaces rendered to determine eye stigmatism in a virtual environment created by a headset device, in accordance with some embodiments.
Figure 10B:
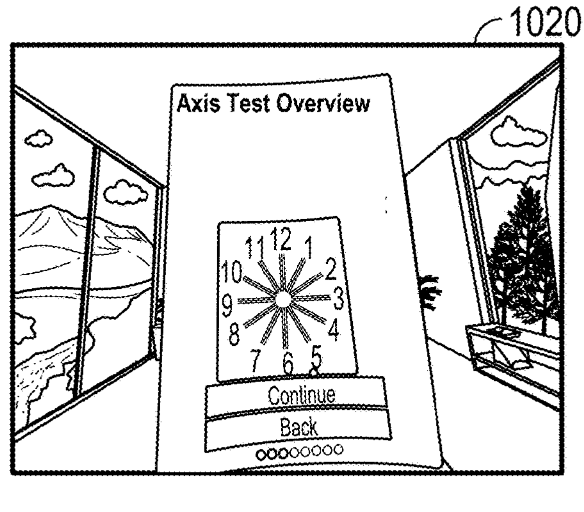
Figure 10C:
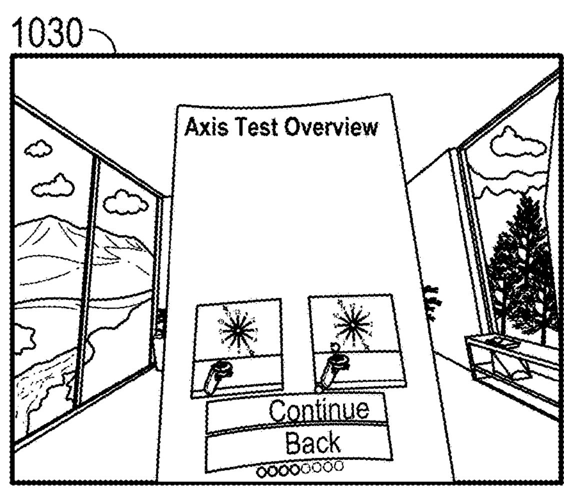
Figure 10D:
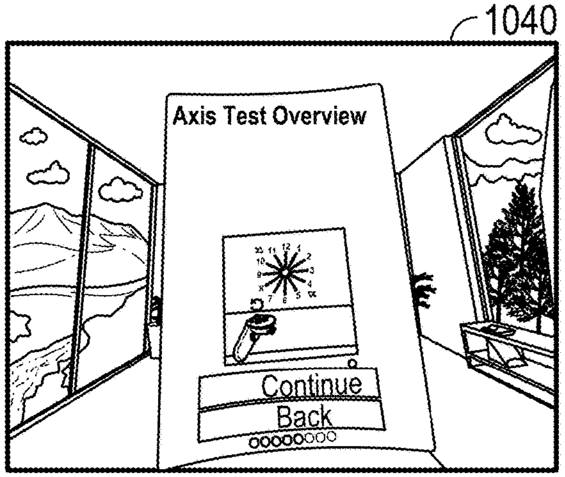
Figure 10E:
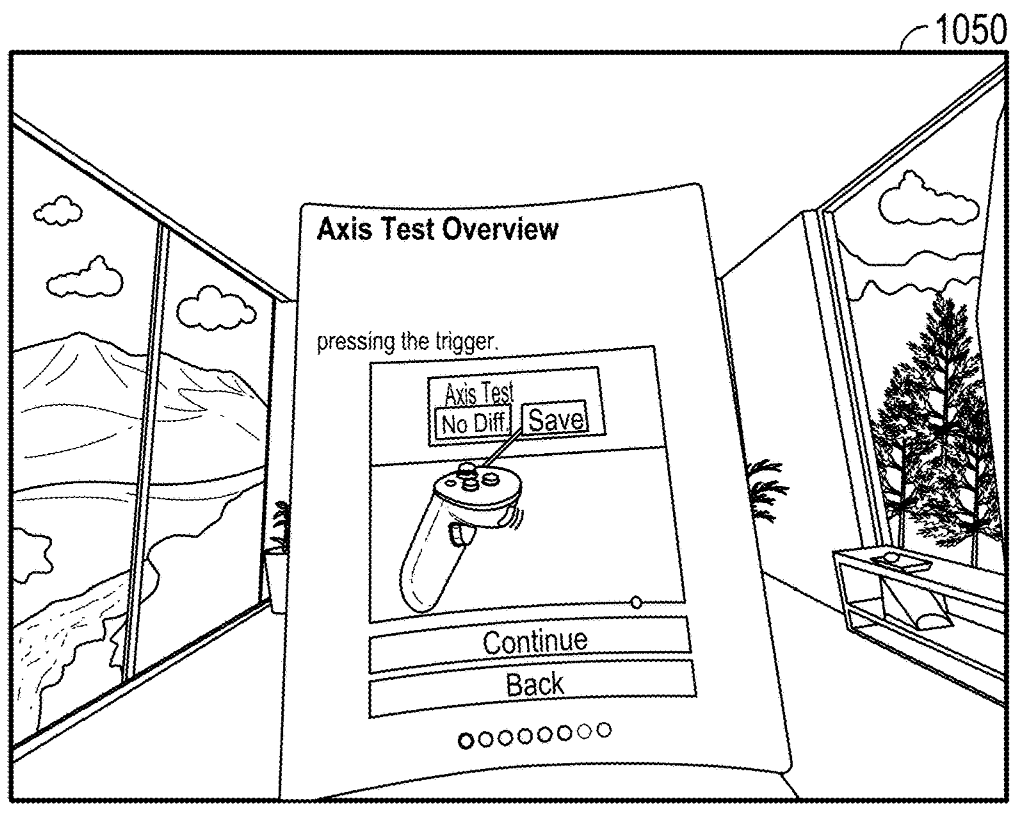
Figure 10F:
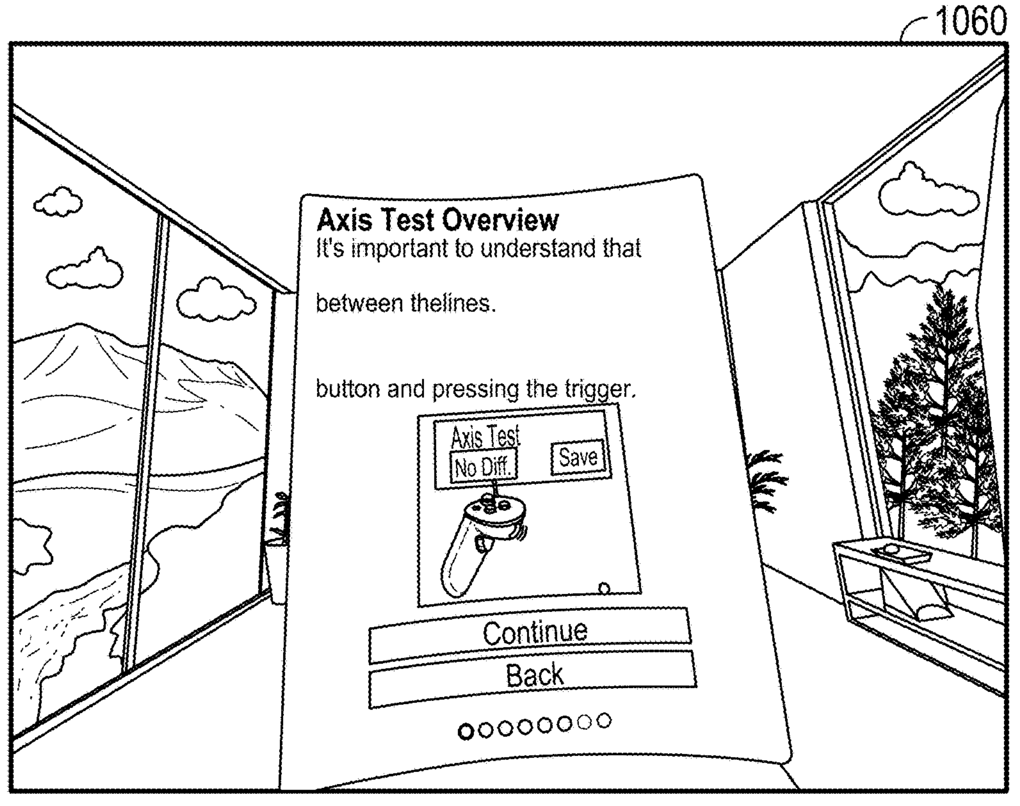

Referring to FIG. 10E, the user interface 1050 may display an information page including an instruction using the controller to submit a selection. For example, the user interface 1010 may include an message, e.g., "After selecting a set of lines, submit your choice with the 'Done' button below by pointing to the controller at the button and pressing the trigger." Further, referring to FIG. 10F, the user interface 1060 may display an information page including an instruction using the controller to indicate that no difference is observed on the clock diagram of converging numbered lines 1012. For example, the user interface 1010 may include an message, e.g., "It's important to understand that not everybody will see a difference between the lines" and "In this case, simply select 'No Difference' below, by positioning the controller at the button and pressing the trigger."

Innovations in Eye Movement Tracking

Some implementations of a VR system may be configured to enhance administration and experience of vision tests. The VR system may include a headset device 140D equipped with a display and one or more sensors for tracking one or more of eye movement, head orientation, and hand gestures of a user wearing the headset device 140D. In some embodiments, the headset device 140D may be configured to execute a vision assessment application 328 configured to adaptively manage a sequence of vision tests based on the user's condition. In some embodiments, the headset device 140D may be communicatively coupled to a server 102 configured to execute a server-side module for the vision assessment application 328, thereby managing the sequence of vision tests jointly with a device-side module the vision assessment application 328 executed on the headset device. The vision assessment application 328 may be configured to generate a virtual reality (VR) user interface corresponding to a three-dimensional (3D) virtual environment and render visual stimuli 338 in this 3D virtual environment. A range of different vision tests may be conducted based on the visual stimuli within an immersive VR space.

In some embodiments, a headset device 140D may include one or more processors 302 and memory 306 storing instructions to execute the vision assessment application 328 for rendering visual stimuli 338 in an output device 312 (e.g., a display) and processing sensor data 342 collected from the sensors 360 in response to the visual stimuli 338. The sensor data 342 may be processed to determine vision test results 344 (e.g., eye movement patterns, response times, and visual perception accuracy) for the user. Further, in some embodiments, VR technology facilitates a personalized control scheme for navigating the vision tests. The personalized control scheme can enable the user to interact with the test environment through intuitive hand gestures and eye movements, thereby providing a natural and engaging testing experience. The vision tests may be customized based on individual users' requirements and accommodate a wide range of vision impairments.

In some embodiments, the vision test results 344 may be used to generate comprehensive reports on the user's visual performance. For example, the headset device 140D may employ a deep learning model that correlates micro-expression data with vision test results 344 to provide holistic assessment of the user's ocular health. In some embodiments, the vision test results 344 may be applied to identify vision conditions of the user and track changes of the vision conditions over time, thereby offering valuable insights to healthcare providers. In some embodiments of the present disclosure, eye images may be captured and used to determine eye movement information automatically and without user intervention, which is an efficient solution to provide reliable supplemental information that cannot be provided by the user's active responses to visual stimuli.

Figure 11:
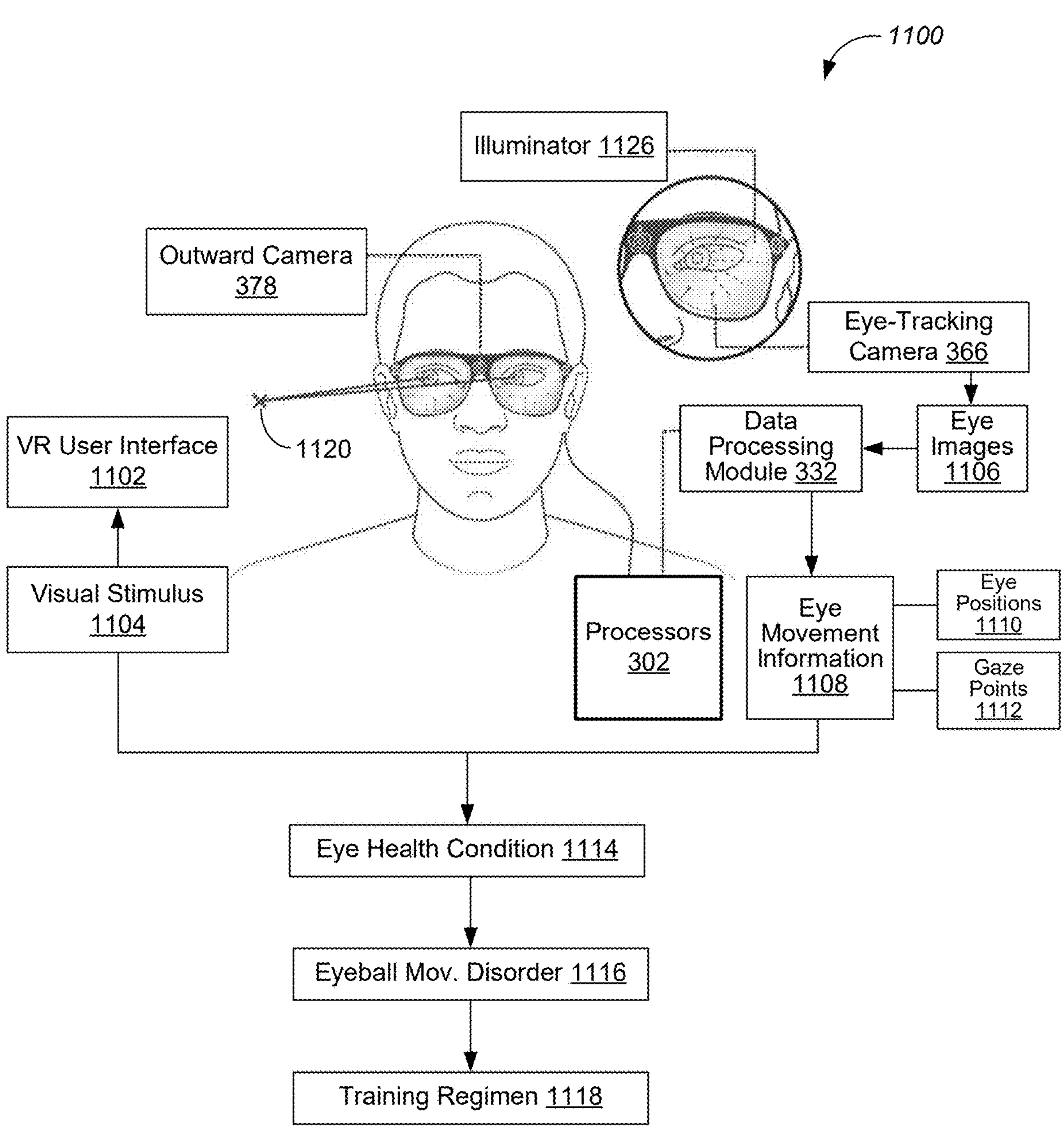
FIG. 11 is a diagram showing a vision test system configured to implement a virtual vision test based on eye tracking, in accordance with some embodiments.

FIG. 11 is a diagram showing a vision test system 1100 configured to implement a virtual vision test based on eye tracking, in accordance with some embodiments. The vision test system 1100 may be implemented using a computer device 140 (e.g., headset device 140D), which may include one or more processors 302, memory 306 storing instructions to be implemented by the processor(s) 302, a head-mounted display (HMD) 312A, and one or more cameras 310A (e.g., outward camera 378, eye-tracking camera 366). The computer device 140 may execute a user application (e.g., a visual assessment application 328) configured to enable the virtual vision test and generates a VR user interface 1102 corresponding to a three-dimensional (3D) virtual environment. A visual stimulus 1104 corresponds to the virtual vision test and is displayed on the user interface 1102. The computer device 140 may focus the eye-tracking camera 366 on an eye area of a user wearing the computer device 140. While displaying the visual stimulus 1104, in real time, the eye-tracking camera 366 can capture a sequence of eye images 1106. The computer device 140 may determine eye movement information 1108 including a temporal sequence of eyeball positions 1110 based on the sequence of eye images 1106. In some embodiments, the eye movement information 1108 may include a temporal sequence of gaze points 1112 each of which corresponds to a respective subset of a subset of eye images 1106. The visual stimulus 1104 and the eye movement information 1108 may be compared to determine an eye health condition.

In some embodiments, the computer device 140 may further include an illuminator 1126 configured to illuminate an eye area covered by the computer device 140 and facilitate capturing the eye images 1106 by the eye-tracking camera 366. Further, in some embodiments, the illuminator 1126 may include a near-infrared diode configured to illuminate the eye area with near-infrared light. The eye-tracking camera 366 may include a near-infrared sensor array.

In some embodiments, a camera 310A of the computer device 140 may be used to capture eyeball movement data that is representative of an eye position 1110. Based on the eyeball movement data, the visual stimulus 1104 and the eye movement information 1108 may be used to determine an eyeball movement disorder 1116. Further, in some embodiments, the computer device 140 (e.g., VR headset device) may focus the camera 310A on an eye area of a user wearing the computer device 140, and displays, on the user interface 1102, a visual stimulus 1104 corresponding to the virtual vision test. While displaying the visual stimulus, in real time, the camera 310A may capture a sequence of eye images 1106.

Examples of the eyeball movement disorder include strabismus (in which two eyes are not directed or focused at the same object), amblyopia (lazy eye), and nystagmus (repetitive eye movements). Strabismus may include esotropia in which either one or both eyes turn in toward the nose, exotropia in which either one or both eyes turn away from the nose, and hypertropia in which one eye is higher than the other. In some embodiments, based on the eye movement disorder 1116, the computer device 140 may prescribe a training regimen 1118 for the eye. Further, in some embodiments, the computer device 140 may display and provide the training regimen 1118 via the VR user interface 1102.

In some embodiments, the visual stimulus 1104 may include a visual pattern 700 (FIG. 7), and may be applied in the vision test system 1100 to monitor the user's gaze point 1120 as the user's eyes interact with the grid 702 and concentric rings 704 of the visual pattern 700. The processors 302 may analyze where the eyes focus and detect discrepancies in tracking, which can be applied to provide detailed data on visual acuity and astigmatism. In some embodiments, eye-tracking can detect subtle changes in how users perceive the visual pattern 700, providing real-time feedback on potential visual issues (e.g., the eye health condition 1114) and helping create personalized correction plans or further diagnostic procedures.

Figure 12:
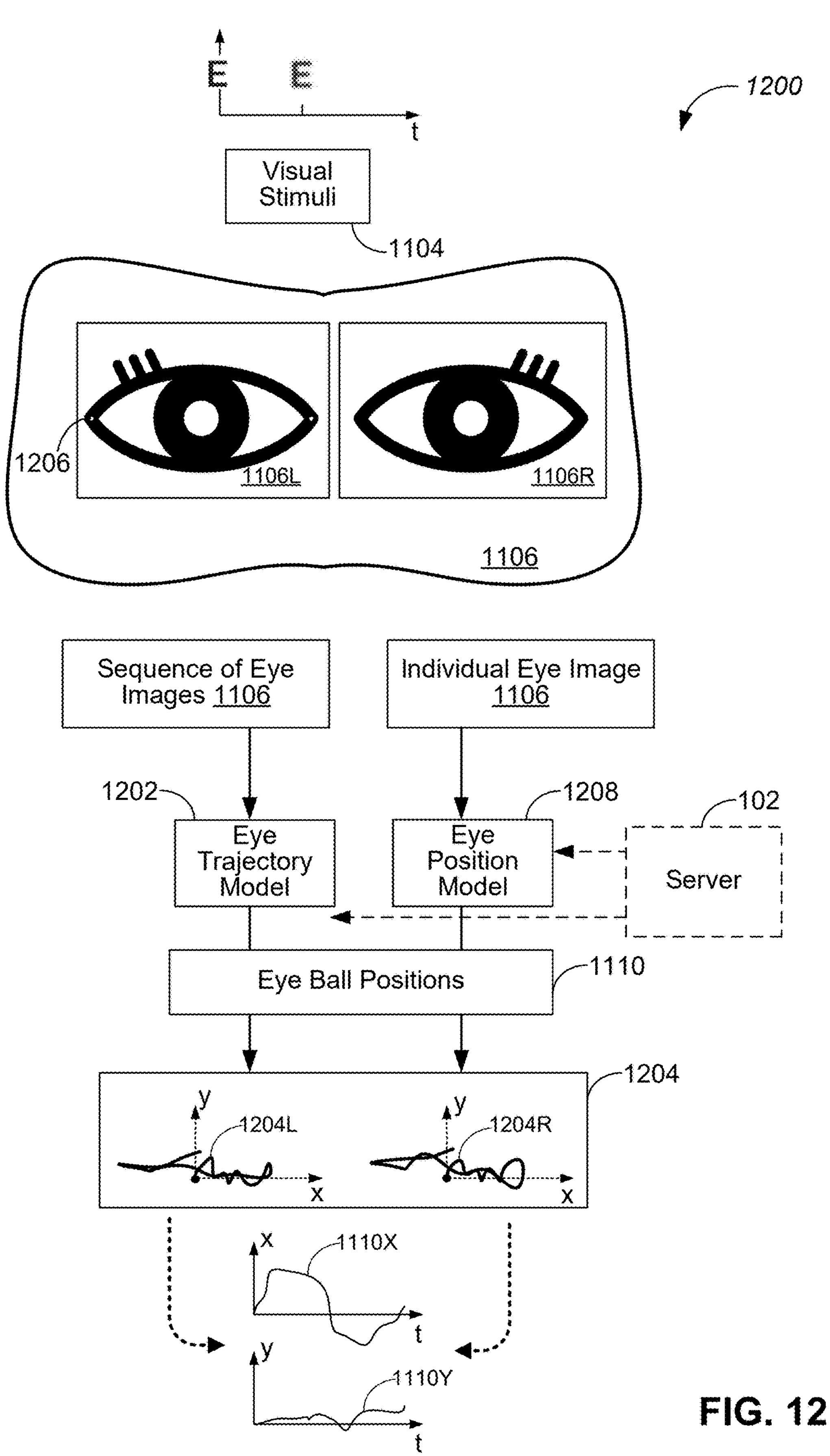
FIG. 12 is a flow diagram of an example method of tracking eyes for vision test, in accordance with some embodiments.

FIG. 12 is a flow diagram of an example method 1200 of tracking eyes for vision test, in accordance with some embodiments. A computer device 140 (e.g., headset device 140D) may include a head-mounted display (HMD) 312A, and one or more cameras 310A (e.g., outward camera 378 and eye-tracking camera 366 in FIG. 3). The computer device 140 may execute a user application (e.g., a visual assessment application 328) configured to enable the virtual vision test and generate a VR user interface 1102 (FIG. 11) corresponding to a 3D virtual environment. A visual stimulus 1104 (FIG. 11) corresponds to the virtual vision test, and is displayed on the user interface 1102. The computer device 140 may focus the eye-tracking camera 366 on an eye area of a user wearing the computer device 140. While displaying the visual stimulus 1104, in real time, the eye-tracking camera 366 may capture a sequence of eye images 1106 (FIG. 11), which is applied to determine eye movement information 1108 including a temporal sequence of eyeball positions 1110. In some embodiments, for each of the sequence of eye images 1106, the computer device 140 may crop the respective eye image 1106 to generate a left eye image 1106L and/or a right eye image 1106R including a respective eye of the user based on a predefined aspect ratio. After cropping, a resolution of the respective eye image 1106 may be adjusted to a predefined resolution.

In some embodiments, the computer device 140 may apply an eye trajectory model 1202 to process the sequence of eye images 1106 (FIG. 11) jointly and identify an eyeball position trajectory 1204 including the temporal sequence of eyeball positions 1110. In some embodiments, the eyeball position trajectory 1204 may include a first trajectory 1204L of a left eye or a second trajectory 1204R of a right eye. For either eye, the respective trajectory 1204L or 1204R may include a respective temporal sequence of x positions 1110X and a respective temporal sequence of y positions 1110Y. Alternatively, in some embodiments, an eye position model 1208 may be applied to process each of the sequence of eye images 1106 and identify a respective eyeball position 1110 in each eye image 1106. Respective eyeball position 1110 of the sequence of eye images 1106 may be consolidated to the temporal sequence of eyeball positions 1110. Additionally, in some embodiments, the computer device 140 may obtain the eye trajectory model 1202 or the eye position model 1208 from a server 102, and the server 102 is communicatively coupled to the computer device 140 via one or more communication networks 108 and is configured to manage the user application 324 and a plurality of user accounts.

In some embodiments, the server 102 may obtain a plurality of test eye images and associated ground truth eyeball positions. The eye trajectory model 1202 or the eye position model 1208 may be trained with the plurality of test eye images and the associated ground truth eyeball positions. After training, the server may send the eye trajectory model 1202 or the eye position model 1208 to the computer device 140.

In some embodiments, for each of the sequence of eye images 1106, the computer device 140 may process the respective eye image 1106 to identify one or more reference locations 1206 (e.g., a tear duct located at a corner of eye, an upper lash line, a lower lash line, an outer V). A respective eyeball position 1110 may be determined with respect to the one or more reference locations 1206. For example, for either eye, a reference location 1206 of an eye coordinate system may be set a middle point of a line connecting the tear duct and the outer V of the respective eye, and the respective eyeball position 1110 may include an x-axis position 1110X and a y-axis position 1110Y measured with respect to the reference location 1206 (which corresponds to an origin of the eyeball position trajectory 1204.

Figure 13:
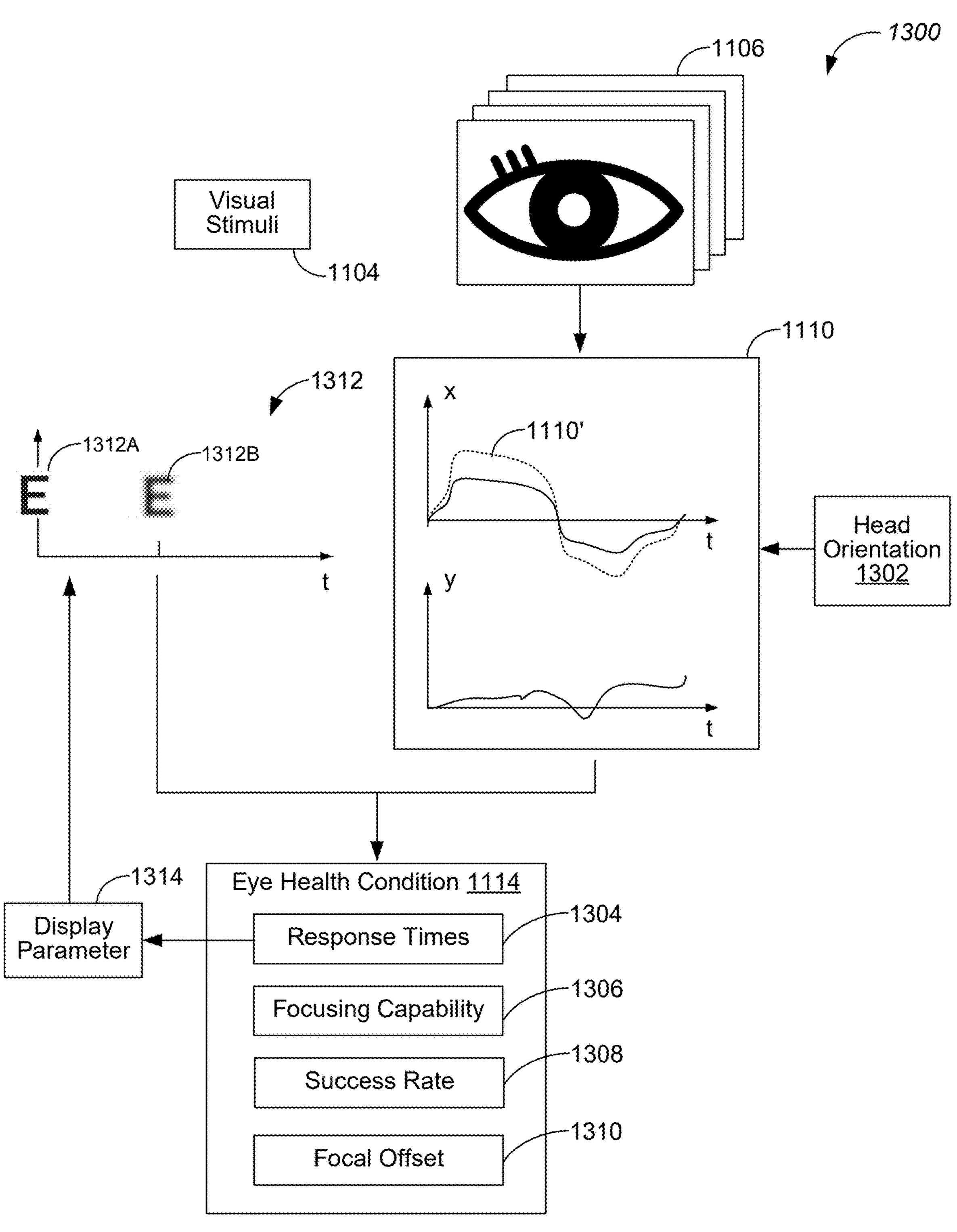
FIG. 13 is a flow diagram of an example method of tracking eyes for vision test, in accordance with some embodiments.

FIG. 13 is a flow diagram of an example method 1300 of tracking eyes for vision test, in accordance with some embodiments. In some embodiments, for each of the sequence of eye images 1106, the computer device 140 may further determine a respective head orientation 1302, and adjust the respective eyeball position 1110 based on the respective head orientation 1302, generating the adjusted respective eyeball position 1110'. For example, the user wearing the computer device 140 may only turn around his or her head without lifting up or down the head. The x-axis eyeball position corresponding to the adjusted respective eyeball position 1110' may deviate from the x-axis eyeball position 1110X, and the y-axis eyeball position corresponding to the adjusted respective eyeball position 1110' may be negligible.

In some embodiments, the visual stimulus 1104 and the eye movement information 1108 (e.g., eyeball positions 1110) may be compared to generate a comparison result including one or more of: an eyeball response time 1304, a success rate 1308, an eyeball position trajectory 1204, whether an eyeball focuses (i.e., a focusing capability 1306), or an offset 1310 from a correct focal point. In some embodiments, the eye health condition may include an eye's focusing capability 1306. In response to the visual stimulus 1104 staying at a fixed position on the user interface 1102, the computer device 140 may determine that the temporal sequence of eyeball positions 1110 follows the visual stimulus 1104 and moves around within a positional range around an eye position. The eye's focusing capability 1306 may be determined based on the positional range. In accordance with a determination that the positional range exceeds a vibration tolerance, the computer device 140 may determine an eyeball movement disorder 1116 (FIG. 11) corresponding to a difficult in focusing on the visual stimulus 1104.

In some embodiments, in response to the visual stimulus 1104, the computer device 140 may determine one or more response times 1304 associated with the temporal sequence of eyeball positions 1110. Based on the one or more response times, the computer device 140 may determine whether the eye health condition 1114 of the user may include a predefined neurological defect. For example, in accordance with a determination that the one or more response times 1304 are greater than a response time threshold, the computer device 140 may determine that the predefined neurological defect causes an abnormal delay for the user's eye to respond to the virtual stimulus 1104.

In some embodiments, the visual stimulus 1104 may include a sequence of optotypes 1312. In response to the visual stimulus, the computer device 140 may determine a success rate 1308 of the temporal sequence of eyeball positions 1110 following each of the sequence of optotypes 1312. The eye health condition 1114 of the user may be determined based on the success rate 1308. Further, in some embodiments, a false positive rate, a false negative rate, or both of them of the eyeball positions 1110 may be determined, e.g., for diagnosis of an eyeball movement disorder 1116 clinically.

In some embodiments, the visual stimulus 1104 may include a sequence of optotypes 1312. The computer device 140 may determine one or more response times 1304 associated with a first subset of the temporal sequence of eyeball positions 1110, which are associated with a first subset of optotypes 1312A. Based on the one or more response times, the computer device 140 dynamically adjusts a display parameter 1314 of a second subset of optotypes 1312B following the first subset of optotypes 1312A. Further, in some embodiments, the display parameter 1314 of the second subset of optotypes 1312B may include one or more of a display size, a spatial pitch, a temporal pitch, a contrast level, and a brightness level of the second subset of optotypes 1312B.

Figure 14:
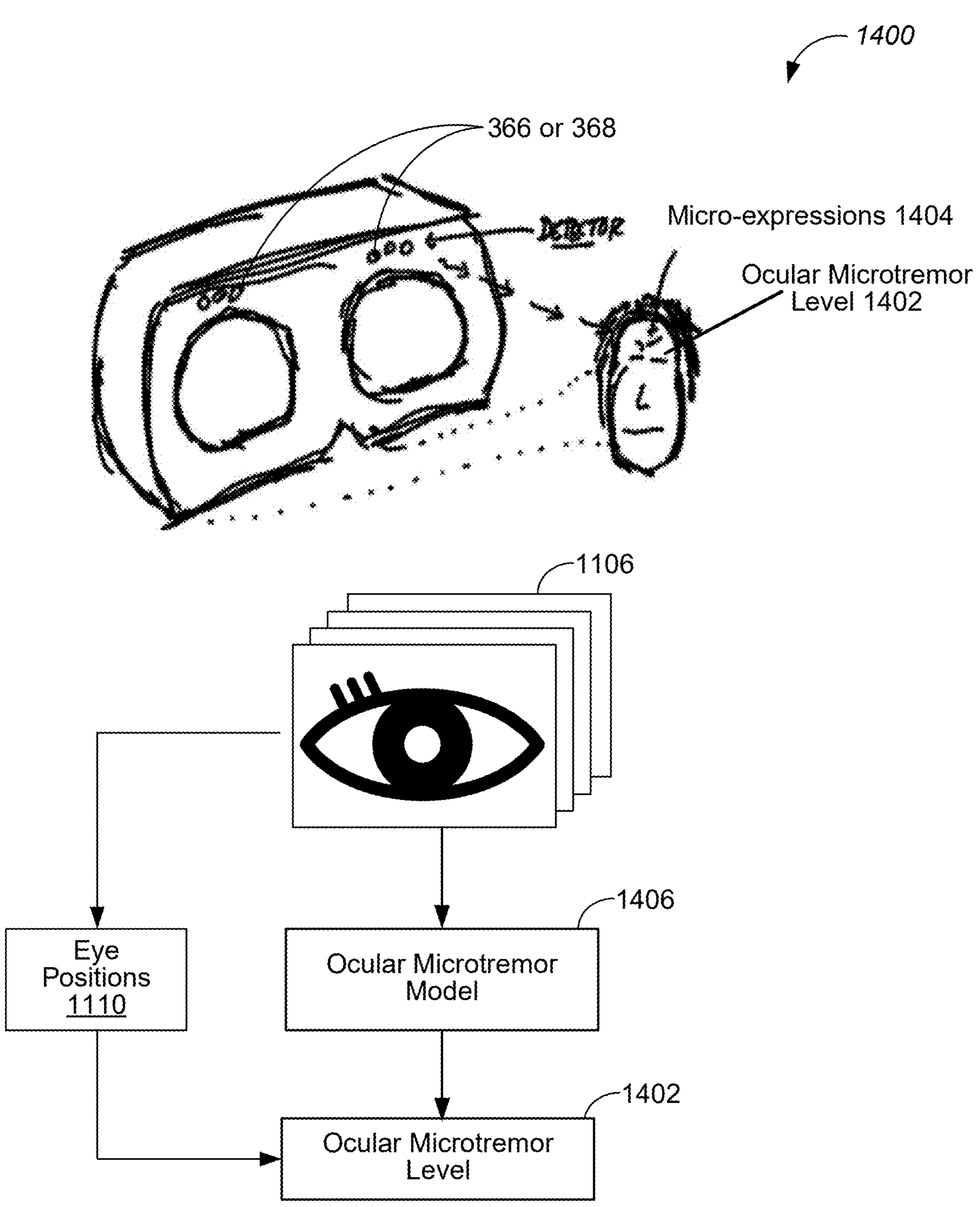
FIG. 14 is a diagram illustrating an example method of tracking micro-expressions and microtremors in an eye area, in accordance with some embodiments.

FIG. 14 is a diagram illustrating an example method 1400 of tracking micro-expressions and microtremors in an eye area, in accordance with some embodiments. In some embodiments, one or more the sequence of eye images 1106 may be processed to identify an ocular microtremor level or micro-expression in the eye area. In other words, a subarea of the eye area does not correspond to an eyeball, and a subset of a respective eye image 1106 may be analyzed to determine the ocular microtremor level 1402 or a micro-expression 1404 (e.g., frowning). In some embodiments, the sequence of eye images 1106 may be analyzed to determine one or more parameters of: a left-right asymmetry, a velocity of facial muscle movement in the subarea of the eye area, and an eye blinking rate. The micro-expression 1404 may be further determined based on the one or more parameters, e.g., using a corresponding machine learning model 350. In an example, a patient may have an eye health condition 1114 causing an apraxia of lid opening. The computer device 140 may determine a level of the left-right asymmetry based on the sequence of eye images 1106. The computer device 140 can also compare the level of the left-right asymmetry with historical levels of the left-right asymmetry to determine whether the eye health condition causing an apraxia of lid opening deteriorates over time.

In some embodiments, the eye-tracking camera 366 of the headset device 140D (FIG. 3) may be configured to detect micro-expressions and ocular microtremors. Alternatively, in some embodiments, the headset device 140D may further include a biometric sensor array 368 (FIG. 3) configured to detect micro-expressions and ocular microtremors. The biometric sensor array 368 may provide a higher resolution than the eye-tracking camera 366. The biometric sensor array 368 may be configured to generate biometric data used in diagnosis of early-stage neurological disorders and ocular diseases. Further, in some embodiments, an ocular microtremor model 1406 may be applied to process the sequence of eye images 1106 jointly and identify an ocular microtremor level 1402. Alternatively, in some embodiments, an ocular microtremor level 1402 may be determined based on the temporal sequence of eyeball positions 1110.

Innovations in Automatic Neurological Feedback

Development of VR technology that integrates multiple vision testing methods presents a significant advancement in comprehensive vision assessments. Some embodiments of the present disclosure are directed to a VR system configured to conduct a wide array of vision tests within a single immersive environment. This system may include a VR headset equipped with sensors 360 (FIG. 3) and output devices 312 (e.g., displays), capable of delivering visual stimuli and capturing user responses. The VR headset may be coupled to a computer device (e.g., a server 102) that runs a suite of visual assessment application 328 (FIG. 3). The visual assessment application 328 can be configured to implement a range of vision tests, including but not limited to visual acuity test, color perception test, depth perception test, and peripheral vision test. The VR system can be configured to integrate these vision tests, allowing users to undergo thorough evaluation of their visual capabilities in a seamless and integrated manner. In some embodiments, each test may be dynamically adapted to a user's specific vision profile, thereby providing personalized and precise assessment.

In some embodiments, a headset device 140D may include one or more processors 302 and memory 306 storing instructions to execute the vision assessment application 328 for rendering visual stimuli 338 in an output device 312 (e.g., a display) and processing sensor data 342 collected from the sensors 360 in response to the visual stimuli 338. The sensor data 342 may be processed to determine vision test results 344 (e.g., eye movement patterns, response times, and visual perception accuracy) for the user. Further, in some embodiments, the VR system may incorporate an advanced neuro-ocular interface that monitors real-time neural activity associated with visual processing. This interface may utilize non-invasive neural sensors embedded in the VR headset, capable of capturing subtle brain wave patterns and neural responses to visual stimuli. For example, electrodes may be integrated in one or more head straps of a headset device 140D for recording neurological signals of a brain of a user wearing the headset device 140D.

Data analysis algorithms (e.g., machine learning models 350) may be employed to interpret data collected by neural sensors and provide unprecedented insights into the user's overall visual health. For example, a specialized neural network may be applied to correlate neural activity patterns with visual performance metrics. The data analysis algorithm may allow for identification of a wide range of vision issues and early detection of neurological conditions affecting vision. The vision issues identified by data analysis can range from common refractive errors to more complex visual disorders. In some embodiments, the headset device 140D may be communicatively coupled to one or more servers 102, and enable a centralized vision test management platform with the one or more servers 102. This platform can aggregate data across multiple users, facilitating large-scale research and analysis. Further, in some embodiments, the platform's architecture may include a real-time adaptive feedback system that adjusts vision tests dynamically based on neural and ocular data and ensures personalized and optimized testing conditions for each user.

The headset device 140D may be configured to integrate multiple vision testing methods, advanced neural monitoring, and real-time adaptive feedback into a single, secure, and interactive VR environment. This can significantly enhance the scope, accuracy, and user experience of vision assessments, improve individual diagnostic capabilities, and contribute to broader research efforts in understanding the complex interplay between neural activity and visual health. In some embodiments of the present disclosure, neural activities may be captured and used to determine user spontaneous responses to visual stimuli automatically and without user intervention, which is an efficient solution to provide reliable supplemental information that cannot be provided by the user's active responses to visual stimuli.

Figure 15:
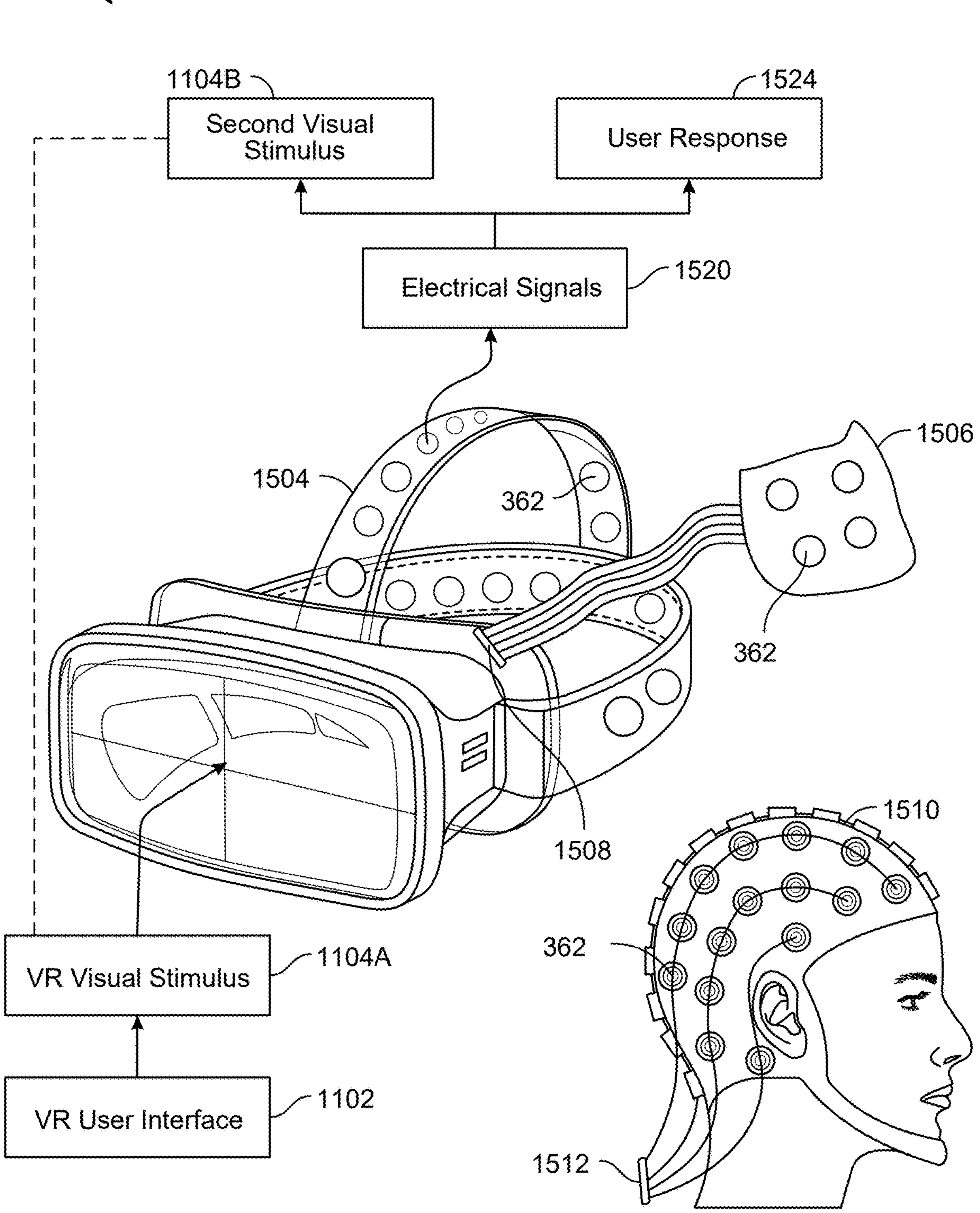
FIG. 15 is a diagram illustrating a headset device including a plurality of electrodes for measuring neural responses to visual stimuli, in accordance with some embodiments.

FIG. 15 is a diagram illustrating a headset device 140D including a plurality of electrodes for measuring neural responses to visual stimuli, in accordance with some embodiments. A computer device 140 (e.g., the headset device 140) may include one or more processors 302, memory 306 storing instructions to be implemented by the processor(s) 302, a head-mounted display (HMD) 312A, and one or more cameras 310A (e.g., outward camera 378, eye-tracking camera 366). The computer device 140 may execute a user application 324 (e.g., a visual assessment application 328) configured to enable a virtual vision test and generate a VR user interface 1102 corresponding to a 3D virtual environment. A first visual stimulus 1104A can correspond to the virtual vision test, and is displayed on the user interface 1102. The computer device 140 may include a plurality of electrodes 362. While displaying the first visual stimulus 1104A, in real time, the electrode device 200 can collect a plurality of electrical signals 1520 by the plurality of electrodes 362 that contact a head of a user of the computer device 140, and determine a second visual stimuli 1104B or a user response 1524 (e.g., spontaneous neural response) to the first visual stimulus 1104A based on the plurality of electrical signals 1520.

In some embodiments, the plurality of electrodes 362 may be integrated on one or more head straps 1504 of the computer device 140. The electrodes 362 integrated on the one or more head straps 1504 may be exposed to air, and when a user wears the computer device 140, the electrodes 362 come into contact with scalp of the head of the user. Alternatively, in some embodiments, the plurality of electrodes 362 may be integrated on an electrode pad 1506 electrically coupled to a body of the headset device 140D via a headset connector 1508. The electrode pad 1506 may be detachable from the body of the headset device 140D. Additionally, in some embodiments, the electrode pad 1506 may include a hat 1510 having an inner surface integrated with the plurality of electrodes 362. The electrodes 362 may be exposed to air via the inner surface of the hat 1510. When the user wears the computer device 140, the electrodes 362 may come into contact with scalp of the head of the user. The plurality of electrodes 362 of the hat 1510 may be coupled to an electrode connector 1512, which is configured to couple to the headset connector 1508, allowing the plurality of electrodes 362 to be controlled by the one or more processors 302 of the headset device 140D.

In some embodiments, the visual stimulus 1104A may include a visual pattern 700 (FIG. 7). The headset device 140D may monitor brain activity via electrodes 362 (also called EEG (electroencephalogram) sensors) when a user views the visual pattern 700. Changes in brain wave patterns can indicate how the user's brain processes the visual pattern 700 and identify any anomalies related to visual acuity, astigmatism, or both. The EEG sensors can help correlate visual distortions with specific brain activity patterns, understand cognitive aspects of visual impairments, and develop effective treatment strategies.

Figure 16:
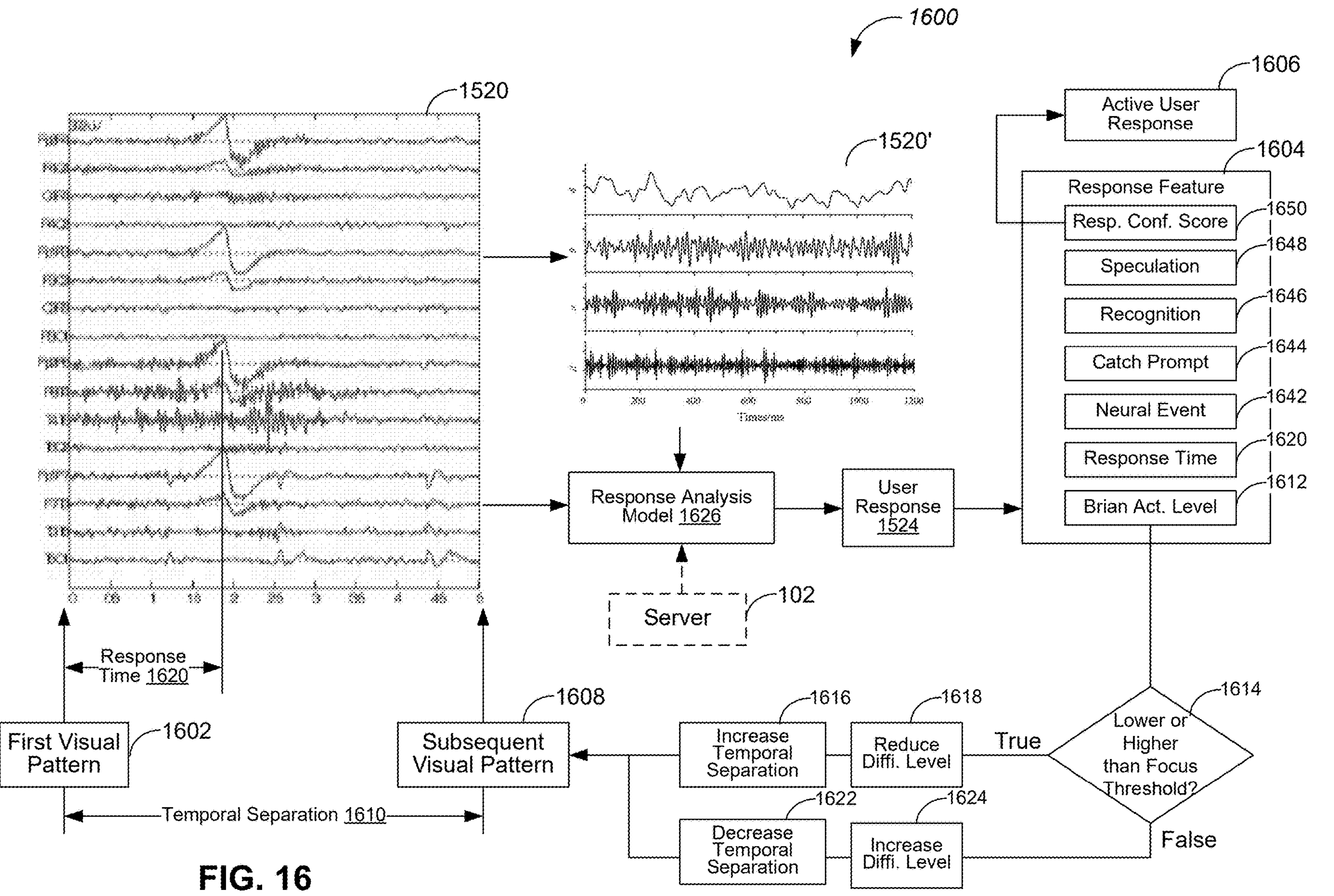
FIG. 16 is a diagram showing an example vision test system configured to facilitate a virtual vision test based on neural signals, in accordance with some embodiments.

FIG. 16 is a diagram showing an example vision test system 1600 configured to facilitate a virtual vision test based on neural signals, in accordance with some embodiments. The vision test system 1600 may include a computer device 140 (e.g., headset device 140D). The computer device 140 may further include one or more processors 302, memory 306 storing instructions to be implemented by the processor(s) 302, a head-mounted display (HMD) 312A, a plurality of electrodes 362. The computer device 140 may execute a user application (e.g., a visual assessment application 328) configured to enable the virtual vision test and generates a VR user interface 1102 corresponding to a 3D virtual environment. While displaying a first visual stimulus 1104A, in real time, the electrode device 200 may collect a plurality of electrical signals 1520 by the plurality of electrodes 362, and determine information of a next visual stimulus 1104N following the first visual stimulus 1104A or a user response 1524 to the first visual stimulus 1104A based on the plurality of electrical signals 1520.

In some embodiments, the plurality of electrodes 362 may be configured to form an electroencephalography (EEG) sensor system, and the plurality of electrical signals 1520 have a temporal resolution of milliseconds (ms). The plurality of electrodes may directly track the electrical activity of brain cells by measuring their effects on the electrical fields just outside the head of the user. In an example, each electrical signal 1520 collected by a respective electrode 362 may be sampled at a sampling rate at 1-10 KHz. Locations of the plurality of electrodes 362 may correspond to one or more regions of interest (ROI) in the brain.

In some embodiments, the first visual stimulus 1104A may include a first visual pattern 1602, and correspond to a temporal sequence of visual patterns. The virtual vision test may be one of a visual acuity test, a visual field test, a visual depth test, a color blindness test, a retinoscopy, a refraction test, an astigmatism test, and a contact lens exam. The first visual pattern 1602 may be selected from a plurality of predefined visual patterns to implement the virtual vision test, and be configured to be displayed with one or more adjustable display parameters 1314 (e.g., a display size, a spatial pitch, a temporal pitch, a contrast level, and a brightness level).

While displaying the first visual pattern 1602, the computer device 140 may determine a response feature 1604 of the user response 1524 to the first visual pattern 1602 based on the plurality of electrical signals 1520. In some embodiments, the response feature 1604 of the user response 1524 to the first visual stimulus 1104A may be determined based on the plurality of electrical signals 1520. The response feature 1604 may include one or more of: a brain activity level 1612, a response time 1620, whether each of one or more feature neural events 1642 occurs, whether the user catches a prompt 1644, or whether the user has a recognition 1646 or speculation 1648 about the first visual stimulus 1104A. The response feature 1604 may reflect a spontaneous neural response to the first visual pattern 1602. In some embodiments, based on the response feature 1604, a subsequent visual pattern 1608 immediately following the first visual pattern 1602 may be dynamically selected, and a next temporal separation 1610 may be determined to separate the first visual pattern 1602 and the subsequent visual pattern 1608. The subsequent visual pattern 1608 corresponds to the second visual stimulus 1104B Further, in some embodiments, the response feature may include a brain activity level 1612. In accordance with a determination (operation 1614) that the brain activity level 1612 is lower than a focus threshold, the next temporal separation 610 may be increased (operation 1616), giving more time to the user to respond, compared with a current temporal separation between the first visual pattern 1602 and a previous visual pattern (not shown in FIG. 16). Alternatively, in accordance with a determination (operation 1614) that the brain activity level 1612 is lower than the focus threshold, a difficulty level of the subsequent visual pattern 1608 may be reduced (operation 1618) compared with that of the first visual pattern 1602, e.g., using a simpler visual pattern 1608. Conversely, in some embodiments, in accordance with a determination (operation 1614) that the brain activity level 1612 is higher than the focus threshold, the next temporal separation 610 may be decreased (operation 1622) compared with a current temporal separation between the first visual pattern 1602 and a previous visual pattern (not shown in FIG. 16), shortening a length of time for the user to respond to the subsequent visual pattern 1608. Alternatively, in accordance with a determination (operation 1624) that the brain activity level 1612 is higher than the focus threshold, the difficulty level of the subsequent visual pattern 1608 may be increased (operation 1618) compared with that of the first visual pattern 1602, e.g., using more complicated visual pattern 1608.

In some embodiments, the response feature 1604 may include a response time 1620 determined based on the plurality of electrical signals 1520 measured by the plurality of electrodes 362 (e.g., not based on an active user response 1606). In accordance with a determination that the response time 1620 is greater than a response threshold, the next temporal separation 1610 may be increased compared with a current temporal separation between the first visual pattern 1602 and a previous visual pattern. Alternatively, in accordance with a determination that the response time 1620 is greater than a response threshold, a difficulty level of the subsequent visual pattern 1608 may be reduced compared with that of the first visual pattern 1602.

In some embodiments, the computer device 140 (e.g., a headset device 140D) may apply a response analysis model 1626 to process a subset of the plurality of electrical signals 1520, which is recorded immediately after a first visual pattern 1602, and determine the user response 1524 (e.g., including one or more of the response features 1604) to the first visual pattern 1602. In an example, the user response 1524 may include whether the user speculates about the first visual pattern 1602 (e.g., one of a recognition 1646 and a speculation 1648). Further, in some embodiments, the virtual vision test may include a color vision test, and the first visual pattern 1602 is applied in the color vision test to evaluates whether there are difficulties distinguishing between different colors. The user response 1524 to the color vision test may be automatically determined from the plurality of electrical signals 1520 without user intervention. Stated another way, the user response 1524 may include the user's uncontrollable and spontaneous response to the first visual pattern 1602.

In some embodiments, the plurality of electrical signals 1520 may be preprocessed before the response analysis model 1626 to process the subset of the plurality of electrical signals 1520. For example, the plurality of electrical signals 1520 may be denoised, down-sampled, smoothed, and/or scaled to generate modified electrical signals, which may be further provided as input to the response analysis model 1626. In some embodiments, the plurality of electrical signals 1520 may be converted to a plurality of brainwaves 1520' (e.g., Delta (±0 to 4 Hz), theta (4-8 Hz), alpha (8-13 Hz), and beta (13-20 Hz)), and the plurality of brainwaves 1520' may be further processed by the response analysis model 1626, e.g., for extracting one or more response features 1604.

In some embodiments, the user response 1524 may include an active user response 1606 sensed by an alternative sensor 360 (e.g., a camera, a microphone) distinct from the electrodes 362. Examples of the active user response include, but are not limited to, head nodding, a hand gesture, and a voice indicator. The active user response may indicate an optotype displayed on the user interface 1102 or confirm whether the user recognizes a visual pattern. The active user response 1606 to a first visual pattern may be collected using a microphone or a camera of the computer device 140. A response analysis model 1626 may be applied to process a subset of the plurality of electrical signals 1520, which is recorded immediately after the first visual pattern 1602. A confidence score associated with the active user response 1606 may be generated. In other words, in some embodiments, if the active user response 1606 matches the electrical signals 1520, the confidence score 1650 may be high (e.g., greater than 0.8 in a range of 0-1), and if the active user response 1606 does not match the electrical signals 1520, the confidence score 1650 may be reduced.

In some embodiments, the response analysis model 1626 may be received from a server 102 (FIG. 1) associated with the computer device 140. The response analysis model 1626 may be applied to process the plurality of electrical signals 1520, thereby determining information of at least one of the subsequent visual pattern 1608 or the user response 1524 to the first visual pattern 1602. Further, in some embodiments, before the response analysis model 1626 is applied, the server 102 may collect a plurality of historical visual stimuli and a collection of historical electrical signals that are associated with the plurality of historical visual stimuli, and train the response analysis model 1626 based on the plurality of historical visual stimuli and the collection of historical electrical signals. Additionally, in some embodiments, the plurality of historical visual stimuli and the collection of historical electrical signals may be communicated from a plurality of computer devices 140 (FIG. 1) to the server 102 in an encrypted format. After receiving the plurality of historical visual stimuli and the collection of historical electrical signals, the server 102 may decrypt the plurality of historical visual stimuli and the collection of historical electrical signals. More details on model training are explained above with reference to FIG. 4.

Innovations in Biometric Feedback

Some embodiments of the VR system may include interactive controls during vision tests to enhance personalized vision care. This VR system may allow users to adjust test parameters in real time through intuitive interactive controls. The VR system may include a headset device 140D equipped with a display and one or more sensors for tracking one or more of eye movement, head orientation, and hand gestures of a user wearing the headset device 140D. In some embodiments, the headset device 140D may be communicatively coupled to a server 102 configured to execute a server-side module for the vision assessment application 328, thereby managing the sequence of vision tests jointly with a device-side module of the vision assessment application 328 executed on the headset device. Users can interact with a 3D virtual environment via a variety of control schemes, such as voice commands, hand gestures, and eye movement, thereby dynamically modifying test parameters (e.g., a contrast level, a stimulus size, and a test speed). By these means, the VR system implements real-time adjustments of visual stimuli based on user comfort and response, may enable personalized, interactive, and adaptive testing experience by implementing, and enhances accuracy and effectiveness of vision tests.

In some embodiments, the VR system may collect comprehensive data on user interactions, including changes to test parameters and corresponding responses. Additionally, it employs a sophisticated biofeedback loop that monitors physiological responses such as heart rate variability, pupil dilation, and galvanic skin response. These physiological metrics may be integrated with alternative visual test results to provide a holistic view of the user's visual and cognitive state (e.g., eye health condition, neurological disorder).

In some embodiments, the vision assessment application 328 may be configured to implement the real-time adjustments made by users via processors of the VR system (e.g., including a headset device 140D and a server). Further, in some embodiments, the VR system may include a quantum co-processor configured to apply quantum computing principles to enhance a speed and accuracy of data processing. This quantum co-processor is particularly adept at handling complex and multidimensional datasets generated by the VR system, thereby improving sensitivity and precision of real-time adjustments of test parameters of the vision tests in the 3D virtual environment. Further, in some embodiments, data collected by different sensors (e.g., the above physiological responses) may be processed, using a machine learning model 350, a quantum computational model, or a combination thereof. The VR system is configured to identify patterns and anomalies that might be imperceptible through conventional methods, offering detailed insights into the user's visual performance and adaptability. The ability to adjust test parameters in real-time allows for the identification of subtle vision issues that might be missed in traditional static testing environments. Additionally, in some embodiments, the VR system supports secure, encrypted communication with a centralized vision health management platform, utilizing quantum encryption protocols to ensure data security. This platform aggregates data from numerous users, enabling large-scale analysis and research. The aggregated data can be cross-referenced with a global health databases to identify emerging trends and potential public health concerns.

Some implementations of the VR system may incorporate one or more of real-time interactive controls, quantum computing, biofeedback integration, and encryption. Such an VR system significantly may enhance customization, accuracy, and user engagement in vision assessments, and pushes boundaries of what is possible in the field of visual health diagnostics.

Figure 17:
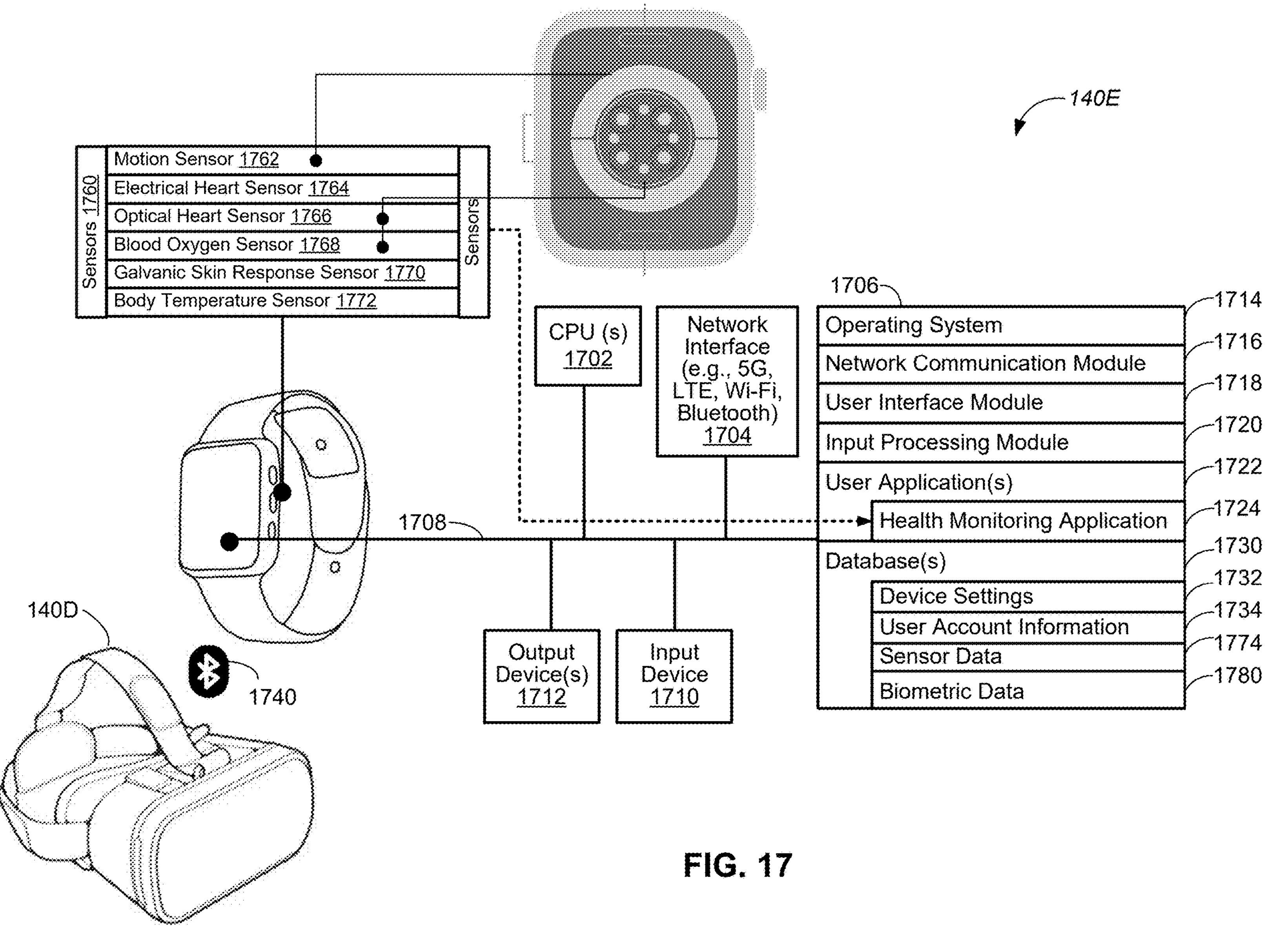
FIG. 17 is a block diagram of an example wearable device for facilitate a virtual vision test implemented on a headset device, in accordance with some embodiments.

FIG. 17 is a block diagram of an example wearable device 140E for facilitate a virtual vision test implemented on a headset device 140D, in accordance with some embodiments. The wearable device 140E may include one or more processing units (CPUs) 1702, one or more network interfaces 1704, memory 1706, and one or more communication buses 1708 for interconnecting these components (sometimes called a chipset). The wearable device 140E may include one or more input devices 1710 that facilitate user input, such as a microphone and a touch screen display. The wearable device 140E may also include one or more output devices 1712 that enable presentation of user interfaces 210 and display content. Examples of the output devices 1712 include, but are not limited to, one or more speakers and/or one or more visual displays.

The wearable device 140E may further include one or more sensors 1760, including one or more of: a motion sensor 1762, an electrical heart sensor 1764, an optical heart sensor 1766, a blood oxygen sensor 1768, a galvanic skin response sensor 1770, and a body temperature sensor 1772. The wearable device 140E may be configured to measure one or more sensing signals (e.g., corresponding to sensor data 1774) and generate a stream of biometric data 1780 based on the one or more sensing signals. In some embodiments, the wearable device 140E can establish a wireless communication link 1740 with the headset device 140D associated with a user of the wearable device 140E. The wireless communication link 1740 may communicate the stream of biometric data 1780 captured by the sensors 1760 using a short-range wireless protocol selected from Bluetooth, Wi-Fi, NearLink, near-field communication (NFC), LPWAN, ultra-wideband (UWB) and IEEE 802.15.

Memory 1706 may include high-speed random-access memory, such as DRAM, SRAM, DDR RAM, or other random-access solid state memory devices; and, optionally, may include non-volatile memory, such as one or more magnetic disk storage devices, one or more optical disk storage devices, one or more flash memory devices, or one or more other non-volatile solid state storage devices. Memory 1706, optionally, may include one or more storage devices remotely located from one or more processing units 1702. Memory 1706, or alternatively the non-volatile memory within memory 1706, may include a non-transitory computer readable storage medium. In some implementations, memory 1706, or the non-transitory computer readable storage medium of memory 1706, stores the following programs, modules, and data structures, or a subset or superset thereof:

- Operating system 1714 including procedures for handling various basic system services and for performing hardware dependent tasks;
- Network communication module 1716 for connecting each wearable device 140E to other devices (e.g., server 102, computer device 140, or storage 106) via one or more network interfaces 1704 (wired or wireless) and one or more communication networks 108, such as the Internet, other wide area networks, local area networks, metropolitan area networks, and so on;
- User interface module 1718 for enabling presentation of information (e.g., a graphical user interface for application(s) 1724, widgets, websites and web pages thereof, and/or games, audio and/or video content, text, etc.) at each wearable device 140E via one or more output devices 1712 (e.g., displays, speakers, etc.);
- Input processing module 1720 for detecting one or more user inputs or interactions from one of the one or more input devices 1710 and interpreting the detected input or interaction;
- One or more user applications 1722 for execution by the wearable device 140E, where in some embodiments, a health monitoring application 1724 may be executed to provide health data (e.g., oxygen level, heart rate, body temperature) or associated data (e.g., walking steps, running speed) to a headset device 140D; and
- One or more databases 1730 for storing at least data including one or more of:
  - Device settings 1732 including common device settings (e.g., service tier, device model, storage capacity, processing capabilities, communication capabilities, etc.) of the wearable device 140E;
  - User account information 1734 for the one or more user applications 1722, e.g., user names, security questions, account history data, user preferences, and predefined account settings;
  - Sensor data 1774 generated from electrical signals generated by the sensors 1760; and
  - Biometric data 1780 that are generated from the sensor data 1774 and indicate a health condition of the user wearing the wearable device 140E and the headset device 140D.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise rearranged in some embodiments. In some embodiments, memory 1706, optionally, stores a subset of the modules and data structures identified above. Furthermore, memory 306, optionally, stores additional modules and data structures not described above.

Figure 18:
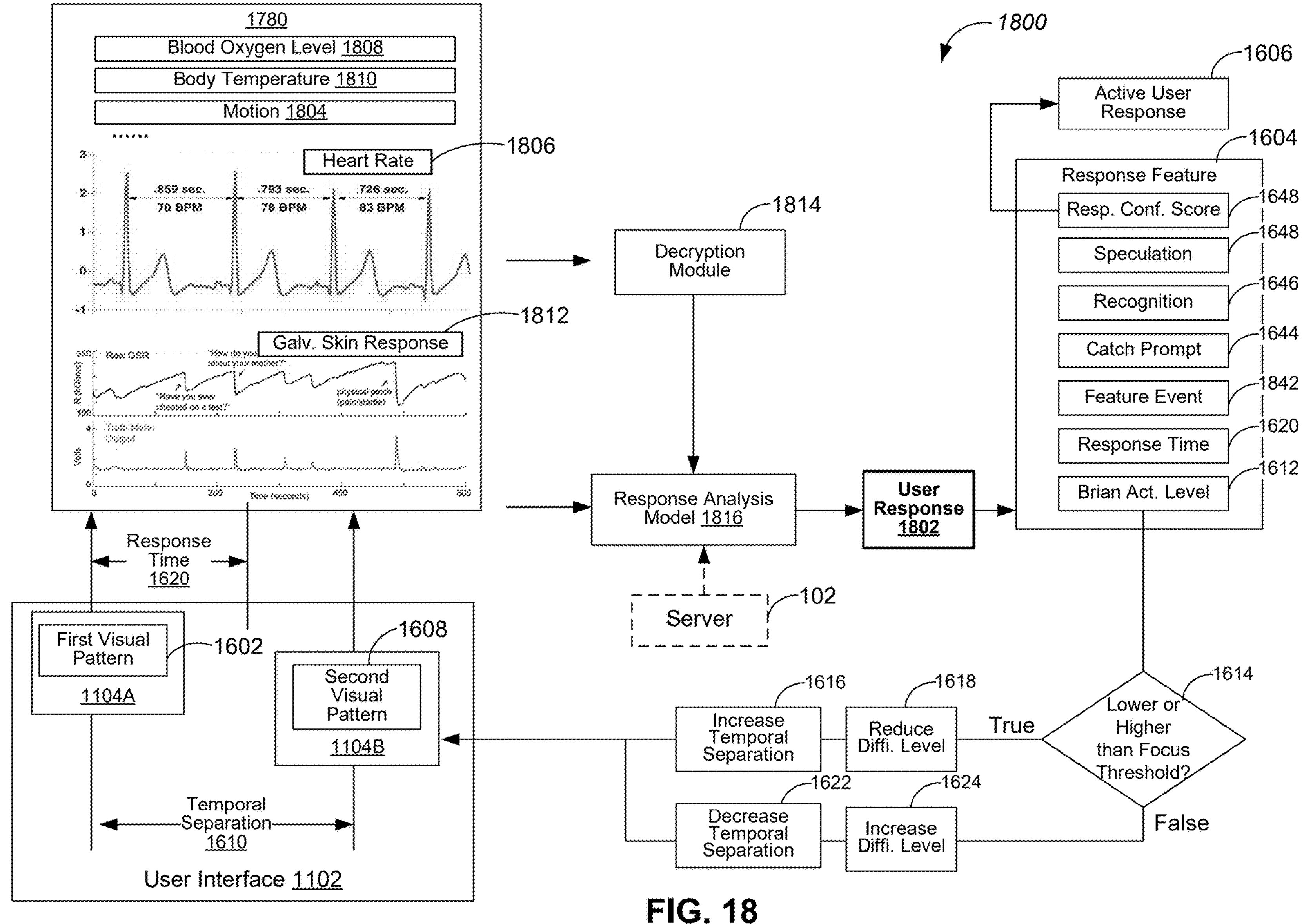
FIG. 18 is a diagram showing a vision test system including a headset device and a wearable device, in accordance with some embodiments.

FIG. 18 is a diagram showing a vision test system 1800 including a headset device 140D and a wearable device 140E, in accordance with some embodiments. The vision test system 1800 may include a computer device 140 (e.g., headset device 140D), which further may include one or more processors 302, memory 306 storing instructions to be implemented by the processor(s) 302, and a head-mounted display (HMD) 312A. The computer device 140 may execute a user application (e.g., a visual assessment application 328) configured to enable the virtual vision test and generate a VR user interface 1102 corresponding to a 3D virtual environment. A user interface 1102 may be rendered, on the HMD 312A, and may include a first visual stimulus 1104A corresponding to the virtual vision test. The computer device 140 establishes a wireless communication link 1740 with a wearable device 140E (FIG. 17) associated with a user of the computer device 140. While displaying a first visual stimulus 1104A, in real time, the electrode device 200 may collect a stream of biometric data 1780 from the wearable device 140E via the wireless communication link 1740. The computer device 140 may determine a second visual stimulus 1104B following the first visual stimulus 1104A and a user response 1802 to the first visual stimulus 1104A based on the stream of biometric data 1780.

In some the wearable device 140E may include one or more of: a motion sensor 1762, an electrical heart sensor 1764, an optical heart sensor 1766, a blood oxygen sensor 1768, a galvanic skin response (GSR) sensor 1770, and a body temperature sensor 1772. The wearable device may be configured to measure one or more sensing signals and generate the stream of biometric data 1780 based on the one or more sensing signals. In an example, a motion level 1804 of the user may be determined from sensor data 1774 provided by the motion sensor 1762, and exceed a motion threshold, which indicates that the user experiences an elevation of a stress level. In another example, a hear rate 1806 measured by the electrical heart sensor 1764 and/or the optical heart sensor 1766 may exceed a threshold level indicating that the user experiences an elevation of a stress level. In another example, a blood oxygen level 1808 or a body temperature level 1810 may be measured to indicate the user response 1802. In some embodiments, the GSR sensor 1770 may measure a skin response 1812 including a varying level of skin conducting the electric current. Higher levels of perspiration on the skin can lead to a greater conductance of electrical currents. A higher level of conductivity of the skin after an event can therefore be interpreted as either positive or negative emotional arousal. The stress level or the positive or negative emotional arousal can be associated with an ongoing vision test session and used to determine the second visual stimulus 1104B following the first visual stimulus 1104A and/or the user response 1802 to the first visual stimulus 1104A. Stated another way, in some embodiments, the stream of biometric data 1780 may provide a spontaneous response to the first visual stimulus 1104A, and the user response 1802 may include the spontaneous response generated based on the stream of biometric data 1780.

In some embodiments, the wireless communication link 1740 communicates the stream of biometric data 1780 in an encrypted format, thereby protecting the biometric data 1780 from a tampering attempt. After receiving the stream of biometric data 1780, the computer device 140 (e.g., a decryption module 1814) may decrypt the stream of biometric data 1780.

In some embodiments, the first visual stimulus 1104A may correspond to a temporal sequence of visual patterns, and include a first visual pattern 1602. While displaying the first visual pattern 1602, the computer device 140 may determine a response feature 1604 of the user response to the first visual pattern 1602 based on the stream of biometric data 1780. Based on the response feature 1604, the computer device 140 may dynamically select a subsequent visual pattern 1608 immediately following the first visual pattern 1602, and determine next temporal separation 1610 between the first visual pattern 1602 and the subsequent visual pattern 1608. The subsequent visual pattern 1608 corresponds to the second visual stimulus 1104B.

Further, in some embodiments, the computer device 140 may determine a focus level (e.g., corresponding to a brain activity level 1612) based on the stream of biometric data 1780. In accordance with a determination that the focus level is lower than a focus threshold, the next temporal separation 1610 may be increased (operation 1616) compared with a current temporal separation (not shown) between the first visual pattern 1602 and a previous visual pattern, and alternatively, a difficulty level of the subsequent visual pattern 1608 may be reduced (operation 1618) compared with that of the first visual pattern 1602.

In some embodiments, the response feature 1604 may include a response time 1620. In accordance with a determination that the response time 1620 is greater than a response threshold, the next temporal separation 1610 may be increased compared with a current temporal separation between the first visual pattern 1602 and a previous visual pattern, and alternatively, a difficulty level of the subsequent visual pattern 1608 may be reduced compared with that of the first visual pattern 1602.

Also, in some embodiments, the virtual vision test may be one of a visual acuity test, a visual field test, a visual depth test, a color blindness test, a retinoscopy, a refraction test, an astigmatism test, and a contact lens exam. The first visual pattern 1602 may be selected from a plurality of predefined visual patterns to implement the virtual vision tests and configured to be displayed with one or more adjustable display parameters (e.g., a display size, a spatial pitch, a temporal pitch, a contrast level, and a brightness level).

In some embodiments, while displaying a first visual pattern 1602, the computer device 140 may determine a response feature 1604 of the user response to the first visual stimulus 1104A based on the stream of biometric data 1780. The response feature 1604 may include one or more of: a motion level, a stress level, whether each of one or more feature events 1842 occurs, whether the user catches a prompt 1644, and whether the user has a recognition 1646 or speculation 1648 about the first visual stimulus 1104A.

In some embodiments, a response analysis model 1816 may be applied to process a subset of the stream of biometric data 1780, which is recorded immediately after a first visual pattern 1602, an determine the user response to the first visual pattern 1602. The user response includes or indicates whether the user speculates about the first visual pattern 1602. Further, in some embodiments, the virtual vision test may include a color vision test, and the first visual pattern 1602 may be applied in the color vision test to evaluates whether there are difficulties distinguishing between different colors. The user response to the color vision test may be automatically determined from the stream of biometric data 1780. Additionally, in some embodiments, the computer device 140 may collect the active user response 1606 to a first visual pattern 1602 using a microphone or a camera of the computer device 140, and apply a response analysis model 1816 to process a subset of the stream of biometric data 1780, which is recorded immediately after the first visual pattern 1602. The computer device 140 may compare spontaneous and active user responses and generate a confidence score 1650 associated with the user response 1524.

In some embodiments, the computer device 140 may obtain a response analysis model 1816 from a server 102 associated with the computer device 140, and apply the response analysis model 1816 to process the stream of biometric data 1780, thereby determining the information of at least one of the first visual stimulus 1104A or the user response 1802 to the first visual stimulus 1104A. Further, in some embodiments, before applying the response analysis model 1816, the server 102 may collect a plurality of historical visual stimuli and a collection of historical biometric data that are associated with the plurality of historical visual stimuli, and train the response analysis model 1816 based on the plurality of historical visual stimuli and the collection of historical biometric data.

Some implementations of the vision test system 1800 may apply the response analysis model 1816 to determine the response feature 1604 substantially similar to those determined by the response analysis model 1626 of the vision test system 1600 (FIG. 16). More details on the response feature 1604 and associated control of subsequent visual stimuli are explained above with reference to FIG. 16.

Innovations in Biophotonic Sensors

Development of a fully immersive VR environment specifically designed for comprehensive vision testing represents a major innovation in the field of ophthalmology. The present application describes embodiments related to a VR-based system that may provide an all-encompassing visual experience to conduct a wide array of vision tests. This system may include a VR headset with high-resolution displays and advanced sensors capable of capturing detailed eye movements and head orientation. The VR headset may be connected to a powerful computer device running specialized vision test software. The immersive VR environment may simulate various visual scenarios and test conditions, such as different lighting, contrast levels, and dynamic visual stimuli, allowing for thorough and precise assessments of visual acuity, color vision, depth perception, and peripheral vision. By creating a controlled and interactive testing environment, the system may ensure that each vision test is conducted under optimal conditions tailored to the individual user's needs.

The computer device integrated with the VR system may be equipped with multiple processors and extensive memory to run the comprehensive vision test software and process the data collected within the immersive environment. The system may include a bio-photonic sensor array embedded in the VR headset, capable of detecting subtle changes in retinal blood flow and oxygenation levels during visual tasks. This biophotonic data may be synchronized with traditional metrics such as eye movements, reaction times, accuracy of visual tasks, and other critical parameters, creating a multi-layered dataset.

Advanced algorithms, including hybrid quantum-classical machine learning techniques, may be applied to analyze this rich dataset. The system may use a quantum neural network to correlate bio-photonic data with visual performance, providing unprecedented insights into the user's visual capabilities and potential impairments. This nuanced analysis can reveal early signs of retinal diseases and neurodegenerative conditions that traditional methods might miss.

The immersive VR environment may also support secure data transmission to a centralized vision health management platform through encrypted quantum communication channels. This platform aggregates data from multiple users, facilitating large-scale analysis and research into vision health trends. The platform employs a distributed ledger technology to ensure data integrity and traceability, allowing for secure and transparent data sharing among authorized researchers and healthcare providers.

By offering a fully immersive and interactive environment, coupled with advanced bio-photonic sensing and quantum-enhanced data analysis, the disclosed VR system may enhance the accuracy, engagement, and effectiveness of vision testing. This innovative approach may provide a superior alternative to traditional methods, enabling early detection of complex visual and neurological conditions and contributing to a more comprehensive understanding of vision health.

Figure 19:
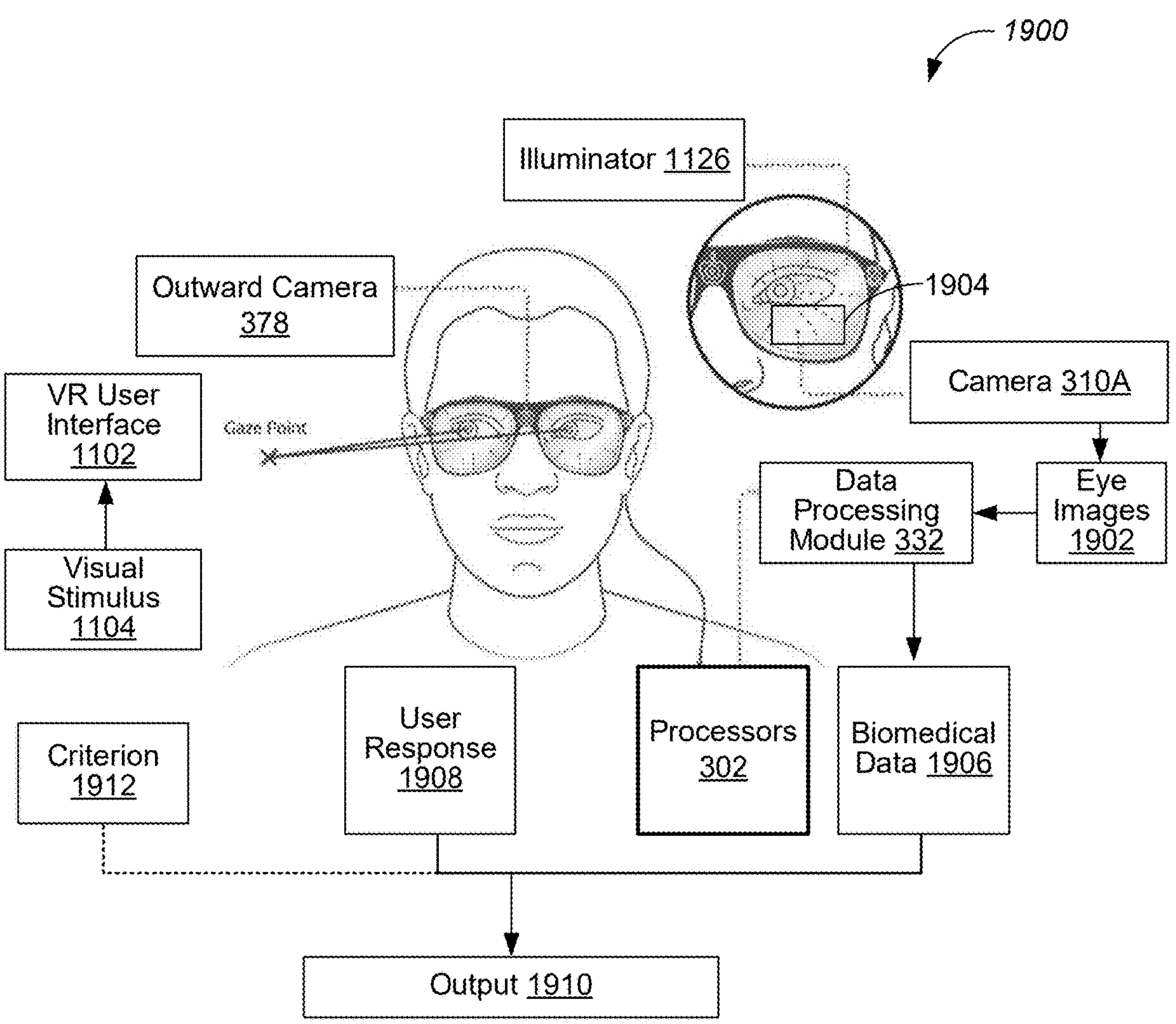
FIG. 19 is a diagram showing a vision test system configured to implement a virtual vision test based on biophotonic sensor data, in accordance with some embodiments.

FIG. 19 is a diagram showing a vision test system 1900 configured to implement a virtual vision test based on biophotonic sensor data, in accordance with some embodiments. The vision test system 1900 may be implemented using a computer device 140 (e.g., headset device 140D), which may include one or more processors 302, memory 306 storing instructions to be implemented by the processor(s) 302, a head-mounted display (HMD) 312A, and a camera 310A. The computer device 140 may execute a user application (e.g., a visual assessment application 328) configured to enable the virtual vision test and generates a VR user interface 1102 corresponding to a 3D virtual environment. A visual stimulus 1104 may correspond to the virtual vision test, and be displayed on the user interface 1102. The computer device 140 can direct the camera 310A to an eye area of a user wearing the computer device 140. While displaying the visual stimulus 1104, in real time, the camera 310A may capture a sequence of eye images 1902. Each eye image may include 1106 a respective region of interest (ROI) 1904 corresponding to an eyelid of the user. The computer device 140 can extract biomedical data 1906 from the sequence of eye images 1902.

After obtaining a user response 1908 to the visual stimulus 1104, the computer device 140 may generate an output 1910 based on the user response 1908 and the biomedical data 1906. The output 1910 indicates at least whether the user response 1908 satisfies a criterion 1912. In some embodiments, the user response 1908 may include an active user response sensed by an alternative sensor 360 (e.g., an outward camera 378, a microphone 380). Examples of the active user response include, but are not limited to, head nodding, a hand gesture, and a voice indicator. The active user response indicates an optotype displayed on the user interface 1102 or confirms whether the user recognizes a visual pattern.

In some embodiments, the computer device 140 may further include an illuminator 1126 configured to illuminate an eye area covered by the computer device 140 and facilitate capturing the eye images 1106 by the eye-tracking camera 366. Further, in some embodiments, the illuminator 1126 may include a near-infrared or infrared diode configured to illuminate the eye area with near-infrared or infrared light. The camera 310 may include a near-infrared sensor array or an infrared sensor array 370 (FIG. 3).

In some embodiments, the eye images 1902 captured by the camera 310A of the computer device 140 may also be used to determine eyeball movement data that is representative of an eye position 1110 (FIG. 19). Based on the eyeball movement data, the visual stimulus 1104 and the eye movement information 1108 may be used to determine an eye health condition 1114 or an eyeball movement disorder 1116.

In some embodiments, the visual stimulus 1104 may include a visual pattern 700 (FIG. 7), and may be applied in the vision test system 1800 or 1900. Blood oxygen levels, heart rate, and galvanic skin response (GSR) can be used to monitor physiological responses while a user viewing the visual pattern 700. The physiological responses indicate stress or discomfort caused by visual strain. By analyzing these responses, the visual pattern 700 can be used to detect visual impairments and understand associated impact on overall eye well-being and stress levels.

Figure 20:
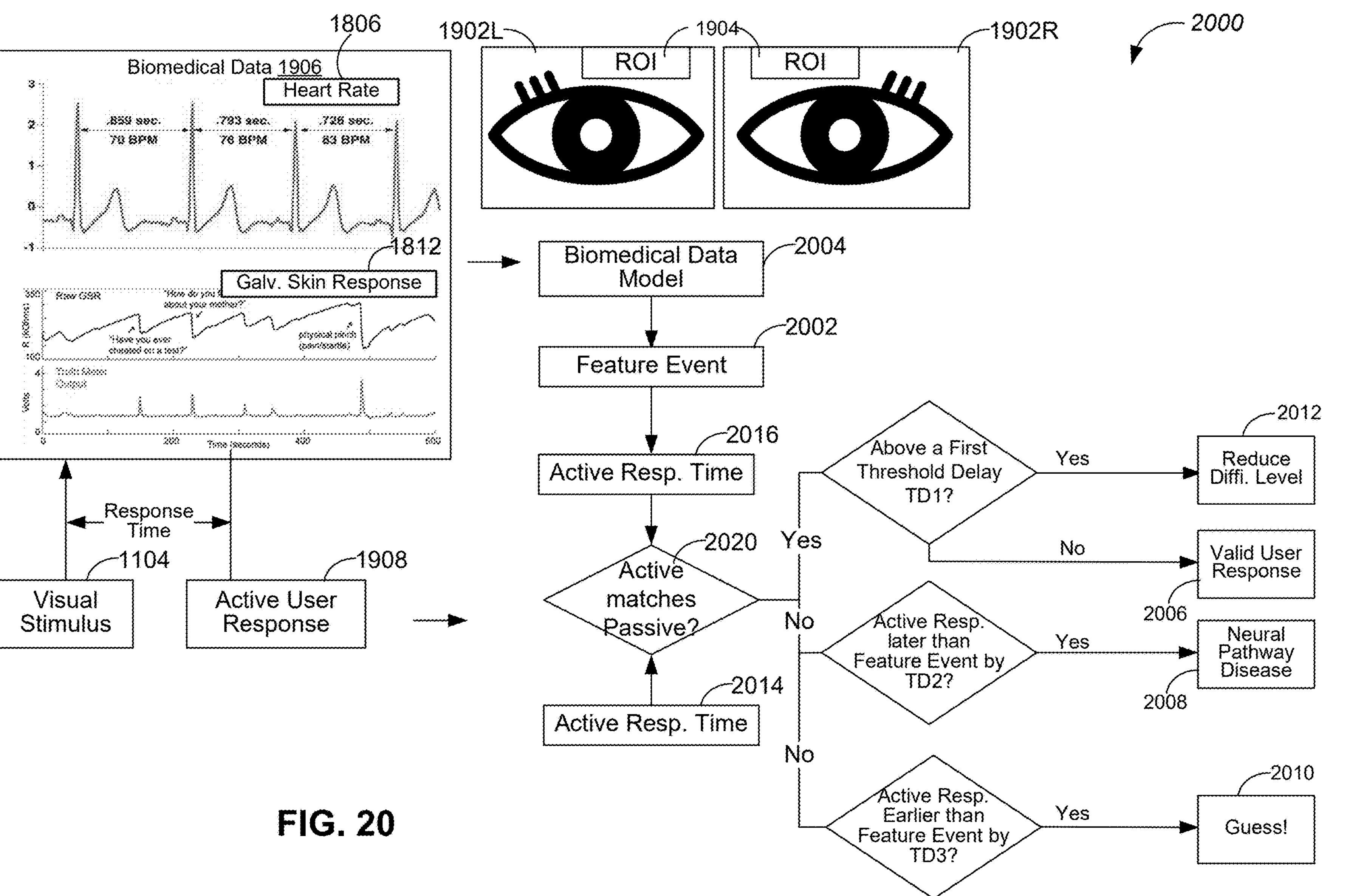
FIG. 20 is a flow diagram of an example method of monitoring a condition of an eye area for vision test, in accordance with some embodiments.

FIG. 20 is a flow diagram of an example method 2000 of monitoring a condition of an eye area for vision test, in accordance with some embodiments. The computer device 140 may execute a user application (e.g., a visual assessment application 328) configured to enable the virtual vision test and generates a VR user interface 1102 (FIG. 19) corresponding to a 3D virtual environment. A visual stimulus 1104 (FIG. 19) corresponds to the virtual vision test, and is displayed on the user interface 1102. The computer device 140 may direct the camera 310A to an eye area of a user wearing the computer device 140. While displaying the visual stimulus, in real time, the camera 310A of the computer device 140 may capture a sequence of eye images 1902 each of which may include a respective ROI 1904 corresponding to a subset of the eye area of the user (e.g., an eyelid). Biomedical data 1906 may be extracted from the sequence of eye images 1902 (specifically, from the ROIs 1904 thereof). After obtaining a user response 1908 to the visual stimulus 1104, the computer device 140 may generate an output 1910 indicating at least whether the user response 1908 satisfies a criterion 1912.

In some embodiments, for each of the sequence of eye images 1902, the computer device 140 may crop the respective eye image 1902 to generate a left eye image 1902L and/or a right eye image 1902R including a respective eye of the user based on a predefined aspect ratio. After cropping, a resolution of the respective eye image 1902 is adjusted to a predefined resolution. Each of the left and right eye images 1902 may include a respective ROI 1904. In some embodiments, the eye images 1902 may be captured in a near-infrared or infrared domain, and processed to the biomedical data 1906 indicating one or more of a heart rate, a galvanic skin response (GSR), and an oxygen level. Stated another way, the biomedical data 1906 may indicate a stress level of the user while the virtual vision test is implemented, and therefore, can be used to determine user spontaneous responses to visual stimuli automatically and without user intervention, which is an efficient solution to provide reliable supplemental information that cannot be provided by the user's active response (e.g., user response 1908) to the visual stimuli.

In some embodiments, a feature event 2002 may be extracted in response to the visual stimulus 1104 based on the biomedical data 1906. Further, in some embodiments, the biomedical data 1906 may include a temporal sequence of heart rate data or a temporal sequence of blood oxygen levels. The feature event 2002 may correspond to the heart rate exceeding a threshold rate or the blood oxygen level dropping below a blood oxygen threshold. In some embodiments, a biomedical data model 2004 may be applied to process the biomedical data 1906 and identify the feature event 2002. The biomedical data model 2004 may be provided by a server 102 after the model 2004 is trained at the server 102. Additionally, in some embodiments, the user response 1908 and the feature event 2002 detected in the biomedical data may have delays from the visual stimulus 1104. The delays may be compared with a first threshold delay, so may the delays be compared to each other (operation 2020) to determine whether active and passive responses match each other.

In some embodiments, the delays may be below a first threshold delay TD1, and the user response 1908 and the biomedical data 1906 match each other. It may be determined that the user response 1908 satisfies the criterion 1912, thereby corresponding to a valid user response 2006. Alternatively, in some embodiments, the user response 1908 may be delayed from the feature event 2002 of the biomedical data 1906 beyond a second threshold delay TD2. It may be determined that the user has a neural pathway disease 2008. The output 1910 may be generated to indicate the neural pathway disease, and the user response 1908 does not satisfy the criterion 1912. Alternatively, in some embodiments, the feature event 2002 of the biomedical data 1906 may be delayed from the user response 1908 beyond a third threshold delay TD3. It may be determined that the user response 1908 is not reliable, and the output 1910 may be generated to indicate that the user response 1908 does not satisfy the criterion 1912 (e.g., is a guess 2010).

Alternatively, in some embodiments, the user response 1908 and the feature event 2002 of the biomedical data 1906 have delays from the visual stimulus 1104, and the delays from the visual stimulus may be above the first threshold delay TD1. It may be determined that the user response 1908 does not satisfy the criterion 1912, and the output 1910 may include a message indicating that the user needs a break or a message requesting reduction of a difficulty level 2012 of the vision test. An instruction may be automatically generated based on the message requesting reduction of a difficulty level of the vision test to adjust one or more subsequent visual stimuli immediately following the visual stimulus 1104.

In some embodiments, the computer device 140 may generate the output 908 by determining an active response time 2014 of the user response 1908 with respect to the visual stimulus 1104 and a passive response time 2016 with respect to the visual stimulus based on the biomedical data. The active response time 2014 and the passive response time 2016 may be compared to generate the output 1910.

Innovations in Dynamic Adjustment of Eye Test Sequences

A VR platform may integrate eye health assessments with interactive storytelling and visual quests, and represent a significant advancement in vision care. The present application may describe embodiments related to a VR-based system designed to evaluate eye health through engaging and immersive experiences. This system may include a VR headset equipped with high-resolution displays and advanced sensors that track eye movements, focus, and response times. The VR headset may connect to a computer device 140 running specialized software that generates interactive stories and visual quests. These narratives and quests may be configured to subtly incorporate vision tests, such as visual acuity, color differentiation, depth perception, and peripheral vision assessments. By embedding these tests within captivating stories and challenges, the platform can enhance user engagement and ensure a comprehensive evaluation of visual function in a manner that is both entertaining and informative.

The computer device 140 integrated with the VR system can house multiple processors and memory modules to execute the interactive storytelling software and process the extensive data collected during the visual quests. The system may include an integrated neuro-ophthalmic interface, capable of measuring cortical responses to visual stimuli using embedded electroencephalogram (EEG) sensors within the VR headset. This neuro-ophthalmic data may be synchronized with detailed metrics on eye movements, visual response accuracy, and interaction patterns within the VR environment, resulting in a multi-faceted dataset that provides a deeper understanding of visual processing.

Advanced data analysis algorithms, including hybrid quantum-classical machine learning techniques, may be employed to interpret this rich dataset. The system may utilize a quantum cognitive model to correlate neuro-ophthalmic responses with visual performance metrics, offering unprecedented insights into the user's eye health and neurological function. This analysis can detect early signs of complex conditions such as amblyopia, glaucoma, and even neurodegenerative diseases that traditional methods might overlook.

The platform can identify specific visual impairments and tracks changes over time, offering valuable information for healthcare providers. Furthermore, the VR platform may ensure secure and encrypted communication with a centralized eye health management system, utilizing blockchain technology to maintain the integrity and confidentiality of the data. This system can aggregate data from numerous users, facilitating large-scale research and analysis, and enabling the creation of a comprehensive visual health database.

By combining eye health assessments with interactive storytelling, visual quests, and neuro-ophthalmic monitoring, the disclosed VR platform significantly can enhance the accuracy, engagement, and overall effectiveness of vision testing. This approach may transform vision assessments into an enjoyable and accessible process for users of all ages, while providing critical insights for early diagnosis and ongoing management of visual and neurological health.

In some embodiments, the invention describes a customized VR entry experience designed to adapt vision testing based on preliminary user inputs, thereby providing a tailored and efficient diagnostic process. This system may leverage a virtual reality headset equipped with high-resolution displays and advanced optical sensors, which gather preliminary data such as age, medical history, and initial visual responses through a user-friendly interface. Upon entering the VR environment, users may be prompted to provide these preliminary inputs, which may be then processed by an AI-driven system. This system can analyze the inputs to customize the sequence and parameters of subsequent vision tests, ensuring they are optimally suited to the user's specific visual profile and needs. The customization may extend to adjusting the difficulty level, the type of tests presented, and the visual stimuli used, thereby enhancing both the accuracy and user experience of the vision testing process. The VR headset may include an intuitive user interface that prompts users to input essential preliminary information, such as age, medical history, current vision issues, and initial responses to basic visual stimuli. This interface is designed to be accessible and easy to navigate, ensuring that users can provide accurate information without difficulty.

In some embodiments, an AI module can process the preliminary inputs to generate a customized vision testing plan. This involves analyzing the data to determine the user's specific needs and tailoring the vision tests accordingly. For instance, the AI might decide to focus more on color vision tests if the preliminary inputs indicate potential color blindness, or adjust the difficulty level of visual acuity tests based on the user's initial responses.

In some embodiments, the vision tests within the VR environment may be dynamically adjusted in real-time based on the user's interactions and responses. This may include modifying the type, sequence, and complexity of tests, as well as the visual stimuli presented. The system may ensure that each test is appropriately challenging and relevant to the user's specific visual profile, thereby improving diagnostic accuracy.

In some embodiments, the system may integrate data from the preliminary inputs and subsequent vision tests into a cloud-based platform. This platform may utilize machine learning algorithms to refine the customization process continuously. By learning from each user interaction, the AI module can enhance the accuracy and effectiveness of the vision tests over time. Additionally, this cloud-based approach can allow healthcare professionals to access and analyze the data remotely, facilitating comprehensive diagnostics and follow-up care.

Figure 21:
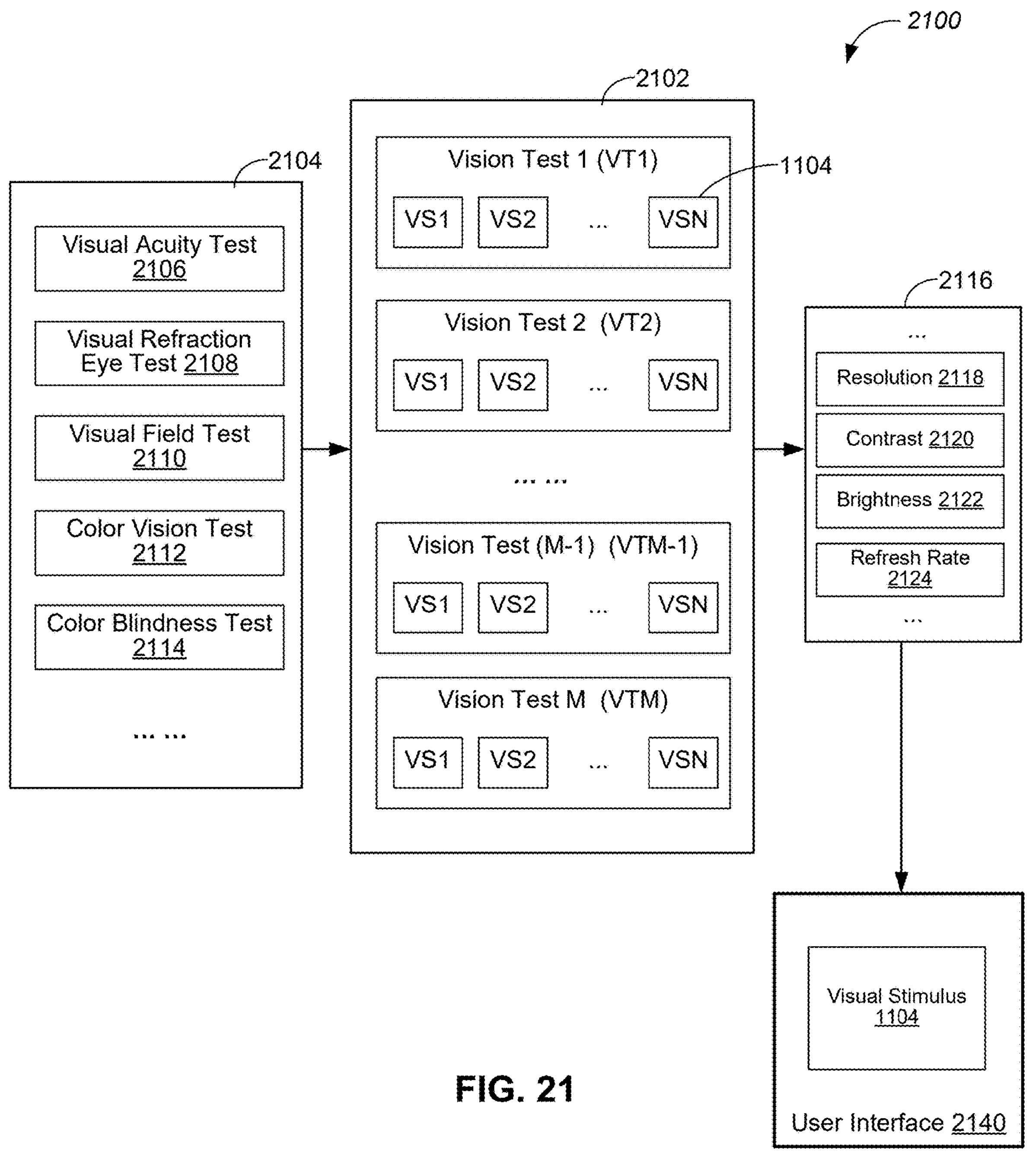
FIG. 21 is a diagram showing an example hierarchical structure of a vision test scheme applied in a virtual vision test, in accordance with some embodiments.

FIG. 21 is a diagram showing an example hierarchical structure 2100 of a vision test scheme applied in a virtual vision test, in accordance with some embodiments. A vision test scheme may include a temporally-ordered sequence of vision tests 2102. Each of the vision tests 2102 may be selected from a plurality of predefined vision tests 2104. Examples of the predefined vision tests 2104 include, but are not limited to, a visual acuity test 2106, a visual refraction vision test 2108, a visual field test 2110, a color vision test 2112, and a color blindness test 2114. In an example, the vision tests 2102 include vision tests VT1, VT2, . . . . VTM−1, and VTM, which may be successively applied. In an example, each of the vision tests VT1, VT2, . . . , VTM−1, and VTM may be distinct from any of a remainder test in the sequence of vision tests 2102. In another example, two of the vision tests VT1, VT2, . . . , VTM−1, and VTM may correspond to the same vision test type (e.g., an visual acuity test 2106).

Each vision test 2102 further may include one or more visual stimuli 1104 (e.g., VS1, VS2, . . . , and VSN). For example, a first vision test VT1 may be a visual acuity test 2106, and the visual stimuli 1104 may include a sequence of optotypes that may be successively displayed. Each visual stimulus 1104 may be presented on a user interface 2140 with a plurality of display parameters 2116. Examples of the display parameters 2116 include, but are not limited to, a display size, a resolution 2118, a contrast level 2120, a brightness level 2122, a spatial pitch, a temporal pitch (e.g., corresponding to a refresh rate 2124), and a background style.

FIG. 22 is a flow diagram of an example method 2200 of dynamically adjusting vision tests, in accordance with some embodiments. A computer device 140 (e.g., a headset device 140D, a desktop computer, a laptop computer 1402A) may include a display, one or more processors, and memory. The computer device 140 may execute a user application (e.g., a visual assessment application) configured to enable the virtual vision test, and generates a user interface 2140. The computer system may obtain historical vision data 2202 (e.g., summaries of previous visits to an optician's office) of a patient user associated with the computer device 140. Based on the historical vision data, an ordered sequence of vision tests 2102 may be determined and may include a first vision test 2102A for the patient user. The first vision test 2102A (VTA) may be followed by a set of one or more subsequent vision tests 2102S (e.g., VTB, VTC) of the ordered sequence of vision tests 2102. Each of the first vision test 2102A or subsequent vision test(s) 2102S may include one or more visual stimuli 1104. The computer device 140 enables the ordered sequence of vision tests 2102 on the user interface 2140. More specifically, the computer device 140 may display, on the user interface 2140, a first visual stimulus 1104A (VSA) corresponding to the first vision test 2102A (VTA). A user response 2204 to the first vision test 2102A (VTA) (e.g., to the first visual stimulus 1104A) may be obtained. The computer device 140 may dynamically adjust a set of one or more subsequent visual stimuli 1104S (e.g., a subsequent visual stimulus 1104B in the vision test VTA, those in vision tests VTB, VTC) based on the user response 2204 to the first visual stimulus 1104A. In some embodiments, the user response 2204 to the first visual stimulus 1104A may be applied jointly with one or more additional user responses to dynamically adjust the set of one or more subsequent visual stimuli 1104S.

In some embodiments, the computer device 140 may include a headset device 140D, and the display for presenting the sequence of vision tests 2102 may include a head-mounted display (HMD). The user interface 2140 may include a VR user interface corresponding to a 3D virtual environment, and the ordered sequence of vision tests 2102 may be rendered in the 3D virtual environment.

In some embodiments, the computer device 140 may dynamically adjust the set of one or more subsequent visual stimuli 1104S by adjusting at least one of a total number (e.g., 1, 2, or more) or an order of the set of one or more subsequent visual stimuli 1104S. More specifically, in some embodiments, based on the user response 2204, the computer device 140 may bypass a first one (e.g., VSB) of the set of one or more subsequent visual stimuli 1104S, add an alternative visual stimuli 1104C (VSC) or vision test 2102C (VTD) to the set of one or more subsequent visual stimuli 1104S, shorten a length of a second one (e.g., VTC) of the set of one or more subsequent vision tests 2102S, extend a length of a third one (e.g., VTC) of the set of one or more subsequent vision tests 2102S, advance a fourth one of the set of one or more subsequent visual stimuli 1104S, postpone a fifth one of the set of one or more subsequent visual stimuli 1104S, or swap two (e.g., VTB and VTC) of the set of one or more subsequent vision tests 2102S.

In some embodiments, the computer device 140 may determine a length, content, a temporal separation, and a display parameter 2116 (FIG. 21) of at least one subsequent vision test 2102S (e.g., VTB). Further, in some embodiments, the display parameter 2116 is one of: a resolution 2118, a display size, a spatial pitch, a temporal pitch (e.g., corresponding to a refresh rate 2124), a contrast level 2120, and a brightness level 2122 of a visual stimulus (e.g., an optotype, a visual pattern) associated with the at least one subsequent vision test 2102S.

In some embodiments, the computer device 140 may determine a difficulty level 2206 associated with the set of one or more subsequent visual stimuli 1104S, and adjust the difficulty level 2206 based on the user response 2204. Based on the adjusted difficulty level 2206, one of a plurality of predefined vision tests 2104 may be selected to be rendered on the user interface 2140 for the patient user. In some embodiments, the computer device 140 may adjust the difficulty level 2206 based on the user response 2204. Based on the adjusted difficulty level 2206, one or more visual stimuli 1104 may be selected from a plurality of predefined visual stimuli for display on the user interface 2140 for the patient user.

In some embodiments, the first vision test 2102A may include both the first visual stimulus 1104 (VSA) and the set of one or more subsequent visual stimuli 1104S (e.g., including only visual stimuli (e.g., VSB) in the first vision test 2102A). The user response 2204 may be obtained after the first visual stimulus 1104A is displayed. The set of one or more subsequent visual stimuli 1104B may be dynamically adjusted based on the user response 2204 to the first visual stimulus 1104A. Stated another way, subsequent visual stimuli may be dynamically adjusted based on the user response 2204 to the first visual stimulus 1104A internally within the first vision test 2102A. Alternatively, in some embodiments, the set of one or more subsequent visual stimuli 1104S may include at least one visual stimulus 1104 that is located in at least one vision test 2102 (e.g., VTB, VTC) distinct from the first vision test 2102A. The user response 2204 to the first visual stimulus 1104A can therefore be applied to adjust one or more subsequent visual stimuli 1104S in a different subsequent vision test 2102S. Alternatively, in some embodiments, the set of one or more subsequent visual stimuli 1104S may include two visual stimuli that may be located in the first vision test 2102A and an another vision test distinct from the first vision test 2102A, respectively. The user response 2204 to the first visual stimulus 1104A may therefore be applied to adjust subsequent visual stimuli 1104S in both the first vision test 2102A and a different subsequent vision test 2102S.

More specifically, in some embodiments, each of one or more subsequent visual stimuli 1104S may include a visual pattern. The visual pattern can be displayed with a temporal separation from an immediately preceding visual pattern or an immediately subsequent visual pattern. The content, the temporal separation, or a display parameter of at least one subsequent visual stimulus 1104S can be adjusted based on the user response 2204 to the first visual stimulus 1104A.

In some embodiments, the historical vision data 2202 of the patient user may be a document including a medical history 2208 of the patient user. The computer device 140 extracts one or more key words 2210 concerning an eye health condition of the patient user from the document, and selects the ordered sequence of vision tests 2102 from a plurality of predefined sequences of vision tests 2212 based on the one or more key words 2210. Each predefined sequence of vision tests 2212 may include a respective ordered sequence of predefined vision tests 2104. The computer system further may determine one or more respective visual stimulus 1104 of each vision test 2102. For example, the first vision test 2102A may include at least the visual stimuli 1104A and 1104B.

In some embodiments, the computer device 140 may determine the ordered sequence of vision tests 2102 by applying a medical information processing model 2214 to process the historical vision data 2202 and select the ordered sequence of vision tests 2102 from a plurality of predefined sequences of vision tests 2212. The medical information processing model 2214 may be received from, and trained by, a server 102 (FIG. 1) communicatively coupled to the computer device 140.

In some embodiments, the computer device 140 may present to the patient user a plurality of prompts 2216 and obtain a plurality of user answers 2218 to the plurality of prompts 2216, e.g., when the patient user checks into an optician's office. The ordered sequence of vision tests 2102 may be determined based on both the historical vision data 2202 and the plurality of user answers 2218. For example, the medical information processing model 2214 may be applied to process both the historical vision data 2202 and the user answers 2218 for generating the sequence of vision tests 2102. In some embodiments, the medical information processing model 2214 may include a language model configured to process natural language inputs corresponding to the historical vision data 2202 and the user answers 2218.

Innovations in Eye Deficiency Compensation

Some embodiments of the present disclosure may be directed to interactive learning about eye health through guided VR documentaries, incurring a significant advancement in educational and healthcare technologies. A VR-based system may be configured to educate users about eye health by immersing them in guided VR documentaries. This system may include a VR headset equipped with high-resolution displays and advanced sensors that track eye movements and head orientation. The VR headset may be connected to a computer device running specialized software that presents guided documentaries on various aspects of eye health, including anatomy, common vision disorders, preventive care, and treatment options. These documentaries may be interactive, allowing users to engage with the content by selecting topics of interest, answering quiz questions, and participating in visual demonstrations that enhance their understanding of eye health. By offering a captivating and educational experience, the VR method may ensure that users gain valuable knowledge about maintaining and improving their eye health.

A computer device integrated with the VR system may include multiple processors and memory modules to execute a guided documentary software and process user interactions. In some embodiments, the computer device may incorporate a biometric feedback mechanism configured to monitor physiological parameters, such as pupil dilation, heart rate variability, and galvanic skin response, in real time. These biometric signals, captured through sensors embedded in the VR headset, may provide additional layers of data on the user's engagement and emotional response to the educational content.

In some embodiments, data collected by the computer device 140 may include detailed records of user engagement, responses to quiz questions, interaction patterns within the VR environment, and biometric feedback. Advanced analysis algorithms, including hybrid quantum-classical machine learning techniques, may be applied to this rich dataset. For instance, the computer device 140 may leverage a quantum-enhanced adaptive learning model to dynamically adjust the documentary content based on real-time biometric and interaction data, providing highly personalized feedback and recommendations tailored to the user's learning progress and specific eye health concerns.

The VR documentaries may be configured to adapt to the user's knowledge level, learning pace, and emotional state, ensuring an individualized and immersive educational experience. Additionally, the system may support secure, encrypted communication with a centralized eye health education platform, utilizing quantum encryption protocols to ensure data security and privacy. This platform may aggregate data from multiple users, facilitating large-scale analysis and research into eye health education trends and the effectiveness of various educational strategies.

By combining interactive learning with guided VR documentaries, biometric feedback, and quantum-enhanced adaptive learning, the disclosed VR method significantly enhances the accessibility, engagement, and effectiveness of eye health education. This innovative approach transforms the learning experience into a dynamic and emotionally responsive journey, making it an invaluable tool for users of all ages and providing critical insights for educators and healthcare providers.

FIG. 23 is a diagram illustrating an example process 2300 of dynamically adjusting display of media content based on a visual deficiency of a user, in accordance with some embodiments. A computer device 140 (e.g., a headset device 140D, a desktop computer, a laptop computer 1402A) may include a display (e.g., HDD 312A in FIG. 3), one or more processors, and memory. The computer device 140 may obtain the media content 2302 to be rendered on the display and information of a visual deficiency 2304 of a user associated with the display (e.g., a user wearing the headset device 140D). Based on the information of the visual deficiency 2304 of the user, the media content 2302 may be compensated, e.g., by a data processing module 332 (FIG. 3), to generate compensated media content 2306 that is further rendered on the display for the user. In some embodiments, one or more display parameters 2116 (e.g., a resolution 2118, a contrast level 2120, a brightness level 2122, a refresh rate 2124, gamma compensation) of the display of the computer device 140 may be adjusted to compensate the media content 2302. By these means, display of the media content 2302 may be customized for the user to adapt to the user's visual deficiency, thereby enhancing image quality that can be provided by the computer device 140.

In some embodiments, the computer device 140 may render a sequence of visual stimuli 1104 on a user interface 1102, and obtain a plurality of user responses 2308 to the sequence of visual stimuli 1104. The visual deficiency of the user may be determined based on the plurality of user responses 2308. Stated another way, the computer device 140 may implement a virtual vision test to obtain the information of the user's visual deficiency 2304. In an example, the visual pattern 700 (FIG. 7) is applied to determine visual acuity and astigmatism for a particular user before the media content is compensated for this user.

In some embodiments, the visual deficiency compensated by the computer device 140 may include a color vision deficiency 2310 corresponding to a difficulty in telling a difference among a plurality of colors. The plurality of colors in the media content 2302 may be adjusted based on the visual deficiency of the user, thereby generating the compensated media content 2306. In an example, the color vision deficiency 2310 may include a red-green color blindness, and the information of the visual deficiency 2304 may include a severity level of insensitivity to a difference between red and green colors. A color shade of at least one of the red or green colors may be adjusted to generate the compensated media content 2306. In some embodiments, a green area may be displayed with flickering on a background red color that cannot be differentiated from the green area by the user's eyes. In some embodiments, a red area may be displayed with flickering on a background green color that cannot be differentiated from the red area by the user's eyes. In some embodiments, a brightness level of at least one of the red or green colors may be adjusted to generate the compensated media content 2306. A variation of the color shade or the brightness level may be determined based on the severity level of insensitivity to the difference between red and green colors. Alternatively, in some embodiments, other types of the color vision deficiency 2310 may be adjusted based on a severity level of color insensitivity associated with a corresponding type of color vision deficiency 2310.

In some embodiments, the display of the computer device 140 may include an HMD, and a user interface 2312 may include a virtual reality (VR) user interface corresponding to a 3D virtual environment. The compensated media content 2306 may be rendered on the user interface 2312 and in the 3D virtual environment.

In some embodiments, the computer device 140 may obtain a document including a medical history 2208 of the user, and extracts the information of the visual deficiency 2304 of the user from the document. In an example, the document may include the user's eye prescription. In another example, the document may include summaries of the user's previous visits to an optician's office. Further, in some embodiments, the computer device 140 may extract the information of the visual deficiency 2304 by applying a medical information processing model 2314 to process the medical history 2208. The information of the visual deficiency 2304 may include at least a type and a severity level of the visual deficiency of the user. Additionally, in some embodiments, the computer device 140 may obtain the medical information processing model from a server 102 associated with the computer device 140, after the medical information processing model is trained on the server 102.

Advanced display technologies can be used to compensate for detected visual impairments. Real-time display compensation can provide immediate visual relief and improve the user's viewing experience. It can be particularly useful in VR or AR environments where precise visual accuracy is crucial.

Figure 24A:
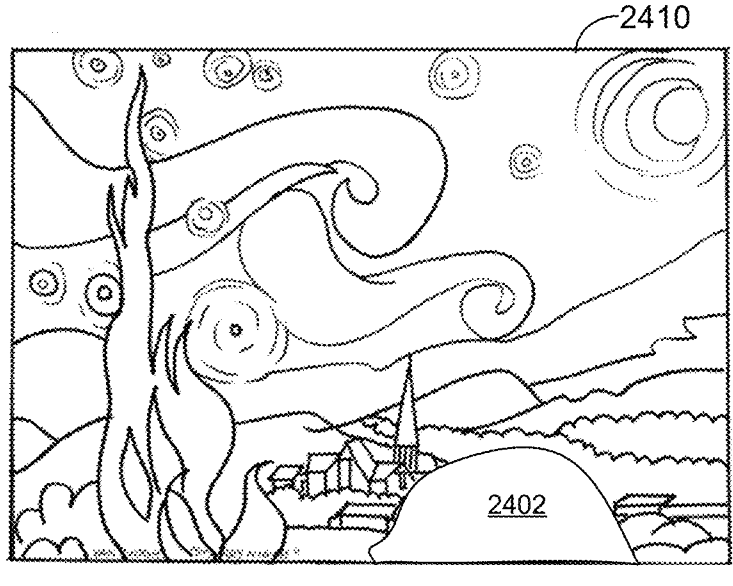
FIG. 24A is an example image perceived by a user who has a visual field impairment.
Figure 24B:
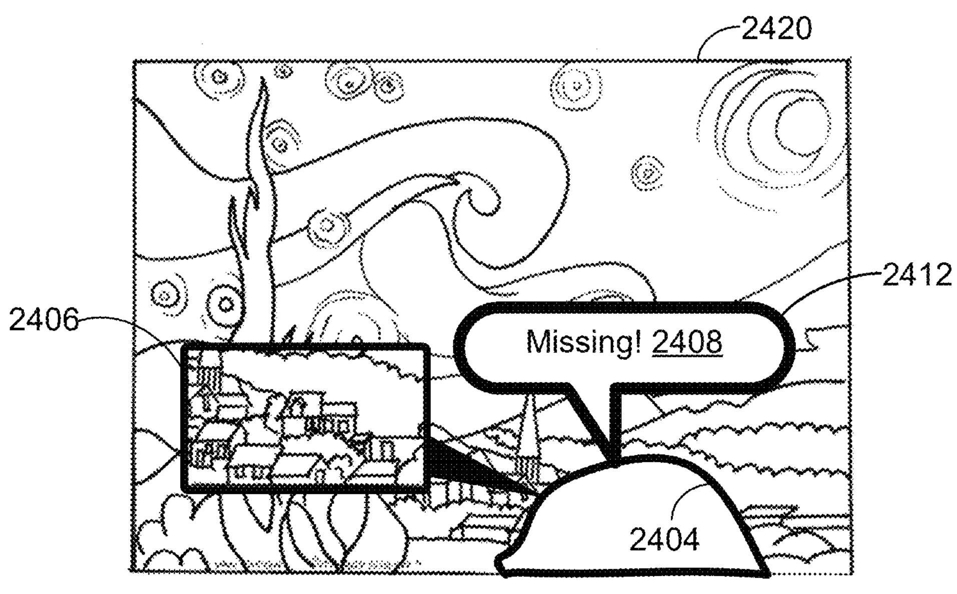
FIG. 24B is an example image including compensated media content for the user, in accordance with some embodiments.

FIG. 24A is an example image 2410 perceived by a user who has a visual field impairment, in accordance with some embodiments, and FIG. 24B is an example image 2420 including compensated media content 2306 for the user, in accordance with some embodiments. The visual deficiency of the user may include a vision field impairment. The information of the visual deficiency 2304 may identify a first location 2402 of the vision field impairment. For example, referring to FIG. 24A, the first location 2402 may be located near a bottom edge of a visual field of the user's eye. In some embodiments, referring to FIG. 24B, a display of the computer device 140 may display a mark identifying the first location 2402 of the vision field impairment. For example, the mark 2404 may include a highlighted edge of an area losing a sight at the first location 2402 of the vision field impairment.

In some embodiments, the mark 2404 may correspond to a subset of missing media content corresponding to the first location 2402 of the vision field impairment. The subset of missing media content may be displayed in a distinct location. For example, an overlay window 2406 may be displayed to present the compensated media content 2306 (FIG. 23). The subset of missing media content may be moved to be displayed in the overlay window 2406. In some embodiments, the mark 2404 may correspond to a message 2408, which is displayed within a speech bubble 2412, indicating that part of the media content 2302 corresponding to the first location 2402 is missing.

Figure 25A:
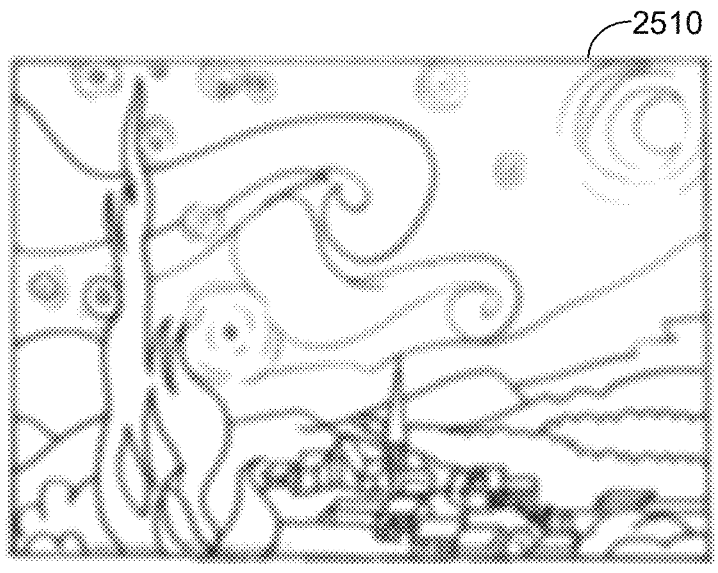
FIG. 25A is an example image perceived by a user having nearsightedness, in accordance with some embodiments.
Figure 25B:
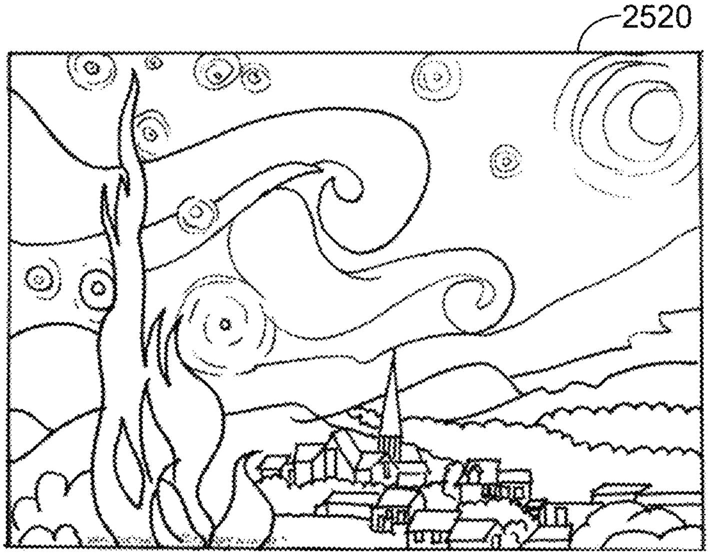
FIG. 25B is an example image including compensated media content 2306 for the user, in accordance with some embodiments.

FIG. 25A is an example image 2510 perceived by a user having nearsightedness, in accordance with some embodiments, and FIG. 25B is an example image 2520 including compensated media content 2306 for the user, in accordance with some embodiments. The image 2510 may be displayed with a resolution that allows sufficient details. The nearsightedness of the user make the image 2510 may appear blurry in the user's eyes, causing inconvenience to the user, particularly when the user wears the headset device 140D. Based on the information of the nearsightedness of the user (e.g., measured in Diopters), the image 2510 may be compensated, such that the image 2520 including the compensated media content 2306 may be perceived by the user's eyes with a sufficient level of details.

In some embodiments, as a result of nearsighted ness, the visual deficiency may include a visual acuity level that is lower than a visual acuity threshold. In accordance with a determination that the visual acuity level that is lower than the visual acuity threshold, the media content 2302 (FIG. 23) may be compensated and rendered as the image 2520, allowing the user to review the media content 2302 without wearing a correction eyewear and with an updated acuity level that is greater than the visual acuity threshold.

Illustration of the Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method of implementing a virtual vision test, comprising: at an electronic device including a head-mounted display (HMD) and a camera: executing a user application configured to enable the virtual vision test; generating a virtual reality (VR) user interface corresponding to a three-dimensional (3D) virtual environment; focusing the camera on an eye area of a user wearing the electronic device; displaying, on the user interface, a visual stimulus corresponding to the virtual vision test; while displaying the visual stimulus, in real time, capturing a sequence of eye images using the camera of the electronic device; determining eye movement information including a temporal sequence of eyeball positions based on the sequence of eye images; and comparing the visual stimulus and the eye movement information to determine an eye health condition.

Clause 2. The method of Clause 1, wherein determining the eye movement information further comprises applying an eye trajectory model to process the sequence of eye images jointly and identify an eyeball trajectory including the temporal sequence of eyeball positions.

Clause 3. The method of Clause 1 or 2, wherein determining the eye movement information further comprises, for each of the sequence of eye images: processing the respective eye image to identify one or more reference locations; and determining a respective eyeball position with respect to the one or more reference locations.

Clause 4. The method of any of Clauses 1-3, further comprising, for each of the sequence of eye images: cropping the respective eye image to include a respective eye of the user based on a predefined aspect ratio; and after cropping, adjusting a resolution of the respective eye image to a predefined resolution.

Clause 5. The method of any of Clauses 1-4, wherein determining the eye movement information further comprises: applying an eye position model to process each of the sequence of eye images and identify a respective eyeball position in each eye image; and consolidating respective eyeball positions in the sequence of eye images to the temporal sequence of eyeball positions.

Clause 6. The method of Clause 5, further comprising obtaining the eye position model from a server, and the server is communicatively coupled to the electronic device via one or more communication networks and is configured to manage the user application and a plurality of user accounts.

Clause 7. The method of Clause 6, further comprising: obtaining a plurality of test eye images and associated ground truth eyeball positions; training the eye position model with the plurality of test eye images and the associated ground truth eyeball positions; and sending the eye position model to the electronic device after training.

Clause 8. The method of any of Clauses 1-7, wherein comparing the visual stimulus and the eye movement information further comprises generating a comparison result including one or more of: an eyeball response time, a success rate, an eyeball position trajectory, whether an eyeball focuses, or an offset from a correct focal point.

Clause 9. The method of any of Clauses 1-8, wherein determining the eye movement information further comprises, for each of the sequence of eye images: determining a respective head orientation; and adjusting the respective eyeball position based on the respective head orientation.

Clause 10. The method of any of Clauses 1-9, wherein the eye health condition includes an eye's focusing capability, the method further comprising in response to the visual stimulus staying at a fixed position on the user interface, determining that the temporal sequence of eyeball positions follows the visual stimulus and moves around within a positional vibration range around an eye position.

Clause 11. The method of any of Clauses 1-10, further comprising: in response to the visual stimulus, determining one or more response times associated with the temporal sequence of eyeball positions; and based on the one or more response times, determining whether the eye health condition of the user includes a predefined neurological defect.

Clause 12. The method of any of Clauses 1-11, wherein the visual stimulus includes a sequence of optotypes, the method further comprising: in response to the visual stimulus, determining a success rate of the temporal sequence of eyeball positions following each of the sequence of optotypes; and based on the success rate, determining the eye health condition of the user.

Clause 13. The method of any of Clauses 1-12, wherein the visual stimulus includes a sequence of optotypes, the method further comprising: determining one or more response times associated with a first subset of the temporal sequence of eyeball positions associated with a first subset of optotypes; and based on the one or more response times, dynamically adjusting a display parameter of a second subset of optotypes following the first subset of optotypes.

Clause 14. The method of Clause 13, wherein the display parameter of the second subset of optotypes includes a display size, a spatial pitch, a temporal pitch, a contrast level, and a brightness level of the second subset of optotypes.

Clause 15. The method of any of Clauses 1-14, further comprising applying an ocular microtremor model to process the sequence of eye images jointly and identify an ocular microtremor level.

Clause 16. The method of any of Clauses 1-15, further comprising determining an ocular microtremor level based on the temporal sequence of eyeball positions.

Clause 17. A method at an electronic device including a head-mounted display (HMD) and a camera: executing a user application configured to enable the virtual vision test; generating a virtual reality (VR) user interface corresponding to a three-dimensional (3D) virtual environment; using the camera of the electronic device, capturing eyeball movement data that is representative of an eye position; and based on the eyeball movement data, comparing the visual stimulus and the eye movement information to determine an eyeball movement disorder.

Clause 18. The method of Clause 17, further comprising, based on the eye tracking disorder, prescribing a training regimen for the eye.

Clause 19. The method of Clause 18, further comprising displaying and providing the training regimen via the VR user interface.

Clause 20. The method of any of Clauses 17-19, wherein the capturing comprises: focusing the camera on an eye area of a user wearing the electronic device; displaying, on the user interface, a visual stimulus corresponding to the virtual vision test; and while displaying the visual stimulus, in real time, capturing a sequence of eye images using the camera of the electronic device.

Clause 21. The method of any of Clauses 17-19, further comprising any of the features of Clauses 1-16.

Clause 22. A non-transitory computer readable storage medium, storing one or more programs for execution by one or more processors of a computer system, the one or more programs including instructions for implementing a method in any of Clauses 1-21.

Clause 23. A computer system, comprising: one or more processors; and memory for storing one or more programs for execution by the one or more processors, the one or more programs including instructions for implementing a method in any of Clauses 1-21.

Clause 24. A method of implementing a virtual vision test, comprising: at an electronic device including a head-mounted display (HMD), one or more head straps, and a plurality of electrodes integrated in the one or more head straps: executing a user application configured to enable the virtual vision test; generating a virtual reality (VR) user interface corresponding to a three-dimensional (3D) virtual environment; rendering, on the HMD, a user interface including a visual first stimulus corresponding to the virtual vision test; while displaying the visual stimulus, in real time: collecting a plurality of electrical signals by the plurality of electrodes that contact a head of a user; and determining information of at least one of a second visual stimulus following the first visual stimulus or a user response to the first visual stimulus based on the plurality of electrical signals.

Clause 25. The method of Clause 24, wherein the plurality of electrodes is configured to form an electroencephalography (EEG) sensor system, and the plurality of electrical signals have a temporal resolution of milliseconds.

Clause 26. The method of Clause 24 or 25, wherein the visual stimulus corresponds to a temporal sequence of visual patterns, and includes a first visual pattern, the method further comprising, while displaying the first visual pattern: determining a response feature of the user response to the first visual pattern based on the plurality of electrical signals; and based on the response feature, dynamically selecting a subsequent visual pattern immediately following the first visual pattern and determining a next temporal separation between the first visual pattern and the subsequent visual pattern, the subsequent visual pattern corresponding to the second visual stimulus.

Clause 27. The method of Clause 26, wherein the response feature comprises a brain activity level, the method further comprising, in accordance with a determination that the brain activity level is lower than a focus threshold: increasing the next temporal separation compared with a current temporal separation between the first visual pattern and a previous visual pattern; or reducing a difficulty level of the subsequent visual pattern compared with that of the first visual pattern.

Clause 28. The method of Clause 26 or 27, wherein the response feature comprises a response time, the method further comprising, in accordance with a determination that the response time is greater than a response threshold: increasing the next temporal separation compared with a current temporal separation between the first visual pattern and a previous visual pattern; or reducing a difficulty level of the subsequent visual pattern compared with that of the first visual pattern.

Clause 29. The method of any of Clauses 26-28, wherein the virtual vision test is one of a visual acuity test, a visual field test, a visual depth test, a color blindness test, a retinoscopy, a refraction test, an astigmatism test, and a contact lens exam, and the first visual pattern is selected from a plurality of predefined visual patterns to implement the virtual vision test and configured to be displayed with one or more adjustable display parameters.

Clause 30. The method of any of Clauses 24-29, further comprising, while displaying a first visual pattern: determining a response feature of the user response to the first visual stimulus based on the plurality of electrical signals; wherein the response feature comprises one or more of: a brain activity level, a response time, whether each of one or more feature neural events occurs, whether the user catches a prompt, or whether the user recognizes or speculates about the first visual stimulus.

Clause 31. The method of any of Clauses 24-30, further comprising: applying a response analysis model to process a subset of the plurality of electrical signals, which is recorded immediately after a first visual pattern, determining the user response to the first visual pattern, the user response including whether the user speculates about the first visual pattern.

Clause 32. The method of any of Clauses 24-31, wherein the virtual vision test comprises a color vision test, and the first visual pattern is applied in the color vision test to evaluates whether there are difficulties distinguishing between different colors, and the user response to the color vision test is automatically determined from the plurality of electrical signals without user intervention.

Clause 33. The method of any of Clauses 24-32, further comprising: collecting the user response to a first visual pattern using a microphone or a camera of the electronic device; and applying a response analysis model to process a subset of the plurality of electrical signals, which is recorded immediately after the first visual pattern, generating a confidence score associated with the user response.

Clause 34. The method of any of Clauses 24-33, further comprising: obtaining a response analysis model from a server associated with the electronic device; and applying the response analysis model to process the plurality of electrical signals, thereby determining information of at least one of the second visual stimulus or the user response to the first visual stimulus.

Clause 35. The method of Clause 34, further comprising, before applying the response analysis model, at the server: collecting a plurality of historical visual stimuli; collecting, from a plurality of users, a collection of historical electrical signals that are associated with the plurality of historical visual stimuli; and training a response analysis model based on the plurality of historical visual stimuli and the collection of historical electrical signals.

Clause 36. The method of Clause 35, wherein the plurality of historical visual stimuli and the collection of historical electrical signals are communicated to the server in an encrypted format, the method further comprising, at the server: after receiving the plurality of historical visual stimuli and the collection of historical electrical signals, decrypting the plurality of historical visual stimuli and the collection of historical electrical signals.

Clause 37. A method of implementing a virtual vision test, comprising: at an electronic device including a head-mounted display (HMD) and a plurality of electrodes configured to contact a head of a user when the user wears the electronic device: rendering, on the HMD, a user interface including a first visual stimulus corresponding to the virtual vision test; while displaying the visual stimulus, in real time: collecting a plurality of electrical signals from the head of the user by the plurality of electrodes; and determining information of at least one of a second visual stimulus following the first visual stimulus or a spontaneous neural response to the first visual stimulus based on the plurality of electrical signals.

Clause 38. The method of Clause 37, wherein the information of the second visual stimulus is determined based on the plurality of electrical signals and includes s type and one or more display parameters of the second visual stimulus.

Clause 39. The method of Clause 38, wherein the one or more display parameters of the second visual stimulus include a virtual distance at which the second visual stimulus is displayed in a 3D virtual environment.

Clause 40. The method of Clause 37, wherein the information of the spontaneous neural response is determined based on the plurality of electrical signals, the method further comprising: identifying a neural disorder based on the information of the spontaneous neural response.

Clause 41. The method of Clause 37, further comprising any of the features of Clauses 24-36.

Clause 42. A non-transitory computer readable storage medium, storing one or more programs for execution by one or more processors of a computer system, the one or more programs including instructions for implementing a method in any of Clauses 24-41.

Clause 43. A computer system, comprising: one or more processors; and memory for storing one or more programs for execution by the one or more processors, the one or more programs including instructions for implementing a method in any of Clauses 24-41.

Clause 44. A method of implementing a virtual vision test, comprising: at an electronic device including a head-mounted display (HMD): establishing a wireless communication link with a wearable device associated with a user of the electronic device; rendering, on the HMD, a user interface including a first visual stimulus corresponding to the virtual vision test; and while displaying the visual stimulus, in real time: collecting a stream of biometric data from the wearable device via the wireless communication link; and determining information of at least one of a second visual stimulus following the first visual stimulus and a user response to the first visual stimulus based on the stream of biometric data.

Clause 45. The method of Clause 44, further comprising: executing a user application configured to enable the virtual vision test; generating the user interface corresponding to a three-dimensional (3D) virtual reality environment.

Clause 46. The method of Clause 44 or 45, wherein the wireless communication link is configured to communicate the stream of biometric data using a short-range wireless protocol selected from Bluetooth, Wi-Fi, Near-Link, near-field communication (NFC), LPWAN, ultra-wideband (UWB) and IEEE 802.15.

Clause 47. The method of any of Clauses 44-46, wherein the wearable device comprises one or more of: a motion sensor, an electrical heart sensor, an optical heart sensor, a blood oxygen sensor, a galvanic skin response sensor, or a body temperature sensor, and wherein the wearable device is configured to measure one or more sensing signals and generate the stream of biometric data based on the one or more sensing signals.

Clause 48. The method of any of Clauses 44-47, further comprising after receiving the stream of biometric data, decrypting the stream of biometric data.

Clause 49. The method of any of Clauses 44-48, wherein the visual stimulus corresponds to a temporal sequence of visual patterns, and comprises a first visual pattern, the method further comprising, while displaying the first visual pattern: determining a response feature of the user response to the first visual pattern based on the stream of biometric data; and based on the response feature, dynamically selecting a subsequent visual pattern immediately following the first visual pattern and determining a next temporal separation between the first visual pattern and the subsequent visual pattern, the subsequent visual pattern corresponding to the second visual stimulus.

Clause 50. The method of Clause 49, further comprising: determining a focus level based on the stream of biometric data; and in accordance with a determination that the focus level is lower than a focus threshold: increasing the next temporal separation compared with a current temporal separation between the first visual pattern and a previous visual pattern; or reducing a difficulty level of the subsequent visual pattern compared with that of the first visual pattern.

Clause 51. The method of Clause 49 or 50, wherein the response feature comprises a response time, the method further comprising, in accordance with a determination that the response time is greater than a response threshold: increasing the next temporal separation compared with a current temporal separation between the first visual pattern and a previous visual pattern; or reducing a difficulty level of the subsequent visual pattern compared with that of the first visual pattern.

Clause 52. The method of any of Clauses 49-51, wherein the virtual vision test is one of a visual acuity test, a visual field test, a visual depth test, a color blindness test, a retinoscopy, a refraction test, an astigmatism test, and a contact lens exam., and the first visual pattern is selected from a plurality of predefined visual patterns to implement the virtual vision tests and configured to be displayed with one or more adjustable display parameters.

Clause 53. The method of any of Clauses 44-52, further comprising, while displaying a first visual pattern: determining a response feature of the user response to the first visual stimulus based on the stream of biometric data; wherein the response feature comprises one or more of: a motion level, a stress level, whether each of one or more feature events occurs, whether the user catches a prompt, or whether the user recognizes or speculates about the first visual stimulus.

Clause 54. The method of any of Clauses 44-53, further comprising applying a response analysis model to process a subset of the stream of biometric data, which is recorded immediately after a first visual pattern, determining the user response to the first visual pattern, the user response including whether the user speculates about the first visual pattern.

Clause 55. The method of Clause 54, wherein the virtual vision test comprises a color vision test, and the first visual pattern is applied in the color vision test to evaluates whether there are difficulties distinguishing between different colors, and the user response to the color vision test is automatically determined from the stream of biometric data.

Clause 56. The method of any of Clauses 44-55, further comprising: collecting the user response to a first visual pattern using a microphone or a camera of the electronic device; and applying a response analysis model to process a subset of the stream of biometric data, which is recorded immediately after the first visual pattern, generating a confidence score associated with the user response.

Clause 57. The method of any of Clauses 44-56, further comprising: obtaining a response analysis model from a server associated with the electronic device; and applying the response analysis model to process the stream of biometric data, thereby determining the information of at least one of the first visual stimulus and the user response to the first visual stimulus.

Clause 58. The method of Clause 57, further comprising, before applying the response analysis model, at the server: collecting a plurality of historical visual stimuli; collecting, from a plurality of users, a collection of historical biometric data that are associated with the plurality of historical visual stimuli; and training a response analysis model based on the plurality of historical visual stimuli and the collection of historical biometric data.

Clause 59. A method of implementing a virtual vision test, comprising: at an electronic device including a head-mounted display (HMD): rendering, on the HMD, a user interface including a first visual stimulus corresponding to the virtual vision test; and while displaying the visual stimulus, in real time: collecting a stream of biometric data from the wearable device; and determining information of at least one of a second visual stimulus following the first visual stimulus and a spontaneous neural response to the first visual stimulus based on the stream of biometric data.

Clause 60. The method of Clause 59, wherein the information of the second visual stimulus is determined based on the stream of biometric data and includes s type and one or more display parameters of the second visual stimulus.

Clause 61. The method of Clause 60, wherein the one or more display parameters of the second visual stimulus include a virtual distance at which the second visual stimulus is displayed in a 3D virtual environment.

Clause 62. The method of Clause 59, wherein the information of the spontaneous neural response is determined based on the stream of biometric data, the method further comprising: identifying a neural disorder based on the information of the spontaneous neural response.

Clause 63. The method of Clause 59, further comprising any of the features of Clauses 44-58.

Clause 64. A non-transitory computer readable storage medium, storing one or more programs for execution by one or more processors of a computer system, the one or more programs including instructions for implementing a method in any of Clauses 44-63.

Clause 65. A computer system, comprising: one or more processors; and memory for storing one or more programs for execution by the one or more processors, the one or more programs including instructions for implementing a method in any of Clauses 44-63.

Clause 66. A method of implementing a virtual vision test, comprising: at an electronic device including a head-mounted display (HMD) and a camera: directing the camera to an eye area of a user wearing the electronic device; displaying, on the HMD, a visual stimulus; while displaying the visual stimulus, in real time, capturing a sequence of eye images using the camera of the electronic device, each eye image including a respective region of interest (ROI) corresponding to a subset of the eye area of the user; extracting biomedical data from the sequence of eye images; obtaining a user response to the visual stimulus; and generating an output based on the user response and the biomedical data, the output indicating at least whether the user response satisfies a criterion.

Clause 67. The method of Clause 66, further comprising extracting a feature event in response to the visual stimulus based on the biomedical data.

Clause 68. The method of Clause 67, wherein the biomedical data comprises a temporal sequence of heart rate data or a temporal sequence of blood oxygen levels.

Clause 69. The method of Clause 68, further comprising applying a biomedical data model to process the biomedical data and identify the feature event.

Clause 70. The method of any of Clauses 67-69, wherein the user response and the feature event of the biomedical data have delays from the visual stimulus, the method further comprising, in accordance with a determination that the user response and the biomedical data match each other and that the delays are below a first threshold delay, determining that the user response satisfies the criterion.

Clause 71. The method of any of Clauses 67-69, further comprising in accordance with a determination that the user response is delayed from the feature event of the biomedical data beyond a second threshold delay, determining that the user has a neural pathway disease, wherein the output is generated to indicate the neural pathway disease and that the user response does not satisfy the criterion.

Clause 72. The method of any of Clauses 67-69, further comprising in accordance with a determination that the feature event of the biomedical data is delayed from the user response beyond a third threshold delay, determining that the user response is not reliable, wherein the output is generated to indicate the user response does not satisfy the criterion.

Clause 73. The method of any of Clauses 67-69, wherein the user response and the feature event of the biomedical data have delays from the visual stimulus, the method further comprising in accordance with a determination that the delays from the visual stimulus are above a first threshold delay for the user response and the feature event of the biomedical data, determining that the user response does not satisfy the criterion, the output including a message indicating that the user needs a break.

Clause 74. The method of any of Clauses 66-73, wherein generating the output further comprises: determining an active response time of the user response with respect to the visual stimulus; determining a passive response time with respect to the visual stimulus based on the biomedical data; and comparing the active response time and the passive response time to generate the output.

Clause 75. The method of any of Clauses 66-74, further comprising: executing a user application configured to enable the virtual vision test; generating a virtual reality (VR) user interface corresponding to a three-dimensional (3D) virtual environment, wherein the visual stimulus is displayed on the VR user interface.

Clause 76. The method of any of Clauses 66-75, further comprising: cropping each of the plurality of eye images to extract the respective ROI of each eye image; and apply a biomedical data extraction model to process respective ROIs of the plurality of eye images and extract the biomedical data.

Clause 77. The method of any of Clauses 66-76, wherein the biomedical data corresponds to one of a heart rate, a blood oxygen level, and a galvanic skin response (GSR).

Clause 78. The method of any of Clauses 66-77, further comprising: obtaining a biomedical data model from a server associated with the electronic device; and applying the biomedical data model to process the biomedical data.

Clause 79. The method of Clause 78, further comprising, before applying the biomedical data model, at the server: collecting a plurality of historical visual stimuli; collecting a collection of historical biomedical data that are associated with the plurality of historical visual stimuli; and training a biomedical data model based on the plurality of historical visual stimuli and the collection of historical biomedical data.

Clause 80. A method of implementing a virtual vision test, comprising: at an electronic device including a head-mounted display (HMD) and a biomedical sensor: displaying, on the HMD, a visual stimulus; while displaying the visual stimulus, in real time, monitoring, by the biomedical sensor, a respective region of interest (ROI) corresponding to an eye area of the user to generate a stream of biomedical data; obtaining an active user response to the visual stimulus; and generating an output based on the active user response and the stream of biomedical data, the output indicating at least whether the active use response satisfies a criterion.

Clause 81. The method of Clause 80, wherein the stream of biomedical data corresponds to at least one of a blood oxygen level, a body temperature level, or a heart rate.

Clause 82. The method of Clause 80, further comprising any of the features of Clauses 66-79.

Clause 83. A non-transitory computer readable storage medium, storing one or more programs for execution by one or more processors of a computer system, the one or more programs including instructions for implementing a method in any of Clauses 66-82.

Clause 84. A computer system, comprising: one or more processors; and memory for storing one or more programs for execution by the one or more processors, the one or more programs including instructions for implementing a method in any of Clauses 66-82.

Clause 85. A method for testing vision, comprising: at a computer device including a display, one or more processors, and memory: obtaining historical vision data of a patient user associated with the computer device; based on the historical vision data, determining an ordered sequence of vision tests including a first vision test for the patient user, wherein the first vision test is followed by a set of one or more subsequent vision tests of the ordered sequence of vision tests; executing a user application configured to enable the ordered sequence of vision tests, including rendering a user interface on the display; displaying, on the user interface, a first visual stimulus corresponding to the first vision test; obtaining a user response to the first visual stimulus; and dynamically adjusting a set of one or more subsequent visual stimuli based on the user response to the first vision test.

Clause 86. The method of Clause 85, wherein dynamically adjusting the set of one or more subsequent visual stimuli further comprises adjusting at least one of a total number or an order of the set of one or more subsequent visual stimuli.

Clause 87. The method of Clause 85 or 86, wherein dynamically adjusting the set of one or more subsequent visual stimuli further comprises, based on the user response, implementing one or more of: bypassing a first one of the set of one or more subsequent visual stimuli; adding an alternative visual stimulus to the set of one or more subsequent visual stimuli; shortening a length of a second one of the set of one or more subsequent vision tests; extending a length of a third one of the set of one or more subsequent vision tests; advancing a fourth one of the set of one or more subsequent visual stimuli; postponing a fifth one of the set of one or more subsequent visual stimuli; or swapping two of the set of one or more subsequent vision tests.

Clause 88. The method of any of Clauses 85-87, wherein dynamically adjusting the set of one or more subsequent visual stimuli further comprises determining a length, content, a temporal separation, and a display parameter of at least one subsequent vision test.

Clause 89. The method of Clause 88, wherein the display parameter is one of: a resolution, a display size, a spatial pitch, a temporal pitch, a contrast level, and a brightness level of a visual stimulus associated with the at least one subsequent vision test.

Clause 90. The method of any of Clauses 85-89, wherein dynamically adjusting the set of one or more subsequent visual stimuli further comprises: determining a difficulty level associated with the set of one or more subsequent visual stimuli; adjusting the difficulty level based on the user response; and based on the adjusted difficulty level, selecting one of a plurality of predefined vision tests to be rendered on the user interface for the patient user.

Clause 91. The method of any of Clauses 85-90, wherein the first vision test includes both the first visual stimulus and the set of one or more subsequent visual stimuli, and the user response is obtained after the first visual stimulus is displayed, the method further comprising dynamically adjusting the set of one or more subsequent visual stimuli based on the user response to the first visual stimulus.

Clause 92. The method of any of Clauses 85-91, wherein the set of one or more subsequent visual stimuli includes at least one visual stimulus located in at least one vision test distinct from the first vision test.

Clause 93. The method of any of Clauses 85-92, wherein the set of one or more subsequent visual stimuli includes two visual stimuli that are located in the first vision test and an another vision test distinct from the first vision test.

Clause 94. The method of any of Clauses 85-93, wherein each of the set of one or more subsequent visual stimuli comprises a visual pattern that is displayed with a temporal separation from an immediately preceding visual pattern or an immediately subsequent visual pattern, and content, the temporal separation, and a display parameter of at least one subsequent visual stimulus is adjusted based on the user response to the first visual stimulus.

Clause 95. The method of any of Clauses 85-94, wherein the historical vision data of the patient user comprises a document including a medical history of the patient user, and determining the ordered sequence of vision tests further comprises: extracting one or more key words concerning an eye health condition of the patient user from the document; selecting the ordered sequence of vision tests from a plurality of predefined sequences of vision tests based on the one or more key words; and determining one or more respective visual stimulus of each vision test.

Clause 96. The method of any of Clauses 85-95, wherein determining the ordered sequence of vision tests further comprises applying a medical information processing model to process the historical vision data and selecting the ordered sequence of vision tests from a plurality of predefined sequences of vision tests.

Clause 97. The method of any of Clauses 85-96, further comprising: presenting to the patient user a plurality of prompts; and obtaining a plurality of user answers to the plurality of prompts, wherein the ordered sequence of vision tests are determined based on both the historical vision data and the plurality of user answers.

Clause 98. The method of any of Clauses 85-97, wherein the display comprises a head-mounted display (HMD), and the user interface comprises a virtual reality (VR) user interface corresponding to a three-dimensional (3D) virtual environment, and wherein the ordered sequence of vision tests is rendered in the 3D virtual environment.

Clause 99. A method for testing vision, comprising: at a computer device including a display, one or more processors, and memory: selecting a sequence of visual stimuli including a first visual stimulus for the patient user; displaying, on the display, the first visual stimulus corresponding to the first vision test; obtaining a user response to the first visual stimulus; and dynamically adjusting a set of one or more subsequent visual stimuli that follow the first stimulus based on the user response to the first vision test.

Clause 100. The method of Clause 99, wherein the first visual stimulus and the set of one or more subsequent visual stimuli are included in a first vision test.

Clause 101. The method of Clause 99, wherein the first visual stimulus included in the first vision test, and the set of one or more subsequent visual stimuli are included in one or more subsequent vision tests the follow the first vision test.

Clause 102. The method of any of Clauses 99-101, wherein dynamically adjusting the set of one or more subsequent visual stimuli further comprises determining at least one of a length, content, a temporal separation, and a display parameter of each respective subsequent visual stimulus.

Clause 103. The method of Clause 102, wherein the display parameter is one of: a virtual distance, a resolution, a display size, a spatial pitch, a temporal pitch, a contrast level, and a brightness level of the respective subsequent visual stimulus.

Clause 104. The method of Clause 99, further comprising any of the features of Clauses 85-98.

Clause 105. A non-transitory computer readable storage medium, storing one or more programs for execution by one or more processors of a computer system, the one or more programs including instructions for implementing a method in any of Clauses 85-104.

Clause 106. A computer system, comprising: one or more processors; and memory for storing one or more programs for execution by the one or more processors, the one or more programs including instructions for implementing a method in any of Clauses 85-104.

Clause 107. A method for displaying media content, comprising: at an electronic device including a display, one or more processors, and memory: obtaining the media content to be rendered on the display; obtaining information of a visual deficiency of a user associated with the display; based on the information of the visual deficiency of the user, compensating the media content to generate compensated media content; and rendering the compensated media content on the display for the user.

Clause 108. The method of Clause 107, further comprising: rendering a sequence of visual stimuli on a user interface; obtaining a plurality of user responses to the sequence of visual stimuli; and identifying the visual deficiency of the user based on the plurality of user responses.

Clause 109. The method of Clause 107 or 108, wherein the visual deficiency comprises a color vision deficiency corresponding to a difficulty in telling a difference among a plurality of colors, and compensating the media content further comprises adjusting the plurality of colors in the media content based on the visual deficiency of the user, thereby generating the compensated media content.

Clause 110. The method of Clause 109, wherein the color vision deficiency comprises a red-green color blindness, and the information of the visual deficiency comprises a severity level of insensitivity to a difference between red and green colors, and wherein compensating the media content further comprises adjusting a color shade of at least one of the red or green colors to generate the compensated media content.

Clause 111. The method of any of Clauses 107-110, wherein the visual deficiency comprises a vision field impairment, and the information of the visual deficiency identifies a first location of the vision field impairment, compensating the media content further comprises: displaying a mark identifying the first location of the vision field impairment.

Clause 112. The method of any of Clauses 107-110, wherein the visual deficiency comprises a vision field impairment, and the information of the visual deficiency identifies a first location of the vision field impairment, compensating the media content further comprises: displaying a subset of media content corresponding to the first location of the vision field impairment in a distinct location.

Clause 113. The method of any of Clauses 107-112, wherein compensating the media content further comprises adjusting one or more display parameters of: a resolution, a contrast level, a brightness level, and a refresh rate of the display.

Clause 114. The method of any of Clauses 107-113, wherein the display comprises a head-mounted display (HMD), and a user interface comprises a virtual reality (VR) user interface corresponding to a three-dimensional (3D) virtual environment, and wherein the compensated media content is rendered on the user interface and in the 3D virtual environment.

Clause 115. The method of Clause 114, wherein the visual deficiency comprises a visual acuity level that is lower than a visual acuity threshold, and the media content is compensated and rendered such that the user can review the media content without wearing a correction eyewear and with an updated acuity level that is greater than the visual acuity threshold.

Clause 116. The method of any of Clauses 107-115, further comprising: obtaining a document including a medical history of the user; and extracting the information of the visual deficiency of the user from the document.

Clause 117. The method of Clause 116, wherein extracting the information of the visual deficiency further comprises applying a medical information processing model to process the medical history and determine at least a type and a severity level of the visual deficiency of the user.

Clause 118. The method of Clause 117, further comprising: obtaining the medical information processing model from a server associated with the computer device, after the medical information processing model is trained on the server.

Clause 119. A method for displaying media content, comprising: at an electronic device including a display, one or more processors, and memory: obtaining the media content to be rendered on the display; obtaining information of a visual deficiency of a user associated with the display; determining a content compensation mode based on the information of the visual deficiency; based on the content compensation mode, compensating the media content to generate compensated media content; and rendering the compensated media content on the display for the user.

Clause 120. The method of Clause 119, further comprising: determining one or more predefined compensation parameters applied in compensation of the media for the content compensation mode.

Clause 121. The method of Clause 119, further comprising: based on the information of the visual deficiency of the user, determining one or more compensation parameters applied in compensation of the media for the content compensation mode.

Clause 122. The method of Clause 119, further comprising any of the features of Clauses 107-118.

Clause 123. A non-transitory computer readable storage medium, storing one or more programs for execution by one or more processors of a computer system, the one or more programs including instructions for implementing a method in any of Clauses 107-122.

Clause 124. A computer system, comprising: one or more processors; and memory for storing one or more programs for execution by the one or more processors, the one or more programs including instructions for implementing a method in any of Clauses 107-122.

Clause 125. An interactive virtual-reality method for performing a virtual vision test and displaying media, as discussed in any of the above clauses.

Clause 126. A non-transitory computer readable storage medium, storing one or more programs for execution by one or more processors of a computer system, the one or more programs including instructions for implementing a method in any of Clauses 1-122 and 125.

Clause 127. A computer system, comprising: one or more processors; and memory for storing one or more programs for execution by the one or more processors, the one or more programs including instructions for implementing a method in any of Clauses 1-122 and 125.

In some embodiments, any of the above clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

FURTHER CONSIDERATIONS

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

As used herein, the term "about" is relative to the actual value stated, as will be appreciated by those of skill in the art, and allows for approximations, inaccuracies and limits of measurement under the relevant circumstances. In one or more aspects, the terms "about," "substantially," and "approximately" may provide an industry-accepted tolerance for their corresponding terms and/or relativity between items.

As used herein, the term "comprising" indicates the presence of the specified integer(s), but allows for the possibility of other integers, unspecified. This term does not imply any particular proportion of the specified integers. Variations of the word "comprising," such as "comprise" and "comprises," have correspondingly similar meanings.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for testing vision, comprising:

at a computer device including a display, one or more processors, and memory:

obtaining historical vision data of a patient user associated with the computer device;

based on the historical vision data, determining an ordered sequence of vision tests including a first vision test for the patient user, wherein the first vision test is followed by a set of one or more subsequent vision tests of the ordered sequence of vision tests;

executing a user application configured to enable the ordered sequence of vision tests, including rendering a user interface on the display;

displaying, on the user interface, a first visual stimulus corresponding to the first vision test;

obtaining a user response to the first visual stimulus; and dynamically adjusting a set of one or more subsequent visual stimuli based on the user response to the first vision test.

2. The method of claim 1, wherein dynamically adjusting the set of one or more subsequent visual stimuli further comprises adjusting at least one of a total number or an order of the set of one or more subsequent visual stimuli.

3. The method of claim 1, wherein dynamically adjusting the set of one or more subsequent visual stimuli further comprises, based on the user response, implementing one or more of:

bypassing a first one of the set of one or more subsequent visual stimuli;

adding an alternative visual stimulus to the set of one or more subsequent visual stimuli;

shortening a length of a second one of the set of one or more subsequent vision tests;

extending a length of a third one of the set of one or more subsequent vision tests;

advancing a fourth one of the set of one or more subsequent visual stimuli;

postponing a fifth one of the set of one or more subsequent visual stimuli; or swapping two of the set of one or more subsequent vision tests.

4. The method of claim 1, wherein dynamically adjusting the set of one or more subsequent visual stimuli further comprises determining a length, content, a temporal separation, and a display parameter of at least one subsequent vision test.

5. The method of claim 4, wherein the display parameter is one of: a resolution, a display size, a spatial pitch, a temporal pitch, a contrast level, and a brightness level of a visual stimulus associated with the at least one subsequent vision test.

6. The method of claim 1, wherein dynamically adjusting the set of one or more subsequent visual stimuli further comprises:

determining a difficulty level associated with the set of one or more subsequent visual stimuli;

adjusting the difficulty level based on the user response; and based on the adjusted difficulty level, selecting one of a plurality of predefined vision tests to be rendered on the user interface for the patient user.

7. The method of claim 1, wherein the first vision test includes both the first visual stimulus and the set of one or more subsequent visual stimuli, and the user response is obtained after the first visual stimulus is displayed, the method further comprising dynamically adjusting the set of one or more subsequent visual stimuli based on the user response to the first visual stimulus.

8. The method of claim 1, wherein the set of one or more subsequent visual stimuli includes at least one visual stimulus located in at least one vision test distinct from the first vision test.

9. The method of claim 1, wherein the set of one or more subsequent visual stimuli includes two visual stimuli that are located in the first vision test and an another vision test distinct from the first vision test.

10. The method of claim 1, wherein each of the set of one or more subsequent visual stimuli comprises a visual pattern that is displayed with a temporal separation from at least one of an immediately preceding visual pattern or an immediately subsequent visual pattern, and content, the temporal separation, and a display parameter of at least one subsequent visual stimulus is adjusted based on the user response to the first visual stimulus.

11. The method of claim 1, wherein the historical vision data of the patient user comprises a document including a medical history of the patient user, and determining the ordered sequence of vision tests further comprises:

extracting one or more key words concerning an eye health condition of the patient user from the document;

selecting the ordered sequence of vision tests from a plurality of predefined sequences of vision tests based on the one or more key words; and determining one or more respective visual stimulus of each vision test.

12. The method of claim 1, wherein determining the ordered sequence of vision tests further comprises applying a medical information processing model to process the historical vision data and selecting the ordered sequence of vision tests from a plurality of predefined sequences of vision tests.

13. The method of claim 1, further comprising:

presenting to the patient user a plurality of prompts; and obtaining a plurality of user answers to the plurality of prompts, wherein the ordered sequence of vision tests are determined based on both the historical vision data and the plurality of user answers.

14. The method of claim 1, wherein the display comprises a head-mounted display (HMD), and the user interface comprises a virtual reality (VR) user interface corresponding to a three-dimensional (3D) virtual environment, and wherein the ordered sequence of vision tests is rendered in the 3D virtual environment.

15. A non-transitory computer readable storage medium, storing one or more programs for execution by one or more processors of a computer system including a display, the one or more programs including instructions for:

obtaining historical vision data of a patient user associated with the computer device;

based on the historical vision data, determining an ordered sequence of vision tests including a first vision test for the patient user, wherein the first vision test is followed by a set of one or more subsequent vision tests of the ordered sequence of vision tests;

executing a user application configured to enable the ordered sequence of vision tests, including rendering a user interface on the display;

displaying, on the user interface, a first visual stimulus corresponding to the first vision test;

obtaining a user response to the first visual stimulus; and dynamically adjusting a set of one or more subsequent visual stimuli based on the user response to the first vision test.

16. The non-transitory computer readable storage medium of claim 15, wherein dynamically adjusting the set of one or more subsequent visual stimuli further comprises adjusting at least one of a total number or an order of the set of one or more subsequent visual stimuli.

17. The non-transitory computer readable storage medium of claim 15, wherein dynamically adjusting the set of one or more subsequent visual stimuli further comprises:

determining a difficulty level associated with the set of one or more subsequent visual stimuli;

adjusting the difficulty level based on the user response; and based on the adjusted difficulty level, selecting one of a plurality of predefined vision tests to be rendered on the user interface for the patient user.

18. A computer device, comprising:

a display;

one or more processors; and memory for storing one or more programs for execution by the one or more processors, the one or more programs including instructions for:

obtaining historical vision data of a patient user associated with the computer device;

based on the historical vision data, determining an ordered sequence of vision tests including a first vision test for the patient user, wherein the first vision test is followed by a set of one or more subsequent vision tests of the ordered sequence of vision tests;

executing a user application configured to enable the ordered sequence of vision tests, including rendering a user interface on the display;

displaying, on the user interface, a first visual stimulus corresponding to the first vision test;

obtaining a user response to the first visual stimulus; and dynamically adjusting a set of one or more subsequent visual stimuli based on the user response to the first vision test.

19. The computer device of claim 18, wherein dynamically adjusting the set of one or more subsequent visual stimuli further comprises determining a length, content, a temporal separation, and a display parameter of at least one subsequent vision test.

20. The computer device of claim 19, wherein the display parameter is one of: a resolution, a display size, a spatial pitch, a temporal pitch, a contrast level, and a brightness level of a visual stimulus associated with the at least one subsequent vision test.

* * * * *